United States Patent
Salomon et al.

(10) Patent No.: US 11,104,951 B2
(45) Date of Patent: Aug. 31, 2021

(54) MOLECULAR SIGNATURES FOR DISTINGUISHING LIVER TRANSPLANT REJECTIONS OR INJURIES

(71) Applicants: THE SCRIPPS RESEARCH INSTITUTE, La Jolla, CA (US); NORTHWESTERN UNIVERSITY, Evanston, IL (US)

(72) Inventors: Daniel Salomon, San Diego, CA (US); Josh Levitsky, Evanston, IL (US); Sunil Kurian, San Diego, CA (US); Michael Abecassis, Highland Park, IL (US)

(73) Assignees: The Scripps Research Institute, La Jolla, CA (US); Northwestern University, Evanston, IL (US)

( * ) Notice: Subject to any disclaimer, the term of this patent is extended or adjusted under 35 U.S.C. 154(b) by 0 days.

(21) Appl. No.: 15/313,217

(22) PCT Filed: May 22, 2015

(86) PCT No.: PCT/US2015/032191
§ 371 (c)(1),
(2) Date: Nov. 22, 2016

(87) PCT Pub. No.: WO2015/179771
PCT Pub. Date: Nov. 26, 2015

(65) Prior Publication Data
US 2017/0183735 A1 Jun. 29, 2017

Related U.S. Application Data

(63) Continuation-in-part of application No. 14/481,167, filed on Sep. 9, 2014, now abandoned.

(60) Provisional application No. 62/029,038, filed on Jul. 25, 2014, provisional application No. 62/001,909, filed on May 22, 2014, provisional application No. 62/001,902, filed on May 22, 2014, provisional application No. 62/001,889, filed on May 22, 2014.

(51) Int. Cl.
| | | |
|---|---|---|
| C12Q 1/6883 | (2018.01) |
| G01N 33/574 | (2006.01) |
| G01N 33/50 | (2006.01) |
| G16H 50/30 | (2018.01) |
| G16H 20/40 | (2018.01) |
| G16H 20/10 | (2018.01) |
| G16H 20/17 | (2018.01) |
| G16H 50/70 | (2018.01) |
| G16H 50/20 | (2018.01) |
| G16H 40/63 | (2018.01) |
| G16H 10/20 | (2018.01) |
| G16H 10/40 | (2018.01) |

(52) U.S. Cl.
CPC ....... *C12Q 1/6883* (2013.01); *G01N 33/5088* (2013.01); *G16H 20/10* (2018.01); *G16H 20/17* (2018.01); *G16H 20/40* (2018.01); *G16H 40/63* (2018.01); *G16H 50/20* (2018.01); *G16H 50/30* (2018.01); *G16H 50/70* (2018.01); *C12Q 2537/165* (2013.01); *C12Q 2600/106* (2013.01); *C12Q 2600/112* (2013.01); *C12Q 2600/118* (2013.01); *C12Q 2600/136* (2013.01); *C12Q 2600/158* (2013.01); *G01N 2800/245* (2013.01); *G16H 10/20* (2018.01); *G16H 10/40* (2018.01); *Y02A 90/10* (2018.01)

(58) Field of Classification Search
None
See application file for complete search history.

(56) References Cited

U.S. PATENT DOCUMENTS

| | | |
|---|---|---|
| 5,210,015 A | 5/1993 | Gelfand et al. |
| 5,458,852 A | 10/1995 | Buechler |
| 5,480,792 A | 1/1996 | Buechler et al. |
| 5,525,524 A | 6/1996 | Buechler et al. |
| 5,538,848 A | 7/1996 | Livak et al. |
| 5,578,832 A | 11/1996 | Trulson et al. |
| 5,631,734 A | 5/1997 | Stern et al. |
| 5,679,526 A | 10/1997 | Buechler et al. |
| 5,824,799 A | 10/1998 | Buechler et al. |
| 5,851,776 A | 12/1998 | Valkirs |

(Continued)

FOREIGN PATENT DOCUMENTS

| | | |
|---|---|---|
| EP | 1850130 B1 | 11/2011 |
| EP | 2209916 B1 | 12/2011 |

(Continued)

OTHER PUBLICATIONS

Cardinale et al. Transcriptome Profiling of Human Ulcerative Colitis Mucosa Reveals Altered Expression of Pathways Enriched in Genetic Susceptibility Loci. May 1, 2014, PloS One. vol. 9, No. 5, e96153, pp. 1-11 and Table S1 Rank list of Denson biopsy data set for differential expression by empirical Bayes testing procedure, pp. 1-425.*

(Continued)

*Primary Examiner* — Channing S Mahatan
(74) *Attorney, Agent, or Firm* — Hugh Wang; Thomas Fitting

(57) ABSTRACT

By a genome-wide gene analysis of expression profiles of known or putative gene sequences in peripheral blood and biopsy samples, the present inventors have identified a consensus set of gene expression-based molecular biomarkers for distinguishing liver transplantation patients who have Acute Rejection (AR), Hepatitis C Virus Recurrence (HCV-R), both AR/HCV-R, or Acute Dysfunction No Rejection (ADNR). These molecular biomarkers are useful for diagnosis, prognosis and monitoring of liver transplantation patients.

13 Claims, 2 Drawing Sheets

(56) References Cited

U.S. PATENT DOCUMENTS

| | | |
|---|---|---|
| 5,855,527 A | 1/1999 | Koole |
| 5,863,736 A | 1/1999 | Haaland |
| 5,922,615 A | 7/1999 | Nowakowski et al. |
| 5,939,272 A | 8/1999 | Buechler et al. |
| 5,947,124 A | 9/1999 | Buechler et al. |
| 5,985,579 A | 11/1999 | Buechler et al. |
| 6,019,944 A | 2/2000 | Buechler |
| 6,020,165 A | 2/2000 | Yue et al. |
| 6,113,855 A | 9/2000 | Buechler |
| 6,143,576 A | 11/2000 | Buechler |
| 6,187,534 B1 | 2/2001 | Strom et al. |
| 6,623,738 B1 | 9/2003 | Tessier-Lavigne et al. |
| 6,878,518 B2 | 4/2005 | Whitehead |
| 6,927,028 B2 | 8/2005 | Dennis et al. |
| RE39,920 E | 11/2007 | Umansky et al. |
| 7,415,358 B2 | 8/2008 | Mendrick et al. |
| 7,426,441 B2 | 9/2008 | Mendrick et al. |
| 7,615,355 B2 | 11/2009 | Papadopoulos et al. |
| 7,645,575 B2 | 1/2010 | Wohlgemuth et al. |
| 7,741,038 B2 | 6/2010 | Sarwal et al. |
| 7,785,797 B2 | 8/2010 | Wohlgemuth et al. |
| 7,811,767 B2 | 10/2010 | Raulf et al. |
| 7,883,858 B2 | 2/2011 | Hood et al. |
| 7,994,286 B2 | 8/2011 | Watts et al. |
| 7,998,687 B2 | 8/2011 | Grass |
| 8,003,333 B2 | 8/2011 | Charlton |
| 8,333,970 B2 | 12/2012 | Aukerman et al. |
| 8,486,626 B2 | 7/2013 | Umansky et al. |
| 8,512,953 B2 | 8/2013 | Saito et al. |
| 8,586,006 B2 | 11/2013 | Hood et al. |
| 8,735,080 B2 | 5/2014 | Labrie et al. |
| 9,102,983 B2 | 8/2015 | Winkler et al. |
| 2004/0126767 A1 | 7/2004 | Anderberg et al. |
| 2006/0216722 A1 | 9/2006 | Betsholtz et al. |
| 2006/0263813 A1 | 11/2006 | Rosenberg et al. |
| 2006/0281122 A1 | 12/2006 | Bryant et al. |
| 2007/0099251 A1 | 5/2007 | Zhang et al. |
| 2007/0122806 A1 | 5/2007 | Strom et al. |
| 2008/0044403 A1 | 2/2008 | Sawitzki et al. |
| 2008/0131441 A1 | 6/2008 | Suthanthiran |
| 2009/0053195 A1 | 2/2009 | Raulf et al. |
| 2009/0053695 A1 | 2/2009 | Tanigawara et al. |
| 2009/0202531 A1 | 8/2009 | Aukerman et al. |
| 2009/0304705 A1 | 12/2009 | Grass |
| 2009/0311745 A1 | 12/2009 | Liebeton et al. |
| 2010/0022627 A1 | 1/2010 | Scherer |
| 2010/0068711 A1 | 3/2010 | Umansky et al. |
| 2010/0086928 A1 | 4/2010 | Feinberg |
| 2010/0120041 A1 | 5/2010 | Quaggin |
| 2010/0151467 A1 | 6/2010 | Wohlgemuth et al. |
| 2010/0190166 A1 | 7/2010 | Halloran |
| 2010/0196426 A1 | 8/2010 | Skog et al. |
| 2010/0233716 A1 | 9/2010 | Saint-Mezard et al. |
| 2010/0266579 A1 | 10/2010 | Cook et al. |
| 2010/0305000 A1 | 12/2010 | Mathew et al. |
| 2011/0003708 A1 | 1/2011 | Kinar et al. |
| 2011/0034532 A1 | 2/2011 | Li et al. |
| 2011/0039710 A1 | 2/2011 | Tibbetts |
| 2011/0065599 A1 | 3/2011 | Labrie et al. |
| 2011/0086051 A1 | 4/2011 | Zuckerman et al. |
| 2011/0171750 A1 | 7/2011 | Struck et al. |
| 2011/0189680 A1 | 8/2011 | Keown et al. |
| 2012/0003633 A1 | 1/2012 | Kuijpers et al. |
| 2012/0094853 A1 | 4/2012 | Clark et al. |
| 2012/0101001 A1 | 4/2012 | Suthanthiran |
| 2012/0135882 A1 | 5/2012 | Bottinger |
| 2012/0165207 A1 | 6/2012 | Butte et al. |
| 2012/0178642 A1 | 7/2012 | Salomon et al. |
| 2012/0192878 A1 | 8/2012 | Toyoda |
| 2012/0219542 A1 | 8/2012 | Reiser |
| 2012/0251527 A1 | 10/2012 | Reiser |
| 2012/0316076 A1* | 12/2012 | Sharp ............... G01N 33/6893 506/9 |
| 2013/0012860 A1 | 1/2013 | Suthanthiran et al. |
| 2013/0040301 A1 | 2/2013 | Strom et al. |
| 2013/0045873 A1 | 2/2013 | Hood et al. |
| 2013/0115232 A1 | 5/2013 | Ferrara et al. |
| 2013/0143223 A1 | 6/2013 | Hernandez-Fuentes et al. |
| 2013/0143755 A1 | 6/2013 | Sarwal et al. |
| 2013/0216557 A1 | 8/2013 | Bienkowska et al. |
| 2013/0236437 A1 | 9/2013 | Bishopric et al. |
| 2014/0030266 A1 | 1/2014 | Bucala et al. |
| 2014/0045915 A1 | 2/2014 | Skog et al. |
| 2014/0121126 A1 | 5/2014 | Bivona et al. |
| 2014/0135225 A1* | 5/2014 | Crow ............... C12Q 1/6883 506/9 |
| 2015/0011401 A1 | 1/2015 | Davicioni et al. |
| 2015/0167085 A1 | 6/2015 | Salomon et al. |
| 2016/0348174 A1 | 12/2016 | Sarwal |
| 2017/0137885 A1 | 5/2017 | Salomon et al. |
| 2017/0191128 A1 | 7/2017 | Salomon et al. |
| 2018/0371546 A1 | 12/2018 | Salomon et al. |
| 2019/0032135 A1 | 1/2019 | Salomon et al. |
| 2020/0208217 A1 | 7/2020 | Salomon et al. |

FOREIGN PATENT DOCUMENTS

| | | |
|---|---|---|
| GB | 2532672 A | 5/2016 |
| WO | WO-9710365 A1 | 3/1997 |
| WO | WO-9727317 A1 | 7/1997 |
| WO | WO-0238561 A1 | 5/2002 |
| WO | WO-03082859 A1 | 10/2003 |
| WO | WO-2004052359 A1 | 6/2004 |
| WO | WO-2004059293 A2 | 7/2004 |
| WO | WO-2005066156 A1 | 7/2005 |
| WO | WO-2007104537 A2 | 9/2007 |
| WO | WO-2008021290 A2 | 2/2008 |
| WO | WO-2008048970 A2 | 4/2008 |
| WO | WO-2009045104 A1 | 4/2009 |
| WO | WO-2009060035 A1 | 5/2009 |
| WO | WO-2009151600 A2 | 12/2009 |
| WO | WO-2010083121 A1 | 7/2010 |
| WO | WO-2011006119 A2 | 1/2011 |
| WO | WO-2011066380 A1 | 6/2011 |
| WO | WO-2013049892 A1 | 4/2013 |
| WO | WO-2014074501 A1 | 5/2014 |
| WO | WO-2015035177 A1 | 3/2015 |
| WO | WO-2015035203 A1 | 3/2015 |
| WO | WO-2015035367 A1 | 3/2015 |
| WO | WO-2015179771 A2 | 11/2015 |
| WO | WO-2015179773 | 11/2015 |
| WO | WO-2015179777 A2 | 11/2015 |
| WO | WO-2017136709 A2 | 8/2017 |
| WO | WO-2019217910 A1 | 11/2019 |

OTHER PUBLICATIONS

Abboudi, et al. Individualized immunosuppression in transplant patients: potential role of pharmacogenetics. Pharmgenomics Pers Med. 2012; 5: 63-72.

Anglicheau, et al. MicroRNA expression profiles predictive of human renal allograft status. PNAS 106, 5330-5335 (2009).

Anglicheau, et al. Noninvasive prediction of organ graft rejection and outcome using gene expression patterns. Transplantation. Jul. 27, 2008;86(2):192-9. doi: 10.1097/TP.0b013e31817eef7b.

Asaoka, et al. Differential transcriptome patterns for acute cellular rejection in recipients with recurrent hepatitis C after liver transplantation. Liver Transpl. Dec. 2009; 15(12):1738-49.

Banasik, et al. Chronic allograft nephropathy—immunologic and nonimmunologic factors. Ann Transplant. 2006;11(1):7-10.

Bao, et al. A novel accurate rapid ELISA for detection of urinary connective tissue growth factor, a biomarker of chronic allograft nephropathy. Transplant Proc. Sep. 2008;40(7):2361-4. doi: 10.1016/j.transproceed.2008.07.122.

Bolstad, et al. A comparison of normalization methods for high density oligonucleotide array data based on variance and bias. Bioinformatics. Jan. 22, 2003;19(2):185-93.

Brouard, et al. Identification of a peripheral blood transcriptional biomarker panel associated with operational renal allograft tolerance. Proc Natl Acad Sci U S A. Sep. 25, 2007;104(39):15448-53. Epub Sep. 14, 2007.

(56) References Cited

OTHER PUBLICATIONS

Brown, et al. Knowledge-based analysis of microarray gene expression data by using support vector machines. Proc Natl Acad Sci U S A. 2000, 97(1): 262-7.
Calne, et al. Cyclosporin A in patients receiving renal allografts from cadaver donors. Lancet. Dec. 23-30, 1978;2(8104-5):1323-7.
Chang, et al. Prediction of chronic allograft damage index of renal allografts using serum level of plasminogen activator inhibitor-1. Clin Transplant. Mar.-Apr. 2009;23(2):206-12. doi: 10.1111/j.1399-0012.2009.00970.x. Epub Feb. 11, 2009.
Chapman. Longitudinal analysis of chronic allograft nephropathy: clinicopathologic correlations. Kidney Int Suppl. 2005; (99): S108-12.
Chau, et al. Validation of analytic methods for biomarkers used in drug development. Clin Cancer Res. Oct. 1, 2008;14(19):5967-76. doi: 10.1158/1078-0432.CCR-07-4535.
Clarke, et al. Characterization of renal allograft rejection by urinary proteomic analysis, Ann Surg. May 2003;237(5):660-4; discussion 664-5.
Colvin, RB. Chronic allograft nephropathy. N Engl J Med. Dec. 11, 2003;349(24):2288-90.
Dabney, AR. Classification of microarrays to nearest centroids. Bioinfomatics. Nov. 15, 2005;21(22):4148-54. Epub Sep. 20, 2005.
De Mattos, et al. Nephrotoxicity of immunosuppressive drugs: long-term consequences and challenges for the future. Am J Kidney Dis. Feb. 2000;35(2):333-46.
De Serres, et al. Derivation and validation of a cytokine-based assay to screen for acute rejection in renal transplant recipients. Clin J Am Soc Nephrol. Jun. 2012;7(6):1018-25. doi: 10.2215/CJN.11051011. Epub Apr. 12, 2012.
Deng, et al. Noninvasive discrimination of rejection in cardiac allograft recipients using gene expression profiling. Am J Transplant. Jan. 2006;6(1):150-60.
Derisi, et al. Use of a cDNA microarray to analyse gene expression patterns in human cancer. Nat Genet. Dec. 1996;14(4):457-60.
Diaz-Uriarte, et al. Gene selection and classification of microarray data using random forest. BMC bioinformatics. 2006; 7: 3.
Dudoit. Comparison of discrimination methods for the classification of tumors using gene expression data. Journal of the American Statistical Association 97. 77-87, 2002.
Eisen, et al. Cluster analysis and display of genome-wide expression patterns. Proc Natl Acad Sci U S A. Dec. 8, 1998;95(25):14863-8.
Extended European Search Report and Search Opinion dated Jul. 7, 2017 for European Patent Application No. EP14841998.9.
Flechner, et al. De novo kidney transplantation without use of calcineurin inhibitors preserves renal structure and function at two years. Am J Transplant. Nov. 2004;4(11):1776-85.
Flechner, et al. Kidney transplant rejection and tissue injury by gene profiling of biopsies and peripheral blood lymphocytes. Am J Transplant. Sep. 2004;4(9):1475-89.
Flechner, et al. Kidney transplantation with sirolimus and mycophenolate mofetil-based immunosuppression: 5-year results of a randomized prospective trial compared to calcineurin inhibitor drugs. Transplantation. Apr. 15, 2007;83(7):883-92.
Gehrau, et al. Molecular pathways differentiate hepatitis C virus (HCV) recurrence from acute cellular rejection in HCV liver recipients. Mol. Med. 2011; 17(7-8):824-33.
Gibbs, et al. Quantitative detection of changes in cytokine gene expression in peripheral blood mononuclear cells correlates with and precedes acute rejection in renal transplant recipients. Transpl Immunol. Jun. 2005;14(2):99-108. Epub Mar. 29, 2005.
Gibson, et al. A novel method for real time quantitative RT-PCR. Genome Res. Oct. 1996;6(10):995-1001.
GP. GraphPad QuickCalcs: free statistical calculators. GraphPad Software. 2014. Accessed Dec. 9, 2014 http://www.graphpad.com/quickcalcs/index.cfm.
Guo, et al. Regularized linear discriminant analysis and its application microarrays. Biostatistics. Jan. 2007;8(1):86-100. Epub Apr. 7, 2006.

Halloran, et al. Microarray diagnosis of antibody-mediated rejection in kidney transplant biopsies: an international prospective study (INTERCOM). Am. J. Transplant. 2013, 13(11):2865-74.
Halloran, et al. Potential Impact of Microarray Diagnosis of T Cell-Mediated Rejection in Kidney Tranplants: The INTERCOM Study. Am. J. Transplants: 2013, 13(9):2352-63.
Hama, et al. Gene expression profiling of acute cellular rejection in rat liver transplantation using DNA microarrays. Liver Transpl. May 2009;15(5):509-21.
Harrell, et al. Multivariable prognostic models: issues in developing models, evaluating assumptions and adequacy, and measuring and reducing errors. Statistics in medicine. 1996;15(4): 361-87.
Harrell. Regression Modeling Strategies: with applications to linear models, logistic regression, and survivial anaysis. Springer, New York 2001.
Heid, et al. Real time quantitative PCR. Genome Res. Oct. 1996;6(10):986-94.
Heyne, et al. Urinary neutrophil gelatinase-associated lipocalin accurately detects acute allograft rejection among other causes of acute kidney injury in renal allograft recipients. Transplantation. Jun. 27, 2012;93(12):1252-7. doi: 10.1097/TP.0b013e31824fd892.
Holland, et al. Detection of specific polymerase chain reaction product by utilizing the 5'-3' exonuclease activity of Thermus aquaticus DNA polymerase. Proc Natl Acad Sci U S A. Aug. 15, 1991;88(16):7276-80.
Horwitz, et al. Detection of cardiac allograft rejection and response to immunosuppressive therapy with peripheral blood gene expression. Circulation. Dec. 21, 2004;110(25):3815-21. Epub Dec. 6, 2004.
Hsu, et al. A comparison of methods for multiclass support vector machines. IEEE Trans Neural Netw. 2002;13(2):415-25. doi: 10.1109/72.991427.
Huang, et al. Classification of malignant pediatric renal tumors by gene expression. Pediatr Blood Cancer. Jun. 2006;46(7):728-38.
Hymes, et al. Prevalence of clinical rejection after surveillance biopsies in pediatric renal transplants: does early subclinical rejection predispose to subsequent rejection episodes? Pediatr Transplant. Nov. 2009;13(7):823-6. doi: 10.1111/j.1399-3046.2009.01200.x. Epub Jun. 8, 2009.
International search report and written opinion dated May 24, 2011 for PCT/US2010/041598.
International search report and written opinion dated Oct. 19, 2015 for PCT Application No. US2015/032191.
International search report and written opinion dated Oct. 26, 2015 for PCT Application No. US2015/032195.
International search report and written opinion dated Nov. 4, 2015 for PCT Application No. US2015/032202.
International search report and written opinion dated Dec. 23, 2014 for PCT/US2014/054735.
Jevnikar, et al. Late kidney allograft loss: what we know about it, and what we can do about it. Clin J Am Soc Nephrol. Mar. 2008;3 Suppl 2:S56-67. doi: 10.2215/CJN.03040707.
Kurian, et al. Applying genomics to organ transplantation medicine in both discovery and validation of biomarkers. Int Immunopharmacol. Dec. 20, 2007;7(14):1948-60. Epub Aug. 9, 2007.
Kurian, et al. Biomarkers for early and late stage chronic allograft nephropathy by proteogenomic profiling of peripheral blood. PLoS One. Jul. 10, 2009;4(7):e6212. doi: 10.1371/journal.pone.0006212.
Kurian, et al. Molecular classifiers for acute kidney transplant rejection in peripheral blood by whole genome gene expression profiling. Am J Transplant. May 2014;14(5):1164-72. doi: 10.1111/ajt.12671. Epub Apr. 11, 2014.
Kurian. Genomics and proteomics in transplantation. Current opinion in organ transplantation. 2005, 10: 193-197.
Lachenbruch, et al. Biomarkers and surrogate endpoints in renal transplantation: present status and considerations for clinical trial design. Am J Transplant. Apr. 2004;4(4):451-7.
Lee, et al. Fit-for-purpose method development and validation for successful biomarker measurement. Pharm Res. Feb. 2006;23(2):312-28. Epub Jan. 12, 2006.
Lerut, et al. Acute rejection in non-compliant renal allograft recipients: a distinct morphology. Clin Transplant. 2007; 21(3): 344-51.

(56) References Cited

OTHER PUBLICATIONS

Levitsky; et al., "Clinical and plasma proteomic markers correlating with chronic kidney disease after liver transplantation. Am J Transplant. Sep. 2011; 11(9):1972-8. doi: 10.1111/j.1600-6143.2011.03669.x. Epub Jul. 27, 2011."

Li, et al. A peripheral blood diagnostic test for acute rejection in renal transplantation. Am J Transplant. Oct. 2012;12(10):2710-8. doi: 10.1111/j.1600-6143.2012.04253.x.

Lipshutz, et al. High density synthetic oligonucleotide arrays. Nat Genet. Jan. 1999;21(1 Suppl):20-4.

Liu, et al. A model for random sampling and estimation of relative protein abundance in shotgun proteomics. Anal Chem. Jul. 15, 2004;76(14):4193-201.

Liu, et al. Animal models of chronic liver diseases. Am. J. Physiol. Gastrointest Liver Physiol. 304:G449-68, 2013.

Livak, et al. Oligonucleotides with fluorescent dyes at opposite ends provide a quenched probe system useful for detecting PCR product and nucleic acid hybridization. PCR Methods Appl. Jun. 1995;4(6):357-62.

Lo, et al. Presence of donor-specific DNA in plasma of kidney and liver-transplant recipients. Lancet. May 2, 1998;351(9112):1329-30.

Lockhart, et al. Expression monitoring by hybridization to high-density oligonucleotide arrays. Nat Biotechnol. Dec. 1996;14(13):1675-80.

Maluf, et al. Molecular pathways involved in loss of kidney graft function with tubular atrophy and interstitial fibrosis. Mol Med. May-Jun. 2008;14(5-6):276-85. doi: 10.2119/2007-00111.Maluf.

Mannon, et al. Chronic rejection of mouse kidney allografts. Kidney Int. May 1999;55(5):1935-44.

Martínez-Llordella, et al. Using transcriptional profiling to develop a diagnostic test of operational tolerance in liver transplant recipients. J Clin Invest. Aug. 2008;118(8):2845-57.

Mas, et al. Establishing the molecular pathways involved in chronic allograft nephropathy for testing new noninvasive diagnostic markers. Transplantation. Feb. 27, 2007;83(4):448-57.

McCall, et al. Frozen robust multiarray analysis (fRMA). Biostatistics. Apr. 2010;11(2):242-53. doi: 10.1093/biostatistics/kxp059. Epub Jan. 22, 2010.

McCall, et al. Thawing Frozen Robust Multi-array Analysis (fRMA). BMC Bioinformatics. Sep. 16, 2011;12:369. doi: 10.1186/1471-2105-12-369.

Meier-Kriesche, et al. Lack of improvement in renal allograft survival despite a marked decrease in acute rejection rates over the most recent era. Am J Transplant. Mar. 2004;4(3):378-83.

Meier-Kriesche, et al. Survival improvement among patients with end-stage renal disease: trends over time for transplant recipients and wait-listed patients. J Am Soc Nephrol. Jun. 2001;12(6):1293-6.

Mengel, et al. Infiltrates in protocol biopsies from renal allografts. Am J Transplant. 2007; 7(2):356-65.

Mengel, et al. SWOT analysis of Banff: strengths, weaknesses, opportunities and threats of the international Banff consensus process and classification system for renal allograft pathology. Am J Transplant. Oct. 2007;7(10):2221-6.

Miao, et al. Estimating Harrell's Optimism on Predictive Indices Using Bootstrap Samples. SAS Global Forum, San Francisco; 2013.

Moreso, et al. Early subclinical rejection as a risk factor for late chronic humoral rejection. Transplantation. 2012; 93(1): 41-6.

Moreso, et al. Subclinical rejection associated with chronic allograft nephropathy in protocol biopsies as a risk factor for late graft loss. Am J Transplant. Apr. 2006;6(4):747-52.

Morrissey, et al. Factors contributing to acute rejection in renal transplantation: the role of noncompliance. Transplant Proc. 2005; 37(5): 2044-7.

Mueller, et al. Assessment of kidney organ quality and prediction of outcome at time of transplantation. 2011. Semin Immunopathol. vol. 33, pp. 185-199.

Nankivell, et al. Chronic allograft nephropathy: current concepts and future directions. Transplantation. Mar. 15, 2006;81(5):643-54.

Nankivell, et al. The natural history of chronic allograft nephropathy. N Engl J Med. Dec. 11, 2003;349(24):2326-33.

Nankivell. Subclinical renal allograft rejection and protocol biopsies: quo vadis? Nat Clin Pract Nephrol. 2008; 4(3): 134-5.

Nielsen, et al. Sequence-selective recognition of DNA by strand displacement with a thymine-substituted polyamide. Science, Dec. 6, 1991;254(5037):1497-500.

Oetting, et al. Urinary beta2-microglobulin is associated with acute renal allograft rejection. Am J Kidney Dis. May 2006;47(5):898-904.

Office Action dated Jan. 9, 2017 for U.S. Appl. No. 14/481,167.
Office action dated Mar. 12, 2015 for U.S. Appl. No. 13/261,130.
Office Action dated Jun. 15, 2016 for U.S. Appl. No. 14/481,167.
Office Action dated Aug. 18, 2017 for U.S. Appl. No. 14/481,167.
Office action dated Nov. 13, 2015 for U.S. Appl. No. 13/261,130.
Office Action dated Dec. 2, 2016 for U.S. Appl. No. 13/261,130.

PA. Power Atlas. 2007. Accessed Dec. 9, 2014 http://www.poweratlas.org/.

Pascual, et al. Chronic rejection and chronic cyclosporin toxicity in renal allografts. Immunol Today. Nov. 1998;19(11):514-9.

Pascual, et al. Strategies to improve long-term outcomes after renal transplantation. N Engl J Med. Feb. 21, 2002;346(8):580-90.

Pascual, et al. The clinical usefulness of the renal allograft biopsy in the cyclosporine era: a prospective study. Transplantation. Mar. 15, 1999;67(5):737-41.

Powell, et al. Managing renal transplant ischemia reperfusion injury: novel therapies in the pipeline. Clin Transplant. Jul.-Aug. 2013;27(4):484-91. doi: 10.1111/ctr.12121. Epub Apr. 25, 2013.

Racusen, et al. The Banff 97 working classification of renal allograft pathology. Kidney Int. Feb. 1999;55(2):713-23.

Rattanasiri, et al. The association between cytokine gene polymorphisms and graft rejection in liver transplantation: A systematic review and meta-analysis. Transpl Immunol. 2013 28(1):62-70.

Rödder, et al. Renal allografts with IF/TA display distinct expression profiles of metzincins and related genes. Am J Transplant. Mar. 2009;9(3):517-26.

Robin, et al. pROC: an open-source package for R and S+ to analyze and compare ROC curves. BMC Bioinformatics. Mar. 17, 2011;12:77. doi: 10.1186/1471-2105-12-77.

Rodder, et al. Renal allografts with IF/TA display distinct expression profiles of metzincins and related genes. American Journal of Transplantation, vol. 9, No. 3, pp. 517-526, Feb. 2009.

Rush, et al. Subclinical rejection—a potential surrogate marker for chronic rejection—may be diagnosed by protocol biopsy or urine spectroscopy. Ann Transplant. 2000; 5(2): 44-9.

Sabek, et al. Quantitative detection of T-cell activation markers by real-time PCR in renal transplant rejection and correlation with histopathologic evaluation. Transplantation. Sep. 15, 2002;74(5):701-7.

Sadygov, et al. Code developments to improve the efficiency of automated MS/MS spectra interpretation. J Proteome Res. May-Jun. 2002;1(3):211-5.

Salvadori, et al. Update on ischemia-reperfusion injury in kidney transplantation: Pathogenesis and treatment. World J Transplant. Jun. 24, 2015;5(2):52-67. doi: 10.5500/wjt.v5.i2.52.

Sarwal, et al. Molecular heterogeneity in acute renal allograft rejection identified by DNA microarray profiling. N Engl J Med. Jul. 10, 2003;349(2):125-38.

Schena, et al. Quantitative monitoring of gene expression patterns with a complementary DNA microarray. Science. Oct. 20, 1995;270(5235):467-70.

Scherer, et al. Transcriptome changes in renal allograft protocol biopsies at 3 months precede the onset of interstitial fibrosis/tubular atrophy (IF/TA) at 6 months. Nephrol Dial Transplant. Aug. 2009;24(8):2567-75. doi: 10.1093/ndt/gfp183. Epub Apr. 27, 2009.

Schuab, et al. Proteomic-based identification of cleaved urinary beta2-microglobulin as a potential marker for acute tubular injury in renal allografts. Am J Transplant. Apr. 2005;5(4 Pt 1):729-38.

Schwarz, at al. Risk factors for chronic allograft nephropathy after renal transplantation: a protocol biopsy study. Kidney Int. 2005; 67(1): 341-8.

(56) References Cited

OTHER PUBLICATIONS

Shapiro, et al. An analysis of early renal transplant protocol biopsies—the high incidence of subclinical tubulitis. Am J Transplant. May 2001;1(1):47-50.
Shen, et al. Eigengene-based linear discriminant model for tumor classification using gene expression microarray data. Bioinformatics. Nov. 1, 2006;22(21):2635-42. Epub Aug. 22, 2006.
Simon, et al. Serial peripheral blood perforin and granzyme B gene expression measurements for prediction of acute rejection in kidney graft recipients. Am J Transplant. Sep. 2003;3(9):1121-7.
Sis, et al. Endothelial gene expression in kidney transplants with alloantibody indicates antibody-mediated damage despite lack of C4d staining. Am J Transplant. Oct. 2009;9(10):2312-23. doi: 10.1111/j.1600-6143.2009.02761.x. Epub Jul. 22, 2009.
Solez, et al. Banff '05 Meeting Report: differential diagnosis of chronic allograft injury and elimination of chronic allograft nephropathy ('CAN'). Am J Transplant. Mar. 2007;7(3):518-26.
Solez, et al. Banff 07 classification of renal allograft pathology: updates and future directions. Am J Transplant. Apr. 2008;8(4):753-60. doi: 10.1111/j.1600-6143.2008.02189.x. Epub Feb. 19, 2008.
Spivey, et al. Gene expression profiling in acute allograft rejection: challenging the immunologic constant of rejection hypothesis. Translational Med. 2011 9:174.
Sreekumar, et al. Differential allograft gene expression in acute cellular rejection and recurrence of hepatitis C after liver transplantation. Liver Transpl. Sep. 2002; 8(9):814-21.
Tabb, et al. DTASelect and Contrast: tools for assembling and comparing protein identifications from shotgun proteomics. J Proteome Res. Jan.-Feb. 2002;1(1):21-6.
Thomas, et al. Chronic kidney disease and its complications. Prim Care. Jun. 2008;35(2):329-44, vii. doi: 10.1016/j.pop.2008.01.008. Review.
Tibshirani et al. Class prediction by nearest shrunken centroids with applications to DNA microarrays. Statistical Science 18(1):104-117 (2003).
Tibshirani et al. Diagnosis of multiple cancer types by shrunken centroids of gene expression. PNAS 99:6567-6572 (2002).
Tijssen, P. Chapter 3 of Laboratory Techniques in Biochemistry and Molecular Biology: Hybridization With Nucleic Acid Probes, Part I. Theory and Nucleic Acid Preparation, Elsevier, N.Y. 1993.
Tonelli, et al. Chronic kidney disease and mortality risk: a systematic review. J Am Soc Nephrol. Jul. 2006;17(7):2034-47. Epub May 31, 2006.
Tou, et al Pattern Recognition Principals, Addison-Wesley, Reading, Massachusetts. 1974.
U.S. Department of Health and Human Services. OPTN/SRTR Annual Report. Source: OPTN/SRTR Data as of May 4, 2009. http://www.ustransplant.org/annual_reports/current/509a_ki.htm.
Vasconcellos, et al. Cytotoxic lymphocyte gene expression in peripheral blood leukocytes correlates with rejecting renal allografts. Transplantation. Sep. 15, 1998;66(5):562-6.
Washburn et al. Large-scale analysis of the yeast proteome by multidimensional protein identification technology. Nat Biotechnol 19(3):242-247 (2001).
Wiebe, et al. Evolution and clinical pathologic correlations of de novo donor-specific HLA antibody post kidney transplant. Am J Transplant. May 2012;12(5):1157-67. doi: 10.1111/j.1600-6143. 2012.04013.x. Epub Mar. 19, 2012.
Woolf, SH. Screening for prostate cancer with prostate-specific antigen. An examination of the evidence. N Engl J Med. Nov. 23, 1995;333(21):1401-5.
Yates, et al. The aetiology and pathogenesis of chronic allograft nephropathy. Transpl Immunol. Nov. 2006;16(3-4):148-57. Epub Nov. 2, 2006.
Yilmaz, et al. Evaluating the accuracy of functional biomarkers for detecting histological changes in chronic allograft nephropathy. Transpl Int. Jul. 2007;20(7):608-15. Epub May 22, 2007.
Yilmaz, et al. Protocol core needle biospy and histologic Chronic Allograft Damage Index (CADI) as surrogate end point for long-term graft survival in multicenter studies. J Am Soc Nephrol. Mar. 2003;14(3):773-9.
Zhu, et al. Network-based support vector machine for classification of microarray samples. BMC Bioinformatics. Jan. 30, 2009;10 Suppl 1:S21. doi: 10.1186/1471-2105-10-S1-S21.
Co-pending U.S. Appl. No. 15/676,619, inventors Salomon; Daniel R. et al., filed Aug. 14, 2017.
Co-pending U.S. Appl. No. 15/676,711, inventors Salomon; Daniel R. et al., filed Aug. 14, 2017.
Co-pending U.S. Appl. No. 16/751,523, inventors Salomon; Daniel et al., filed Jan. 24, 2020.
Co-pending U.S. Appl. No. 16/803,337, filed Feb. 27, 2020.
Defamie et al. Gene expression profiling of human liver transplants identifies an early transcriptional signature associated with initial poor graft function. Am J Transplant. Jun. 2008;8(6):1221-36.
EP15795436.7 European Communication dated May 2, 2019.
European Search Report dated Jan. 2, 2018 for European Patent Application No. EP15795453.8.
European Search Report dated Apr. 4, 2017 for European Patent Application No. EP14841998.9.
European Search Report dated Apr. 5, 2018 for European Patent Application No. EP15795618.6.
European Search Report dated Dec. 19, 2017 for European Patent Application No. EP15795439.7.
Farid et al. Hepatocyte-derived microRNAs as serum biomarkers of hepatic injury and rejection after liver transplantation. Liver Transpl. Mar. 2012;18(3):290-7.
Goulet et al. Deficiency of 5-lipoxygenase accelerates renal allograft rejection in mice. J Immunol. Dec. 1, 2001;167(11):6631-6.
International Search Report and Written Opinion dated Jun. 8, 2017 for International PCT Patent Application No. PCT/US2017/016482.
Massoud et al. Noninvasive diagnosis of acute cellular rejection in liver transplant recipients: a proteomic signature validated by enzyme-linked immunosorbent assay. Liver Transpl. Jun. 2011;17(6):723-32.
Notice of Allowance dated May 2, 2017 for U.S. Appl. No. 13/261,130.
Office Action dated Nov. 1, 2017 for U.S. Appl. No. 15/358,390.
PCT/US2019/031850 International Search Report and Written Opinion dated Jul. 26, 2019.
Roedder et al. The kSORT assay to detect renal transplant patients at high risk for acute rejection: results of the multicenter AART study. PLoS Med. Nov. 11, 2014;11(11):e1001759.
U.S. Appl. No. 15/313,215 Office Action dated Jan. 7, 2019.
U.S. Appl. No. 15/313,215 Office Action dated Jul. 26, 2019.
U.S. Appl. No. 15/358,390 Notice of Allowance dated Jun. 10, 2019.
U.S. Appl. No. 15/358,390 Office Action dated Aug. 23, 2018.
U.S. Appl. No. 15/666,920 Office Action dated Aug. 27, 2019.
U.S. Appl. No. 15/898,513 Notice of Allowance dated Jul. 30, 2020.
U.S. Appl. No. 15/898,513 Office Action dated Aug. 13, 2019.
U.S. Appl. No. 15/898,513 Office Action dated Jan. 17, 2020.

\* cited by examiner

MOLECULAR SIGNATURES FOR DISTINGUISHING LIVER TRANSPLANT REJECTIONS OR INJURIES

CROSS-REFERENCE TO RELATED APPLICATIONS

This application claims the benefit of priority to U.S. application Ser. No. 14/481,167, filed Sep. 9, 2014; to International Application No. PCT/US2014/054735, filed Sep. 9, 2014; to U.S. Provisional Application No. 62/029,038, filed Jul. 25, 2014; to U.S. Provisional Application No. 62/001,889, filed May 22, 2014; to U.S. Provisional Application No. 62/001,902, filed May 22, 2014; and to U.S. Provisional Application No. 62/001,909, filed May 22, 2014, each of which is incorporated by reference herein in their entirety.

STATEMENT OF GOVERNMENT SUPPORT

This invention was made with government support under grant numbers AI063603, AI084146, and AI052349 awarded by the National Institutes of Health. The government has certain rights in the invention.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Liver transplantation (LT) is an important option for treating patients with advanced liver disease and cirrhosis. Currently, end-stage liver disease associated with hepatitis C virus (HCV) infection is the most common indication for LT. However, graft survival in hepatitis C virus (HCV)-infected recipients is worse than that in patients with other indications due to the high recurrence rate of HCV infection. Other than HCV recurrence (HCV-R), acute rejection (AR) after LT is also common and remains an important cause of morbidity and late graft failure in the liver transplant recipient (LTR). Despite continuous improvements in immunosuppressive therapy, AR still occurs in 25% to 40% of recipients and results in graft loss in some patients.

AR and HCV-R can demonstrate similar clinical features, such as worsening liver function tests, and the histomorphology of liver biopsy samples can reveal overlapping features in the 2 entities. On the other hand, the treatments of the 2 complications are usually quite different. HCV-positive recipients who develop rejection need increased and/or different immunosuppression to blunt the autoimmune response, while reduced immunosuppression, often in conjunction with antiviral therapies, is called for patients with HCV-R. Organ biopsy results (e.g., liver biopsy results) can also be inaccurate, particularly if the area biopsied is not representative of the health of the organ as a whole (e.g., as a result of sampling error). There can be significant differences between individual observers when they read the same biopsies independently and these discrepancies are particularly an issue for complex histologies that can be challenging for clinicians. In addition, the early detection of rejection of a transplant organ may require serial monitoring by obtaining multiple biopsies, thereby multiplying the risks to the patients, as well as the associated costs. Transplant rejection is a marker of ineffective immunosuppression and ultimately if it cannot be resolved, a failure of the chosen therapy. Thus, an inaccurate diagnosis of the underlying cause of transplant rejection is important for remedying graft dysfunction and long term patient survival.

Currently, there are no non-invasive and reliable assays capable of accurately differentiating between the major causes of liver transplant rejection. The present invention addresses this and other unfulfilled needs in the art.

SUMMARY OF THE INVENTION

In one aspect, the invention provides methods of detecting, prognosing, diagnosing or monitoring a liver transplant rejection or injury, or lack thereof in a subject. The methods may comprise (a) obtaining nucleic acids of interest, and then (b) detecting or determining expression levels in a subject of at least 5 genes selected from the genes listed in Table 4, Table 5, or Table 6 herein; and (c) detecting, prognosing, diagnosing or monitoring from the expression levels of the genes detected or determined in step (b) an ongoing transplant rejection or injury, or lack thereof in the subject. In some cases, the method further comprises contacting the nucleic acids of interest with probes, wherein the probes are specific for the at least five genes selected in step (b). In some cases, the method further comprises sequencing the nucleic acids of interests, such as by Next Generation Sequencing. Typically, the subject to be examined with the methods can have acute rejection (AR), acute dysfunction no rejection (ADNR), hepatitis C virus recurrence (HCV), hepatitis C virus recurrence plus acute rejection (HCV+AR), or a well-functioning normal transplant (TX). In some of the methods, for each of the at least five genes, step (c) involves comparing the expression level of the gene in the subject to one or more reference expression levels of the gene associated with AR, ADNR, HCV, HCV+AR, or TX. In some methods, step (c) further includes, for each of the at least five genes, assigning the expression level of the gene in the subject a value or other designation providing an indication whether the subject has AR, ADNR, HCV, HCV+AR, or TX. In some of these methods, the expression level of each of the at least five genes is assigned a value on a normalized scale of values associated with a range of expression levels in liver transplant patients with AR, ADNR, HCV, HCV+AR, or TX. In some of the methods, the expression level of each of the at least five genes is assigned a value or other designation providing an indication that the subject has or is at risk of AR, ADNR, HCV, or HCV+AR, has well-functioning normal transplant, or that the expression level is uninformative. In some methods, step (c) further includes combining the values or designations for each of the genes to provide a combined value or designation providing an indication whether the subject has or is at risk of AR, ADNR, HCV, or HCV+AR, or has well-functioning normal transplant (TX).

The methods of the invention can be repeated at different times on a given subject. In some embodiments, the subject can be one who is receiving a drug, and a change in the combined value or designation over time provides an indication of the effectiveness of the drug. In various embodiments, the subject can be one who has undergone a liver transplant within 1 month, 3 months, 1 year, 2 years, 3 years or 5 years of performing step (a). In some methods, step (b) can be performed on at least 10, 20, 40, or 100 genes. Some methods additionally include changing the treatment regime of the patient responsive to the prognosing, diagnosing or monitoring step. In some methods, the subject has received a drug before performing the methods, and the change comprises administering an additional drug, administering a higher dose of the same drug, administering a lower dose of the same drug or stopping administering the same drug. In various embodiments of the invention, expression levels of the genes are determined at the mRNA level or at the protein level. In some methods, step (c) can be performed by a computer.

Some methods of the invention are directed to prognosing or diagnosing patients who have either AR, or HCV, or HCV+AR. In these methods, the at least 5 genes are selected from the genes listed in at least one of Tables 4, 5, and 6. In some of these methods, step (a) is performed on a blood sample, a urine sample or a biopsy sample of the subject. In some of these methods, the blood sample comprises whole blood, peripheral blood, serum, plasma, PBLs, PBMCs, T cells, CD4 T cells CD8 T cells, or macrophages. Some other methods of the invention are directed to prognosing or diagnosing patients who have AR, ADNR, or TX. In these methods, the at least 5 genes are selected from the genes listed in at least one of Tables 4, 5, and 6. Some of these methods employ a blood sample of the subject and utilize at least 5 genes selected from the genes listed in Table 4. Some other methods employ a biopsy sample of the subject and utilize at least 5 genes selected from the genes listed in Table 6.

In another aspect, the invention provide arrays which contain a support or supports bearing a plurality of nucleic acid probes complementary to a plurality of mRNAs fewer than 5000 in number. The plurality of mRNAs include mRNAs expressed by at least five genes selected from at least one of Tables 4, 5, and 6. In some embodiments, the plurality of mRNAs are fewer than 1000 or fewer than 100 in number. On some arrays, the plurality of nucleic acid probes are attached to a planar support or to beads. In a related aspect, the invention provides arrays which contain a support or supports bearing a plurality of ligands that specifically bind to a plurality of proteins fewer than 5000 in number. The plurality of proteins includes at least five proteins encoded by genes selected from at least one of Tables 4, 5, and 6. On some of these arrays, the plurality of proteins are fewer than 1000 or fewer than 100 in number. On some of the arrays, the plurality of ligands are attached to a planar support or to beads. In some embodiments, the ligands are different antibodies, and the different antibodies bind to different proteins of the plurality of proteins.

In another aspect, the invention provides methods of expression analysis. The methods entail determining expression levels of up to 5000 genes in a sample from a subject having a liver transplant. Typically, the genes include at least 5 genes selected from at least one of Tables 4, 5, and 6. In some methods, the expression levels of up to 100 or 1000 genes are determined. In various embodiments, the gene expression levels can be determined at the mRNA level or at the protein level. In some of these methods, the expression levels are determined by quantitative PCR, hybridization to an array or sequencing (e.g., RNA sequencing, DNA sequencing).

In still another aspect, the invention provides methods of screening a compound for activity in inhibiting or treating a liver transplant rejection or injury. These methods entail (a) administering the compound to a subject having or at risk of developing a liver transplant rejection; (b) determining or detecting expression levels of at least five genes in the subject selected from Tables 4, 5, and 6 and species variants thereof before and after administering the compound to the subject, and (c) determining whether the compound has activity in inhibiting or treating the liver transplant rejection from a change in expression levels of the genes after administering the compound. In some of these methods, the liver transplant rejection or injury is AR, ADNR, HCV, or HCV+AR. In some methods, step (c) involves, for each of the at least five changes, assigning a value or designation depending on whether the change in the expression level of the gene relative to one or more reference levels indicating presence or absence of the liver transplant rejection. Some of these methods can further include determining a combined value or designation for the at least five genes from the values or designations determined for each gene. In some preferred embodiments, the subject is human or a nonhuman animal model of the liver transplant rejection.

In another aspect, the methods disclosed herein have an error rate of less than about 40%. In some embodiments, the method has an error rate of less than about 40%, 35%, 30%, 25%, 20%, 15%, 10%, 5%, 3%, 2%, or 1%. For example, the method has an error rate of less than about 10%. In some embodiments, the methods disclosed herein have an accuracy of at least about 60%, 65%, 70%, 75%, 80%, 85%, 90%, 95%, or 99%. For example, the method has an accuracy of at least about 70%. In some embodiments, the methods disclosed herein have a sensitivity of at least about 60%, 65%, 70%, 75%, 80%, 85%, 90%, 95%, or 99%. For example, the method has a sensitivity of at least about 80%. In some embodiments, the methods disclosed herein have a positive predictive value of at least about 60%, 65%, 70%, 75%, 80%, 85%, 90%, 95%, or 99%. In some embodiments, the methods disclosed herein have a negative predictive value of at least about 60%, 65%, 70%, 75%, 80%, 85%, 90%, 95%, or 99%.

In some embodiments, the gene expression products described herein are RNA (e.g., mRNA). In some embodiments, the gene expression products are polypeptides. In some embodiments, the gene expression products are DNA complements of RNA expression products from the transplant recipient.

In an embodiment, the algorithm described herein is a trained algorithm. In another embodiment, the trained algorithm is trained with gene expression data from biological samples from at least three different cohorts. In another embodiment, the trained algorithm comprises a linear classifier. In another embodiment, the linear classifier comprises one or more linear discriminant analysis, Fisher's linear discriminant, Naïve Bayes classifier, Logistic regression, Perceptron, Support vector machine (SVM) or a combination thereof. In another embodiment, the algorithm comprises a Diagonal Linear Discriminant Analysis (DLDA) algorithm. In another embodiment, the algorithm comprises a Nearest Centroid algorithm. In another embodiment, the algorithm comprises a Random Forest algorithm or statistical bootstrapping. In another embodiment, the algorithm comprises a Prediction Analysis of Microarrays (PAM) algorithm. In another embodiment, the algorithm is not validated by a cohort-based analysis of an entire cohort. In another embodiment, the algorithm is validated by a combined analysis with an unknown phenotype and a subset of a cohort with known phenotypes.

In another aspect, the sample is a blood sample or is derived from a blood sample. In another embodiment, the blood sample is a peripheral blood sample. In another embodiment, the blood sample is a whole blood sample. In another embodiment, the sample does not comprise tissue from a biopsy of a transplanted organ of the transplant recipient. In another embodiment, the sample is not derived from tissue from a biopsy of a transplanted organ of the transplant recipient.

In another aspect, the assay is a microarray, SAGE, blotting, RT-PCR, sequencing and/or quantitative PCR assay. In another embodiment, the assay is a microarray assay. In another embodiment, the microarray assay comprises the use of an Affymetrix Human Genome U133 Plus 2.0 GeneChip. In another embodiment, the mircroarray uses the Hu133 Plus 2.0 cartridge arrays plates. In another embodiment, the microarray uses the HT HG-U133+PM array plates. In another embodiment, determining the assay is a sequencing assay. In another embodiment, the assay is a RNA sequencing assay. A further understanding of the nature and advantages of the present invention may be realized by reference to the remaining portions of the specification and claims.

DETAILED DESCRIPTION

The invention is predicated in part on the identification of molecular classifiers that can distinguish major causes of liver transplant rejections and injuries. As detailed herein, the molecular classifiers, identified both blood and biopsy tissues of liver transplant patients, allows determination of Acute Rejection (AR) or Hepatitis C Virus Recurrence (HCV-R) even when both are present, and other causes (Acute Dysfunction No Rejection; ADNR) with high predictive accuracies.

The mRNA signatures are useful to enhance the specificity of diagnosis, particularly in managing patients with contrasting etiologies (e.g., AR vs. HCV-R) which need to be treated differently. The problem of diagnosing ADNR in liver transplantation leads to unnecessary biopsies and expensive imaging to identify potential causes. The molecular biomarkers of the invention can also allow long term immune monitoring of adequate maintenance immunosuppression and guide therapy decisions during drug reduction/withdrawal.

The invention provides diagnostic assays based on the blood profiles of liver transplant rejections. Such assays are minimally invasive and do not have the risks, costs and logistics involved in a liver biopsy. Assays based on the biopsy profiles of transplant rejections are also provided in the invention. They can reveal the molecular basis of liver rejection and the impact of HCV infection that are currently very difficult to discern with classic light histology without very specialized liver pathology expertise that is not generally available.

Figure 1:
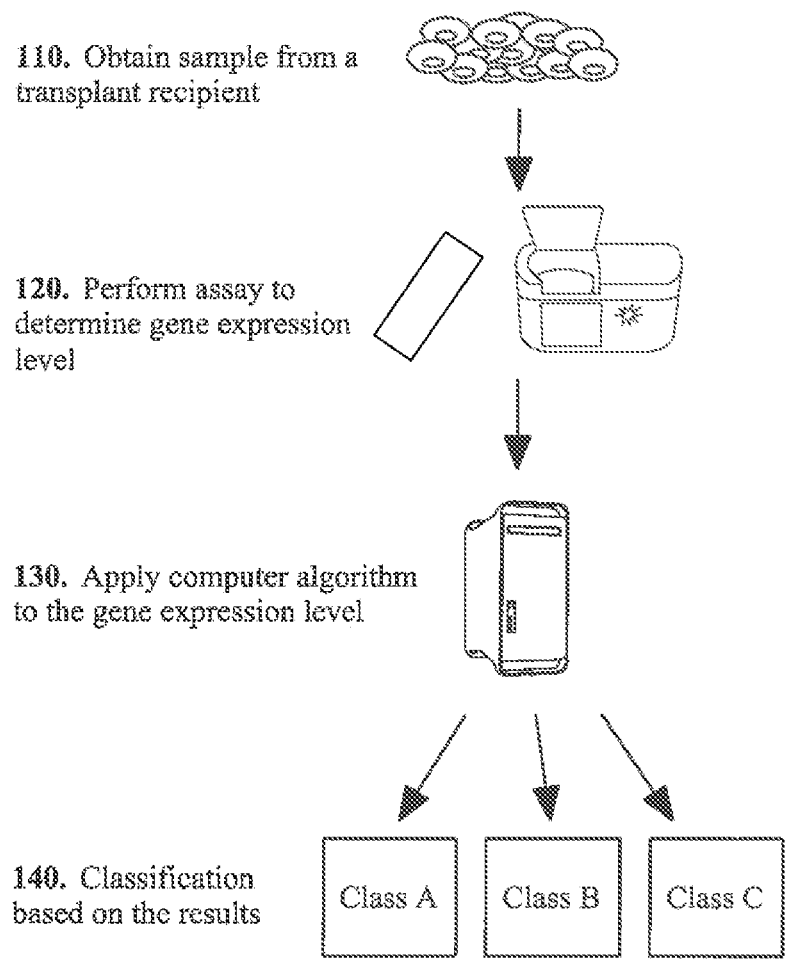
FIG. 1 shows a schematic overview of certain methods in the disclosure.

An overview of certain methods in the disclosure is provided in FIG. 1. In some instances, a method comprises obtaining a sample from a liver transplant recipient in a minimally invasive manner (110), such as via a blood draw. The sample may comprise gene expression products (e.g., polypeptides, RNA, mRNA isolated from within cells or a cell-free source) associated with the status of the transplant (e.g., transplant rejection.). In some instances, the method may involve reverse-transcribing RNA within the sample to obtain cDNA that can be analyzed using the methods described herein. The method may also comprise assaying the level of the gene expression products (or the corresponding DNA) using methods such as microarray or sequencing technology (120). The method may also comprise applying an algorithm to the assayed gene expression levels (130) in order to detect liver transplant rejection. After detection of the presence or absence of liver transplant rejection, a treatment decision may be made. In some cases, the treatment decision may be that the transplant recipient should be treated more aggressively to mitigate the risk of acute rejection. In some cases, the treatment decision may be to reduce an existing treatment regimen, particularly if liver transplant rejection is not detected. In the event that no liver transplant rejection is detected, the treatment decision may involve a decision to forego or delay obtaining a liver biopsy from the patient.

The following sections provide guidance for carrying out the methods of the invention.

I. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Illustrated Dictionary of Immunology*, Cruse (Ed.), CRC Pr I LIc (2$^{nd}$ ed., 2002); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4$^{th}$ ed., 2000). In addition, the following definitions are provided to assist the reader in the practice of the invention.

Transplantation is the transfer of tissues, cells or an organ from a donor into a recipient. If the donor and recipient as the same person, the graft is referred to as an autograft and as is usually the case between different individuals of the same species an allograft. Transfer of tissue between species is referred to as a xenograft.

A biopsy is a specimen obtained from a living patient for diagnostic evaluation. Liver biopsies can be obtained with a needle.

An average value can refer to any of a mean, median or mode.

A gene expression level is associated with a particular phenotype e.g., presence of a specific liver transplant rejection if the gene is differentially expressed in a patient having the phenotype relative to a patient lacking the phenotype to a statistically significant extent. Unless otherwise apparent from the context a gene expression level can be measured at the mRNA and/or protein level.

A target nucleic acids is a nucleic acid (often derived from a biological sample), to which a polynucleotide probe is designed to specifically hybridize. The probe can detect presence, absence and/or amount of the target. The term can refer to the specific subsequence of a larger nucleic acid to which the probe is directed or to the overall sequence (e.g., cDNA or mRNA) whose expression level is to be detected. The term can also refer to a nucleic acid that is analyzed by a method, including sequencing, PCR, or other method known in the art.

The term subject or patient can include human or non-human animals. Thus, the methods and described herein are applicable to both human and veterinary disease and animal models. Preferred subjects are "patients," i.e., living humans that are receiving medical care for a disease or condition. This includes persons with no defined illness who are being investigated for signs of pathology. The term subject or patient can include transplant recipients or donors or healthy subjects. The methods can be particularly useful for human subjects who have undergone a liver transplant although they can also be used for subjects who have gone other types of transplant (e.g., heart, kidney, lung, stem cell, etc.). The subjects may be mammals or non-mammals. Preferably, the subject is a human but in some cases, the subject is a non-human mammal, such as a non-human primate (e.g., ape, monkey, chimpanzee), cat, dog, rabbit, goat, horse, cow, pig, rodent, mouse, SCID mouse, rat, guinea pig, or sheep. The subject may be male or female; the subject may be and, in some cases, the subject may be an infant, child, adolescent, teenager or adult. In some cases, the methods provided herein are used on a subject who has not yet received a transplant, such as a subject who is awaiting a tissue or organ transplant. In other cases, the subject is a transplant donor. In some cases, the subject has not received a transplant and is not expected to receive such transplant. In some cases, the subject may be a subject who is suffering from diseases requiring monitoring of certain organs for potential failure or dysfunction. In some cases, the subject may be a healthy subject.

Often, the subject is a patient or other individual undergoing a treatment regimen, or being evaluated for a treatment regimen (e.g., immunosuppressive therapy). However, in some instances, the subject is not undergoing a treatment regimen. A feature of the graft tolerant phenotype detected or identified by the subject methods is that it is a phenotype which occurs without immunosuppressive therapy, e.g., it is present in a subject that is not receiving immunosuppressive therapy.

A transplant recipient may be a recipient of a solid organ or a fragment of a solid organ such as a kidney. Preferably, the transplant recipient is a liver transplant or allograft recipient. In some instances, the transplant recipient may be a recipient of a tissue or cell. In some particular examples, the transplanted liver may be a liver differentiated in vitro from pluripotent stem cell(s) (e.g., induced pluripotent stem cells or embryonic stem cells).

The donor organ, tissue, or cells may be derived from a subject who has certain similarities or compatibilities with the recipient subject. For example, the donor organ, tissue, or cells may be derived from a donor subject who is age-matched, ethnicity-matched, gender-matched, blood-type compatible, or HLA-type compatible with the recipient subject.

In various embodiments, the subjects suitable for methods of the invention are patients who have undergone an organ transplant within 6 hours, 12 hours, 1 day, 2 days, 3 days, 4 days, 5 days, 10 days, 15 days, 20 days, 25 days, 1 month, 2 months, 3 months, 4 months, 5 months, 7 months, 9 months, 11 months, 1 year, 2 years, 4 years, 5 years, 10 years, 15 years, 20 years or longer of prior to receiving a classification obtained by the methods disclosed herein, such as detection of liver transplant rejection.

Diagnosis refers to methods of estimating or determining whether or not a patient is suffering from a given disease or condition or severity of the condition. Diagnosis does not require ability to determine the presence or absence of a particular disease with 100% accuracy, or even that a given course or outcome is more likely to occur than not. Instead, the "diagnosis" refers to an increased probability that a certain disease or condition is present in the subject compared to the probability before the diagnostic test was performed. Similarly, a prognosis signals an increased probability that a given course or outcome will occur in a patient relative to the probability before the prognostic test.

A probe or polynucleotide probe is a nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." A probe can include natural (e.g., A, G, C, U, or T) or modified bases (e.g., 7-deazaguanosine, inosine.). A probe can be an oligonucleotide which is a single-stranded DNA. Polynucleotide probes can be synthesized or produced from naturally occurring polynucleotides. In addition, the bases in a probe can be joined by a linkage other than a phosphodiester bond, so long as it does not interfere with hybridization. Thus, probes can include, for example, peptide nucleic acids in which the constituent bases are joined by peptide bonds rather than phosphodiester linkages (see, e.g., Nielsen et al., *Science* 254, 1497-1500 (1991)). Some probes can have leading and/or trailing sequences of noncomplementarity flanking a region of complementarity.

A perfectly matched probe has a sequence perfectly complementary to a particular target sequence. The probe is typically perfectly complementary to a portion (subsequence) of a target sequence. The term "mismatch probe" refer to probes whose sequence is deliberately selected not to be perfectly complementary to a particular target sequence.

The term "isolated," "purified" or "substantially pure" means an object species (e.g., a nucleic acid sequence described herein or a polypeptide encoded thereby) has been at least partially separated from the components with which it is naturally associated.

Differential expression refers to a statistically significant difference in expression levels of a gene between two populations of samples (e.g., samples with and without a specific transplant rejection). The expression levels can differ for example by at least a factor of >1, 1.5 or 2 between such populations of samples. Differential expression includes genes that are expressed in one population and are not expressed (at least at detectable levels) in the other populations. Unique expression, usually associated with proteomic and next-generation sequencing technologies, refers to detectable expression in one population and undetectable expression (i.e., insignificantly different from background) in the other population using the same technique (e.g., as in the present example for detection).

Control populations for comparison with populations undergoing a liver transplant rejection or injury are usually referred to as being without acute rejection and have a well-functioning graft. In some embodiments, such a control population also means subjects without ADNR and/or HCV infection.

Hybridization reactions are preferably performed under stringent conditions in which probes or primers hybridize to their intended target with which they have perfect complementarity and not to or at least to a reduced extent to other targets. An example of stringent hybridization conditions are hybridization in 6×sodium chloride/sodium citrate (SSC) at about 45° C., followed by one or more washes in 0.2×SSC, 0.1% SDS at 50° C., 55° C., 60° C., and even more or 65° C.

Statistical significance means $p<0.05$, $<0.01$, $<0.001$, or even $<0.005$ level.

II. Genes in Profiles

The inventors identified differentially expressed genes that can distinguish different graft injury or condition in liver transplant patients. Specifically, Table 4 lists 263 differentially expressed genes in blood samples based on a 3-way comparison of acute rejection (AR) vs. acute dysfunction no rejection (ADNR) vs. transplant excellent (TX). The columns in the table have the following meanings: column 1 is a number assigned to a gene, column 2 is an Affymetrix number indicating a set of probes suitable for measuring expression of the gene, column 3 is a gene name (recognized names of HUGO or similar bodies are used when available), column 4 is a further description of the gene, column 5 is a measure of the statistical significance of change in gene expression between the above patient populations, and columns 6-8 respectively show mean expression levels of ADNR, AR, and TX patients. As detailed in the Examples herein, these probesets and corresponding genes are able to distinguish the phenotypes of the above three different types of liver transplants with very high predictive accuracy. Table 5 provides similar information for 147 genes that show differential expression in blood samples from liver transplant patients who have acute rejection (AR), hepatitis C virus recurrence (HCV-R), or hepatitis C virus recurrence and acute rejection (HCV+AR). The inventors demonstrated that these genes can be used to accurately distinguish the three noted phenotypes of liver transplant. In addition to expression profiles obtained blood samples, the inventors also identified differentially expressed genes in liver biopsies from transplant patients with different phenotypes. Table 6 lists 320 differentially expressed genes in liver biopsies which can be used to predict acute rejection (AR), acute dysfunction no rejection (ADNR), or transplant excellent (TX) in the patients.

The genes referred to in the above tables are human genes. In some methods, species variants or homologs of these genes are used in a non-human animal model. Species variants are the genes in different species having greatest sequence identity and similarity in functional properties to one another. Many species variants of the above human genes are listed in the Swiss-Prot database.

To identify differentially expressed genes, raw gene expression levels are comparable between different genes in the same sample but not necessarily between different samples. As noted above, values given for gene expression levels can be normalized so that values for particular genes are comparable within and between the populations being analyzed. The normalization eliminates or at least reduces to acceptable levels any sample to sample differences arising from factors other than a specific type of liver transplant rejection or injury (e.g. differences in overall transcription levels of patients due to general state of health and differences in sample preparation or nucleic acid amplification between samples). The normalization effectively applies a correction factor to the measured expression levels from a given array such that a profile of many expression levels in the array are the same between different patient samples. Software for normalizing overall expression patterns between different samples is both commercially and publically available (e.g., Partek Genomics Suite from Partek, XRAY from Biotique Systems or BRB ArrayTools from the National Cancer Institute). After applying appropriate normalizing factors to the measured expression value of a particular gene in different samples, an average or mean value of the expression level is determined for the samples in a population. The average or mean values between different populations are then compared to determine whether expression level has changed significantly between the populations. The changes in expression level indicated for a given gene represent the relative expression level of that gene in samples from a population of individuals with a defined condition (e.g., transplant patients with acute rejection) relative to samples from a control population (liver transplant patients not undergoing rejection). Similar principles apply in normalizing gene expression levels at the mRNA and protein levels. Comparisons between populations are made at the same level (e.g., mRNA levels in one population are compared with mRNA levels in another population or protein levels in one population with protein levels in another population).

III. Subject Populations

The methods described herein are particularly useful on human subjects who have undergone a liver transplant although can also be used on subjects who have undergone other types of transplant (e.g., heart, kidney, lungs, stem cell) or on non-humans who have undergone liver or other transplant. The patients may have or are at risk of developing any of the phenotypes of graft rejection or injuries described herein. These include patients with acute rejection (AR), patients with acute dysfunction no rejection (ADNR), patients with hepatitis C virus recurrence (HCV-R), patients with hepatitis C virus recurrence and acute rejection (HCV+ AR), and patients who have normal functional graft or transplant excellent (TX). Patients with phenotypes of graft rejection or injuries described herein can be diagnosed through biposies that are taken at a fixed time after transplantation (e.g., protocol biopsies or serial monitoring biopsies) which are not driven by clinical indications but rather by standards of care. The biopsies may be analyzed histologically in order to detect the liver transplant rejection. A failure to recognize, diagnose and treat any of the phenotypes of graft rejection or injuries before significant tissue injury has occurred and the transplant shows clinical signs of dysfunction could be a major cause of irreversible organ damage. Moreover, a failure to recognize chronic, subclinical immune-mediated organ damage and a failure to make appropriate changes in immunosuppressive therapy to restore a state of effective immunosuppression in that patient could contribute to late organ transplant failure. The methods disclosed herein can reduce or eliminate these and other problems associated with transplant rejection or failure. In some methods, the subject population contains liver transplant patients who have acute rejection (AR), hepatitis C virus recurrence (HCV-R), or hepatitis C virus recurrence and acute rejection (HCV+AR). In some other patients, the subject population contains liver transplant patients who have or are at risk of having acute rejection (AR), have or are at risk of having acute dysfunction no rejection (ADNR), or are transplant excellent (TX).

Acute rejection (AR) or clinical acute rejection may occur when transplanted tissue is rejected by the recipient's immune system, which damages or destroys the transplanted tissue unless immunosuppression is achieved. T-cells, B-cells and other immune cells as well as possibly antibodies of the recipient may cause the graft cells to lyse or produce cytokines that recruit other inflammatory cells, eventually causing necrosis of allograft tissue. In some instances, AR may be diagnosed by a biopsy of the transplanted organ. The treatment of AR may include using immunosuppressive agents, corticosteroids, polyclonal and monoclonal antibodies, engineered and naturally occurring biological molecules, and antiproliferatives. AR more frequently occurs in the first three to 12 months after transplantation but there is a continued risk and incidence of AR for the first five years post transplant and whenever a patient's immunosuppression becomes inadequate for any reason for the life of the transplant.

The methods herein may also be used to distinguish between a liver transplant patient with AR and a normally functioning liver transplant. Typically, when the patient does not exhibit symptoms or test results of organ dysfunction or rejection, the transplant is considered a normal functioning transplant (TX: Transplant eXcellent). An unhealthy transplant recipient may exhibit signs of organ dysfunction and/or rejection.

Regardless of the specific subject population, gene expression levels in such subjects can be measured, for example, within, one month, three months, six months, one year, two years, five years or ten years after a liver transplant. In some methods, gene expression levels are determined at regular intervals, e.g., every 3 months, 6 months or every year post-transplant, either indefinitely, or until evidence of graft rejection or injury is observed, in which case the frequency of monitoring is sometimes increased. In some methods, baseline values of expression levels are determined in a subject before a liver transplant in combination with determining expression levels at one or more time points thereafter. In other methods, a measurement is initiated responsive to some other indication of potential liver impairment, such as a rise in levels of creatinine or Blood Urea Nitrogen (BUN) or a decrease in glomerular filtration rate. Similar methods can be practiced in non-human species, in which cases, the expression levels measured are the species equivalent of the human genes referenced above.

IV. Methods of Measuring Profiles

Samples

Methods of the invention can utilize either a blood sample or a biopsy sample from the patient. In some preferred methods, a blood sample is used, which can be peripheral whole blood or fractions thereof, such as plasma, or lymphocytes. In some other methods, a liver biopsy is obtained from the patient for expression profile analysis. Other samples that may be employed in measuring gene expression profiles include urine, feces, and saliva. The samples are typically isolated from a subject and not returned to the subject. The analytes of interests in the samples can be analyzed with or without further processing of the sample, such as purification and amplification. For prognosis or diagnosis of AR in patients as opposed to patients with ANDR or patients without rejection (TX), the profiles can contain genes selected from Table 4. In these methods, a blood sample is preferably used. However, a sample may be any material containing tissues, cells, nucleic acids, genes, gene fragments, expression products, polypeptides, exosomes, gene expression products, or gene expression product fragments of a subject to be tested. In some cases, the sample is from a single patient. In some cases, the method comprises analyzing multiple samples at once, e.g., via massively parallel sequencing.

The sample can be blood. In some cases, the sample comprises whole blood, plasma, peripheral blood lymphocytes (PBLs), peripheral blood mononuclear cells (PBMCs), serum, T cells, B Cells, CD3 cells, CD8 cells, CD4 cells, or other immune cells.

The methods, kits, and systems disclosed herein may comprise specifically detecting, profiling, or quantitating molecules (e.g., nucleic acids, DNA, RNA, polypeptides, etc.) that are within the biological samples. In some instances, genomic expression products, including RNA, or polypeptides, may be isolated from the biological samples. In some cases, nucleic acids, DNA, RNA, polypeptides may be isolated from a cell-free source. In some cases, nucleic acids, DNA, RNA, polypeptides may be isolated from cells derived from the transplant recipient.

The sample may be obtained using any method known to the art that can provide a sample suitable for the analytical methods described herein. The sample may be obtained by a non-invasive method such as a throat swab, buccal swab, bronchial lavage, urine collection, scraping of the skin or cervix, swabbing of the cheek, saliva collection, feces collection, menses collection, or semen collection.

The sample may be obtained by a minimally-invasive method such as a blood draw. The sample may be obtained by venipuncture. In other instances, the sample is obtained by an invasive procedure including but not limited to: biopsy, alveolar or pulmonary lavage, or needle aspiration. The method of biopsy may include surgical biopsy, incisional biopsy, excisional biopsy, punch biopsy, shave biopsy, or skin biopsy. The sample may be formalin fixed sections. The method of needle aspiration may further include fine needle aspiration, core needle biopsy, vacuum assisted biopsy, or large core biopsy. In some embodiments, multiple samples may be obtained by the methods herein to ensure a sufficient amount of biological material. In some instances, the sample is not obtained by biopsy. In some instances, the sample is not a liver biopsy.

Expression Profiles

Some other methods of the invention are directed to prognosis or diagnosis to distinguish patients who have or are at risk of developing AR, patients who have or are at risk of having HCV recurrence (HCV), and patients who have or are at risk of having HCV plus AR, and patients without rejection (TX). For these methods, the genes in the expression profiles to be measure can be selected from Table 5 or Table 6. In some of these methods, a blood sample is preferably used. Such methods preferably utilize an expression profile of genes selected from Table 5. In some other methods, a liver biopsy sample is preferably used. Such methods preferably utilize an expression profile of genes selected from Table 6.

Expression profiles are preferably measured at the nucleic acid level, meaning that levels of mRNA or nucleic acid derived therefrom (e.g., cDNA or cRNA). An expression profile refers to the expression levels of a plurality of genes in a sample. A nucleic acid derived from mRNA means a nucleic acid synthesized using mRNA as a template. Methods of isolation and amplification of mRNA are well known in the art, e.g., as described in WO 97/10365, WO 97/27317, Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993). If mRNA or a nucleic acid therefrom is amplified, the amplification is performed under conditions that approximately preserve the relative proportions of mRNA in the original samples, such that the levels of the amplified nucleic acids can be used to establish phenotypic associations representative of the mRNAs.

A variety of approaches are available for determining mRNA levels including probe arrays and quantitative PCR. A number of distinct array formats are available. Some arrays, such as an Affymetrix HG-U133 PM microarray or other Affymetrix GeneChip® array, have different probes occupying discrete known areas of a contiguous support. Exemplary microarrays include but are not limited to the Affymetrix Human Genome U133 Plus 2.0 GeneChip or the HT HG-U133+PM Array Plate.

Other arrays, such as arrays from Illumina, have different probes attached to different particles or beads. In such arrays, the identity of which probe is attached to which particle or beads is usually determinable from an encoding system. The probes can be oligonucleotides. In such case, typically several match probes are included with perfect complementarity to a given target mRNA together, optionally together with mismatch probes differing from the match probes are a known number of oligonucleotides (Lockhart, et al., Nature Biotechnology 14:1675-1680 (1996); and Lipschutz, et al., Nature Genetics Supplement 21: 20-24, 1999). Other arrays including full length cDNA sequences with perfect or near perfect complementarity to a particular cDNA (Schena et al. (Science 270:467-470 (1995); and DeRisi et al. (Nature Genetics 14:457-460 (1996)). Such arrays can also include various control probes, such as a probe complementarity with a house keeping gene likely to be expressed in most samples. Regardless of the specifics of array design, an array contains one or more probes either perfectly complementary to a particular target mRNA or sufficiently complementarity to the target mRNA to distinguish it from other mRNAs in the sample, and the presence of such a target mRNA can be determined from the hybridization signal of such probes, optionally by comparison with mismatch or other control probes included in the array. Typically, the target bears a fluorescent label, in which case hybridization intensity can be determined by, for example, a scanning confocal microscope in photon counting mode. Appropriate scanning devices are described by e.g., U.S. Pat. No. 5,578,832, and U.S. Pat. No. 5,631,734. The intensity of labeling of probes hybridizing to a particular mRNA or its amplification product provides a raw measure of expression level.

In other methods, expression levels are determined by so-called "real time amplification" methods also known as quantitative PCR or Taqman (see, e.g., U.S. Pat. No. 5,210, 015 to Gelfand, U.S. Pat. No. 5,538,848 to Livak, et al., and U.S. Pat. No. 5,863,736 to Haaland, as well as Heid, C. A., et al., Genome Research, 6:986-994, 1996; Gibson, U. E. M, et al., Genome Research 6:995-1001, 1996; Holland, P. M., et al., Proc. Natl. Acad. Sci. USA 88:7276-7280, 1991; and Livak, K. J., et al., PCR Methods and Applications 357-362, 1995). The basis for this method of monitoring the formation of amplification product is to measure continuously PCR product accumulation using a dual-labeled fluorogenic oligonucleotide probe. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye The probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified. mRNA levels can also be measured without amplification by hybridization to a probe, for example, using a branched nucleic acid probe, such as a QuantiGene® Reagent System from Panomics.

In some embodiments, the expression level of the gene products (e.g., RNA) is determined by sequencing, such as by RNA sequencing or by DNA sequencing (e.g., of cDNA generated from reverse-transcribing RNA (e.g., mRNA) from a sample). Sequencing may be performed by any available method or technique. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/ Thermo-Fisher), massively-parallel sequencing, clonal single molecule Array (Solexa), shotgun sequencing, Maxim-Gilbert sequencing, primer walking, and any other sequencing methods known in the art.

Measuring gene expression levels may comprise reverse transcribing RNA (e.g., mRNA) within a sample in order to produce cDNA. The cDNA may then be measured using any of the methods described herein (e.g., PCR, digital PCR, qPCR, microarray, SAGE, blotting, sequencing, etc.).

Alternatively or additionally, expression levels of genes can be determined at the protein level, meaning that levels of proteins encoded by the genes discussed above are measured. Several methods and devices are well known for determining levels of proteins including immunoassays such as described in e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792. These assays include various sandwich, competitive, or non-competitive assay formats, to generate a signal that is related to the presence or amount of an protein analyte of interest. Any suitable immunoassay may be utilized, for example, lateral flow, enzyme-linked immunoassays (ELISA), radioimmunoassays (RIAs), competitive binding assays, and the like. Numerous formats for antibody arrays have been described proposed employing antibodies. Such arrays typically include different antibodies having specificity for different proteins intended to be detected. For example, usually at least one hundred different antibodies are used to detect one hundred different protein targets, each antibody being specific for one target. Other ligands having specificity for a particular protein target can also be used, such as the synthetic antibodies disclosed in WO/2008/ 048970. Other compounds with a desired binding specificity can be selected from random libraries of peptides or small molecules. U.S. Pat. No. 5,922,615 describes a device that utilizes multiple discrete zones of immobilized antibodies on membranes to detect multiple target antigens in an array. U.S. Pat. Nos. 5,458,852, 6,019,944, U.S. Pat. No. 6,143, 576. Microtiter plates or automation can be used to facilitate detection of large numbers of different proteins. Protein levels can also be determined by mass spectrometry as described in the examples.

The selection of genes for determination of expression levels depends on the particular application. In general, the genes are selected from one of the tables indicated above as appropriate for the application. In some methods, expression levels of at least 2, 3, 4, 5, 10, 20, 25, 50, 100, 150, 250 (e.g. 100-250) genes shown in any of Table 4, 2, or 3 are determined. In some methods, expression levels of at least 2, 3, 4, 5, 10, 20, 25, 50, 100, 150, 200 or all genes shown in Table 4 are determined. In some methods, expression levels of at least 2, 3, 4, 5, 10, 20, 25, 50, 75, 100, 125 or all genes shown in Table 5 are determined. In some methods, expression levels of at least 2, 3, 4, 5, 10, 20, 25, 50, 100, 150, 200, 250, 300 or all genes shown in Table 6 are determined. In still some methods, expression levels of at least 2, 3, 4, 5, 10, 20, 25, 50, 75, 100, 125 or all genes shown in Table 5, as well as expression levels of at least 2, 3, 4, 5, 10, 20, 25, 50, 100, 150, 200, 250, 300 or all genes shown in Table 6, are determined. In some methods, expression levels of 1, 2, 3, 4, 5, 6, 7, 8, 9, 10, 11, 12, 13, 14, 15, 16, 17, 18, 19, 20 or more genes found in Tables 4, 5, or 6 are determined. In some methods, genes are selected such that genes from several different pathways are represented. The genes within a pathway tend to be expressed in a coordinated expression whereas genes from different pathways tend to be expressed more independently. Thus, changes in expression based on the aggregate changes of genes from different pathways can have greater statistical significance than aggregate changes of genes within a pathway. In some cases, expression levels of the top 5, top 10, top 15, top 20, top 25, top 30, top 35, top 40, top 45, top 50, top 55, top 60, top 65, top 70, top 75, top 80, top 85, top 90, top 95, top 100, top 150 or top 200 genes listed in Tables 4, 5, or 6 are determined. As noted above, expression levels can be measured at either mRNA levels or protein levels.

Expression levels of the present genes and/or proteins can be combined with or without determination of expression levels of any other genes or proteins of interest (e.g., genes or proteins associated with rejection of livers or other organs, e.g., as described in Hama et al., Liver Transpl. 2009 15(5):509-21; Rattanasiri et al., Transpl Immunol. 2013 28(1):62-70; and Spivey et al., J. Translational Med. 2011 9:174. In some methods, the genes in the expression profiles to be measured do not include at least one or all of the genes discussed in Gehrau et al., Mol. Med. 2011; 17(7-8):824-33; Asaoka et al., Liver Transpl. 2009 December; 15(12):1738-49; and Sreekumar et al., Liver Transpl. 2002 September; 8(9):814-21. These include, e.g., genes encoding arginase type II (ARG2), ethylmalonic encephalopathy 1 (ETHE1), transmembrane protein 176A (TMEM176A), TMEM176B, caspase 8, apoptosis-related cysteine peptidase, and bone morphogenetic protein 2, transcription factor ISGF-3, interferon-responsive transcription factor (transcription factors), heat shock protein 70 (stress response/chaperone), ubiquitin-conjugating enzyme E2, ubiquitin, ubiquitin-activating enzyme E1 and granzyme B (protein degradation), nicotinamide N-methyltransferase (nicotinamide metabolism), major histocompatibility complex (MHC) class I and II (immune function), transforming growth factor (TGF)-beta and insulin-like growth factor I (growth factors), glycogen synthase and phosphoenolpyruvate carboxykinase (glucose metabolism), cytidine triphosphate (CTP) synthetase, medium-chain acyl-CoA dehydrogenase and triglyceride lipase (fatty acid metabolism), complement components C1q and C3 (complement activation), p-selectin (cell adhesion), tumor necrosis factor (TNF)-related apoptosis inducing ligand (TRAIL), TNF-alpha converting enzyme, TNF-alpha inducible protein A20, TNF-alpha (apoptosis), alanyl-tRNA synthetase, ribosomal protein-L8, elongation TU, protein synthesis factor eIF-4C, elongation factor-2, eukaryotic initiation factor-4AI and elongation factor-1 alpha (protein synthesis), chaperonin 10 and protein disulfide isomerase (protein folding), insulin-like growth factor (IGF)-binding protein (growth factor), GLUT-2 (glucose metabolism), very-long-chain acyl CoA dehydrogenase and fatty acid omega hydroxylase (fatty acid metabolism), and MT-1 and glutathione peroxidase (DNA metabolism).

Regardless of the format adopted, the present methods can (but need not) be practiced by detection expression levels of a relatively small number of genes or proteins compared with the whole genome level expression analysis described in the Examples. In some methods, the total number of genes whose expression levels are determined is less than 5000, 1000, 500, 200, 100, 50, 25, 10, 5 or 3. In some methods, the total number of genes whose expression level is determined is 100-1500, 100-250, 500-1500 or 750-1250. In some methods, the total number of proteins whose expression levels are determined is less than 5000, 1000, 500, 200, 100, 50, 25, 10, 5 or 3. In some methods, the total number of proteins whose expression level is determined is 100-1500, 100-250, 500-1500 or 750-1250. Correspondingly, when an array form is used for detection of expression levels, the array includes probes or probes sets for less than 5000, 1000, 500, 200, 100, 50, 25, 10, 5 or 3 genes. Thus, for example, an Affymetrix GeneChip® expression monitoring array contains a set of about 20-50 oligonucleotide probes (half match and half-mismatch) for monitoring each gene of interest. Such an array design would include less than 5000, 1000, 500, 200, 100, 50, 25, 10, 5 or 3 such probes sets for detecting less than 5000, 1000, 500, 200, 100, 50, 25, 10, 5 or 3 genes. By further example, an alternative array including one cDNA for each gene whose expression level is to be detected would contain less than 5000, 1000, 500, 200, 100, 50, 25, 10, 5 or 3 such cDNAs for analyzing less than 5000, 1000, 500, 200, 100, 50, 25, 10, 5 or 3 genes. By further example, an array containing a different antibody for each protein to be detected would containing less than 5000, 1000, 500, 200, 100, 50, 25, 10, 5 or 3 different antibodies for analyzing less than 5000, 1000, 500, 200, 100, 50, 25, 10, 5 or 3 gene products.

V. Analysis of Expression Levels

Analysis of expression levels initially provides a measurement of the expression level of each of several individual genes. The expression level can be absolute in terms of a concentration of an expression product, or relative in terms of a relative concentration of an expression product of interest to another expression product in the sample. For example, relative expression levels of genes can be expressed with respect to the expression level of a housekeeping gene in the sample. Relative expression levels can also be determined by simultaneously analyzing differentially labeled samples hybridized to the same array. Expression levels can also be expressed in arbitrary units, for example, related to signal intensity.

The individual expression levels, whether absolute or relative, can be converted into values or other designations providing an indication of presence or risk of a liver transplant rejection or injury by comparison with one or more reference points. For different phenotypes of graft injuries (e.g., AR, ADNR, HCV-R, HCV+AR; or TX), different gene sets are typically used in the analysis. For example, acute dysfunction no rejection (ADNR) can be determined with gene sets selected from Table 4 (for blood samples) or Table 6 (for biopsy samples). Acute rejection (AR) can be determined via blood samples with genes selected from Table 4 or Table 5. HCV recurrence with or without acute rejection may similarly be determined using genes from Table 5 (blood samples).

For liver transplant with each of the phenotypes noted above, the reference points can include a measure of an average or mean expression level of a gene in subjects having had a liver transplant with the specific phenotype. The reference points can also include a scale of values found in liver transplant patients including patients having that phenotype. The reference points can also or alternatively include a reference value in the subject before liver transplant, or a reference value in a population of patients who have not undergone liver transplant. Such reference points can be expressed in terms of absolute or relative concentrations of gene products as for measured values in a sample.

For comparison between a measured expression level and reference level(s), the measured level sometimes needs to be normalized for comparison with the reference level(s) or vice versa. The normalization serves to eliminate or at least minimize changes in expression level unrelated to the specific liver transplant injury or phenotype (e.g., from differences in overall health of the patient or sample preparation) or from purely technical artifacts. Normalization can be performed by determining what factor is needed to equalize a profile of expression levels measured from different genes in a sample with expression levels of these genes in a set of reference samples from which the reference levels were determined. Commercial software is available for performing such normalizations between different sets of expression levels.

Comparison of the measured expression level of a gene with one or more of the above reference points provides a value (i.e., numerical) or other designation (e.g., symbol or word(s)) of presence or susceptibility to a liver transplant injury. In some methods, a binary system is used; that is a measured expression level of a gene is assigned a value or other designation indicating presence or susceptibility to a liver transplant injury or lack thereof without regard to degree. For example, the expression level can be assigned a value of 1 to indicate presence or susceptibility to an injury and −1 to indicate absence or lack of susceptibility to the injury. Such assignment can be based on whether the measured expression level is closer to an average or mean level in liver transplant patients having or not having a specific injury phenotype. In other methods, a ternary system is used in which an expression level is assigned a value or other designation indicating presence or susceptibility to a specific injury phenotype or lack thereof or that the expression level is uninformative. Such assignment can be based on whether the expression level is closer to the average or mean level in liver transplant patient undergoing the specific injury, closer to an average or mean level in liver transplant patients lacking the injury or intermediate between such levels. For example, the expression level can be assigned a value of +1, −1 or 0 depending on whether it is closer to the average or mean level in patients undergoing the injury, is closer to the average or mean level in patients not undergoing the injury or is intermediate. In other methods, a particular expression level is assigned a value on a scale, where the upper level is a measure of the highest expression level found in liver transplant patients and the lowest level of the scale is a measure of the lowest expression level found in liver transplant patients at a defined time point at which patients may be susceptible to a grant rejection or injury (e.g., one year post transplant). Preferably, such a scale is normalized scale (e.g., from 0-1) such that the same scale can be used for different genes. Optionally, the value of a measured expression level on such a scale is indicated as being positive or negative depending on whether the upper level of the scale associates with presence or susceptibility to the injury or lack thereof. It does not matter whether a positive or negative sign is used for an injury phenotype or lack thereof as long as the usage is consistent for different genes.

Values or other designation can also be assigned based on a change in expression level of a gene relative to a previous measurement of the expression level of gene in the same patient. Here as elsewhere expression level of a gene can be measured at the protein or nucleic acid level. Such a change can be characterized as being toward, away from or neutral with respect to average or mean expression levels of the gene in liver transplant patients undergoing or not undergoing a grant rejection or injury. For example, a gene whose expression level changes toward an average or mean expression level in liver transplant patients undergoing a graft injury can be assigned a value of 1, and a gene whose express level changes way from an average or mean expression level in liver transplant patients undergoing the injury and toward an average or mean expression level in liver transplant patients not undergoing the injury can be assigned a value −1. Of course, more sophisticated systems of assigning values are possible based on the magnitude of changes in expression of a gene in a patient.

Having determined values or other designations of expression levels of individual genes providing an indication of presence or susceptibility to a liver graft injury or lack thereof, the values or designations may be combined to provide an aggregate value for all of the genes in the signature being analyzed. If each gene is assigned a score of +1 if its expression level indicates presence or susceptibility to a graft injury and −1 if its expression level indicates absence or lack of susceptibility to the injury and optionally zero if uninformative, the different values can be combined by addition. The same approach can be used if each gene is assigned a value on the same normalized scale and assigned as being positive or negative depending whether the upper point of the scale is associate with presence or susceptibility to a specific liver grant injury or lack thereof. The same method can be performed using the signal intensity. In some cases, the signal intensity for each gene is obtained and used to compute a score. The score may be obtained by adding the upregulated to obtain an upregulated value and adding the downregulated genes to obtain a downregulated value and then comparing the downregulated value with the upregulated value (e.g., by calculating a ratio) to determine the score. Other methods of combining values for individual markers of disease into a composite value that can be used as a single marker are described in US20040126767 and WO/2004/059293. In some cases, the score may be used to evaluate severity of a transplant condition, such as by comparing the score with a score normally associated with liver transplant rejection. In some cases, the score may be used to monitor a subject transplant recipient over time. In such case, scores at a plurality of timepoints maybe compared in order to assess the relative condition of the subject. For example, if the subject's score rises over time, that may indicate that the subject has liver transplant rejection and that his or her condition is worsening over time.

Sample Data

The data pertaining to the sample may be compared to data pertaining to one or more control samples, which may be samples from the same patient at different times. In some cases, the one or more control samples may comprise one or more samples from healthy subjects, unhealthy subjects, or a combination thereof. The one or more control samples may comprise one or more samples from healthy subjects, subjects suffering from transplant dysfunction with no rejection, subjects suffering from transplant rejection, or a combination thereof. The healthy subjects may be subjects with normal transplant function. The data pertaining to the sample may be sequentially compared to two or more classes of samples. The data pertaining to the sample may be sequentially compared to three or more classes of samples. The classes of samples may comprise control samples classified as being from subjects with normal transplant function, control samples classified as being from subjects suffering from transplant dysfunction with no rejection, control samples classified as being from subjects suffering from transplant rejection, or a combination thereof.

Classifiers

The methods include using a trained classifier or algorithm to analyze sample data, particularly to detect liver transplant rejection. In some instances, the expression levels from sample are used to develop or train an algorithm or classifier provided herein. In some instances, gene expression levels are measured in a sample from a transplant recipient (or a healthy or transplant excellent control) and a classifier or algorithm (e.g., trained algorithm) is applied to the resulting data in order to detect, predict, monitor, or estimate the risk of a transplant condition (e.g., liver transplant rejection).

Training of multi-dimensional classifiers (e.g., algorithms) may be performed using numerous samples. For example, training of the multi-dimensional classifier may be performed using at least about 10, 20, 30, 40, 50, 60, 70, 80, 90, 100, 110, 120, 130, 140, 150, 160, 170, 180, 190, 200 or more samples. In some cases, training of the multi-dimensional classifier may be performed using at least about 200, 210, 220, 230, 240, 250, 260, 270, 280, 290, 300, 350, 400, 450, 500 or more samples. In some cases, training of the multi-dimensional classifier may be performed using at least about 525, 550, 600, 650, 700, 750, 800, 850, 900, 950, 1000, 1100, 1200, 1300, 1400, 1500, 1600, 1700, 1800, 2000 or more samples.

Further disclosed herein are classifier sets and methods of producing one or more classifier sets. The classifier set may comprise one or more genes, particularly genes from Tables 4, 5, or 6. In some cases, the classifier set may comprise 1, 2, 3, 4, 5, 6, 7, 8, 9, 10, 11, 12, 13, 14, 15, 16, 17, 18, 19, 20, 50, 100, 150, 200, 300 or more genes from Tables 4, 5, or 6. Disclosed herein is the use of a classification system comprises one or more classifiers. In some instances, the classifier is a 2-, 3-, 4-, 5-, 6-, 7-, 8-, 9-, or 10-way classifier. In some instances, the classifier is a 15-, 20-, 25-, 30-, 35-, 40-, 45-, 50-, 55-, 60-, 65-, 70-, 75-, 80-, 85-, 90-, 95-, or 100-way classifier. In some preferred embodiments, the classifier is a three-way classifier. In some embodiments, the classifier is a four-way classifier.

A two-way classifier may classify a sample from a subject into one of two classes. In some instances, a two-way classifier may classify a sample from an organ transplant recipient into one of two classes comprising liver transplant rejection and normal transplant function (TX). In some instances, a three-way classifier may classify a sample from a subject into one of three classes. A three-way classifier may classify a sample from an organ transplant recipient into one of three classes comprising AR, ADNR, and TX In some cases, the classifier may work by applying two or more classifiers sequentially.

The methods, kits, and systems disclosed herein may comprise one or more algorithms or uses thereof. Algorithms such as those described in U.S. application Ser. No. 14/481,167, filed Sep. 9, 2014, may be used in the methods, kits, and systems disclosed herein. The one or more algorithms may be used to classify one or more samples from one or more subjects. The one or more algorithms may be applied to data from one or more samples. The data may comprise gene expression data. The data may comprise sequencing data. The data may comprise array hybridization data. Additionally, the classifiers described in U.S. application Ser. No. 14/481,167, filed Sep. 9, 2014, may be used in the methods, kits, and systems disclosed herein.

VI. Diagnosis, Prognosis and Monitoring

The above described methods can provide a value or other designation for a patient which indicates whether the aggregate measured expression levels in a patient is more like liver transplant patients with one of the graft injury phenotypes noted above (e.g., AR, ADNR, HCV-R, HCV+R, or TX). Such a value provides an indication that the patient either has or is at enhanced risk of developing a specific graft injury, or conversely does not have or is at reduced risk of having that specific graft injury phenotype. Risk is a relative term in which risk of one patient is compared with risk of other patients either qualitatively or quantitatively. For example, the value of one patient can be compared with a scale of values for a population of patients having undergone liver transplant to determine whether the patient's risk relative to that of other patients. In general, diagnosis is the determination of the present condition of a patient (e.g., presence or absence of a graft injury) and prognosis is developing future course of the patient (e.g., risk of developing liver transplant rejection or injury in the future or likelihood of improvement in response to treatment); however, the analyses contemplated by these terms may overlap or even be the same. For example, the present methods alone do not necessarily distinguish between presence and enhanced risk of a liver transplant injury. However, these possibilities can be distinguished by additional testing.

In some instances, the methods, compositions, systems and kits described herein provide information to a medical practitioner that can be useful in making a therapeutic decision. Therapeutic decisions may include decisions to: continue with a particular therapy, modify a particular therapy, alter the dosage of a particular therapy, stop or terminate a particular therapy, altering the frequency of a therapy, introduce a new therapy, introduce a new therapy to be used in combination with a current therapy, or any combination of the above. In some instances, the results of diagnosing, predicting, or monitoring a condition of a transplant recipient may be useful for informing a therapeutic decision such as removal of the transplant. In some instances, the removal of the transplant can be an immediate removal. In other instances, the therapeutic decision can be a retransplant. Other examples of therapeutic regimen can include a blood transfusion in instances where the transplant recipient is refractory to immunosuppressive or antibody therapy.

If a patient is indicated as having or being at enhanced risk of a liver transplant injury, the physician can subject the patient to additional testing including performing a liver biopsy, or performing other analyses such as examining whether there is an increases in bilirubin or liver enzyme levels, or both. Additionally or alternatively, the physician can change the treatment regime being administered to the patient. This includes administration of steroid boluses and the addition of other drugs to the maintenance therapy, or the administration of antilymphocyte antibodies in case of resistance to the primary line of therapy. In some embodiments, the change in treatment regime can include administering an additional or different drug to a patient, or administering a higher dosage or frequency of a drug already being administered to the patient. Many different drugs are available for treating rejection, such as immunosuppressive drugs used to treat transplant rejection calcineurin inhibitors (e.g., cyclosporine, tacrolimus), mTOR inhibitors (e.g., sirolimus and everolimus), anti-proliferatives (e.g., azathioprine, mycophenolic acid), corticosteroids (e.g., prednisolone and hydrocortisone) and antibodies (e.g., basiliximab, daclizumab, Orthoclone, anti-thymocyte globulin and anti-lymphocyte globulin). In the case of HCV recurrence, the patients may be additionally administered drugs to counter the viral infection, e.g., interferons, ribavirin, and protease inhibitors.

Conversely, if the value or other designation of aggregate expression levels of a patient indicates the patient does not have or is at reduced risk of graft injury, the physician need not order further diagnostic procedures, particularly not invasive ones such as biopsy. Further, the physician can continue an existing treatment regime, or even decrease the dose or frequency of an administered drug.

In some methods, expression levels are determined at intervals in a particular patient (i.e., monitoring). Preferably, the monitoring is conducted by serial minimally-invasive tests such as blood draws; but, in some cases, the monitoring may also involve analyzing a liver biopsy, either histologically or by analyzing a molecular profile. The monitoring may occur at different intervals, for example the monitoring may be hourly, daily, weekly, monthly, yearly, or some other time period, such as twice a month, three times a month, every two months, every three months, etc.

Such methods can provide a series of values changing over time indicating whether the aggregate expression levels in a particular patient are more like the expression levels in patients undergoing a specific liver transplant rejection/injury or not undergoing the rejection/injury. Movement in value toward or away from the graft injury can provide an indication whether an existing immunosuppressive regime is working, whether the immunosuppressive regime should be changed or whether a biopsy or increased monitoring by other markers rate should be performed.

The methods provided herein include administering a blood test (e.g., a test to detect acute rejection) to a transplant recipient who has already undergone a surveillance or protocol biopsy of the liver and received a biopsy result in the form of a histological analysis or a molecular profiling analysis. In some particular instances, the analysis of the liver biopsy (e.g., by histology or molecular profiling) may result in ambiguous, inconclusive or borderline results. In such cases, a blood test provided herein may assist a caregiver with determining whether the transplant recipient has acute rejection or with interpreting the biopsy. In other cases the biopsy itself may be inconclusive or ambiguous, and in such cases the molecular analysis of the biopsy may be used in adjunct with the histology to confirm a diagnosis. In some instances, the analysis of the liver biopsy may yield a negative result. In such cases, the subject may receive a blood test provided herein in order to confirm the negative result, or to detect acute rejection or other transplant condition. In some cases, after receiving any type of biopsy result (e.g., negative result, ambiguous, inconclusive, borderline, positive), the patient may receive multiple, serial blood tests to monitor changes in molecular markers correlated with acute rejection.

The methods provided herein also include administering a biopsy test (e.g., histology or molecular profiling) to a transplant recipient who has received a molecular blood profiling test. For example, the transplant recipient may receive an ambiguous, inconclusive or borderline result on a blood molecular profiling test. In such cases, the patient's healthcare worker may use the results of a liver biopsy test as a complement to the blood test to determine whether the subject is experiencing acute rejection. In another example, the transplant recipient may have received a positive result on a blood molecular profiling test, indicating that the transplant recipient has, or likely has, acute rejection, or even multiple positive results over time. In such cases, the patient's physician or other healthcare worker may decide to biopsy the patient's liver in order to detect liver transplant rejection. Such liver transplant rejection test may be a molecular profiling analysis of the patient's liver, as described herein. In some cases, a histological analysis of the liver biopsy may be performed instead of, or in addition to, the molecular analysis of the biopsy. In some cases, the physician may decide to wait a certain period of time after receiving the positive blood result to perform the biopsy test.

The methods provided herein may often provide early detection of liver transplant rejection and may help a patient to obtain early treatment such as receiving immunosuppressive therapy or increasing an existing immunosuppressive regimen. Such early treatment may enable the patient to avoid more serious consequences associated with acute rejection later in time, such as allograft loss. In some cases, such early treatments may be administered after the patient receives both a molecular profiling blood test and a biopsy analyzed either by molecular profiling or histologically.

VII. Drug Screening

The expression profiles associated with a liver transplant rejection/injury or lack thereof provided by the invention are useful in screening drugs, either in clinical trials or in animal models of the injury. A clinical trial can be performed on a drug in similar fashion to the monitoring of an individual patient described above, except that drug is administered in parallel to a population of liver transplant patients, usually in comparison with a control population administered a placebo.

The changes in expression levels of genes can be analyzed in individual patients and across a treated or control population. Analysis at the level of an individual patient provides an indication of the overall status of the patient at the end of the trial (i.e., whether gene expression profile indicates presence or enhanced susceptibility to a liver transplant rejection/injury) and/or an indication whether that profile has changed toward or away from such indication in the course of the trial. Results for individual patients can be aggregated for a population allowing comparison between treated and control populations.

Similar trials can be performed in non-human animal models of chronic liver disease, e.g., the animal model described in Liu et al., Am. J. Physiol. Gastrointest Liver Physiol. 304:G449-68, 2013. With the animal models, the expression levels of genes detected are the species variants or homologs of the human genes referenced above in whatever species of non-human animal on which tests are being conducted. Although the average or mean expression levels of human genes determined in human liver transplant patients undergoing or not undergoing a specific transplant rejection/injury are not necessarily directly comparable to those of homolog genes in an animal model, the human values can nevertheless be used to provide an indication whether a change in expression level of a non-human homolog is in a direction toward or away from an injury or susceptibility thereto. The expression profile of individual animals in a trial can provide an indication of the status of the animal at the end of the trial with respect to presence or susceptibility to the injury and/or change in such status during the trial. Results from individual animals can be aggregated across a population and treated and control populations compared. Average changes in the expression levels of genes can then be compared between the two populations.

VIII. Computer Implemented Methods

Expression levels can be analyzed and associated with status of a subject (e.g., presence or susceptibility to a liver transplant injury) in a digital computer. Optionally, such a computer is directly linked to a scanner or the like receiving experimentally determined signals related to expression levels. Alternatively, expression levels can be input by other means. The computer can be programmed to convert raw signals into expression levels (absolute or relative), compare measured expression levels with one or more reference expression levels, or a scale of such values, as described above. The computer can also be programmed to assign values or other designations to expression levels based on the comparison with one or more reference expression levels, and to aggregate such values or designations for multiple genes in an expression profile. The computer can also be programmed to output a value or other designation providing an indication of presence or susceptibility to a liver transplant rejection or injury as well as any of the raw or intermediate data used in determining such a value or designation. The computer can also be used to run statistical tools and algorithms that test the data for patterns of expression that could be diagnostic or prognostic, as well as test for the validity and utility of gene signatures A typical computer (see U.S. Pat. No. 6,785,613 FIGS. 4 and 5) includes a bus which interconnects major subsystems such as a central processor, a system memory, an input/output controller, an external device such as a printer via a parallel port, a display screen via a display adapter, a serial port, a keyboard, a fixed disk drive and a floppy disk drive operative to receive a floppy disk. Many other devices can be connected such as a scanner via I/O controller, a mouse connected to serial port or a network interface. The computer contains computer readable media holding codes to allow the computer to perform a variety of functions. These functions include controlling automated apparatus, receiving input and delivering output as described above. The automated apparatus can include a robotic arm for delivering reagents for determining expression levels, as well as small vessels, e.g., microtiter wells for performing the expression analysis.

Figure 2:
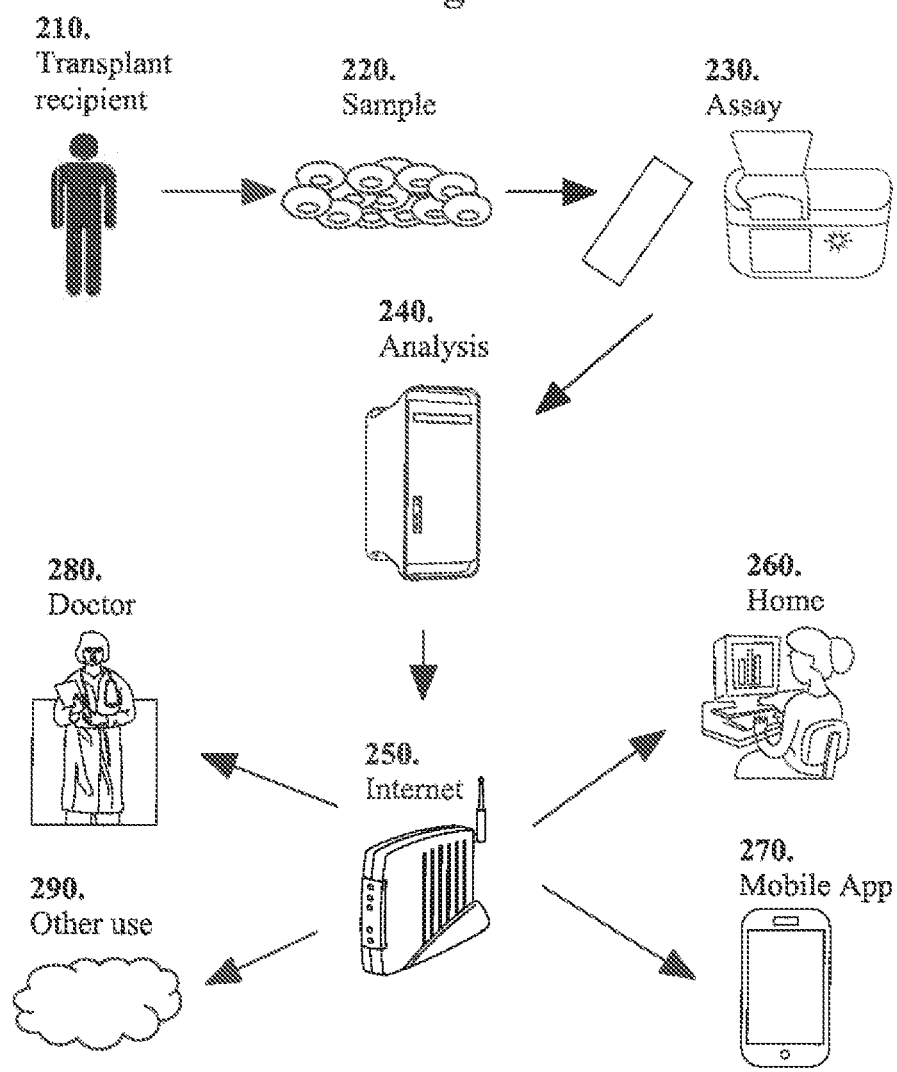
FIG. 2 shows a schematic overview of certain methods of acquiring samples, analyzing results, and transmitting reports over a computer network.

The methods, systems, kits and compositions provided herein may also be capable of generating and transmitting results through a computer network. As shown in FIG. 2, a sample (220) is first collected from a subject (e.g. transplant recipient, 210). The sample is assayed (230) and gene expression products are generated. A computer system (240) is used in analyzing the data and making classification of the sample. The result is capable of being transmitted to different types of end users via a computer network (250). In some instances, the subject (e.g. patient) may be able to access the result by using a standalone software and/or a web-based application on a local computer capable of accessing the internet (260). In some instances, the result can be accessed via a mobile application (270) provided to a mobile digital processing device (e.g. mobile phone, tablet, etc.). In some instances, the result may be accessed by physicians and help them identify and track conditions of their patients (280). In some instances, the result may be used for other purposes (290) such as education and research.

Additionally, the computer programs, non-transitory computer-readable storage medium, web applications, mobile applications, stand-alone applications, web browser plug-ins, software modules, databases, and data transmissions described in U.S. application Ser. No. 14/481,167, filed Sep. 9, 2014, may be used in the methods, kits, and systems disclosed herein.

EXAMPLES

The following examples are offered to illustrate, but not to limit the present invention.

Example 1. Expression Signatures to Distinguish Liver Transplant Injuries

Biomarker profiles diagnostic of specific types of graft injury post-liver transplantation (LT), such as acute rejection (AR), hepatitis C virus recurrence (HCV-R), and other causes (acute dysfunction no rejection/recurrence; ADNR) could enhance the diagnosis and management of recipients. Our aim was to identify diagnostic genomic (mRNA) signatures of these clinical phenotypes in the peripheral blood and allograft tissue.

Patient Populations: The study population consisted of 114 biopsy-documented Liver PAXgene whole blood samples comprised of 5 different phenotypes: AR (n=25), ADNR (n=16), HCV(n=36), HCV+AR (n=13), and TX (n=24).

Gene Expression Profiling and Analysis: All samples were processed on the Affymetrix HG-1)133 PM only peg microarrays. To eliminate low expressed signals we used a signal filter cut-off that was data dependent, and therefore expression signals <Log 2 4.23 (median signals on all arrays) in all samples were eliminated leaving us with 48882 probe sets from a total of 54721 probe sets. The first comparison performed was a 3-way ANOVA analysis of AR vs. ADNR vs. TX. This yielded 263 differentially expressed probesets at a False Discovery rate (FDR <10%). We used these 263 probesets to build predictive models that could differentiate the three classes. We used the Nearest Centroid (NC) algorithm to build the predictive models. We ran the predictive models using two different methodologies and calculated the Area Under the Curve (AUC). First we did a one-level cross validation, where the data is first divided into 10 random partitions. At each iteration, $\frac{1}{10}$ of the data is held out for testing while the remaining $\frac{9}{10}$ of the data is used to fit the parameters of the model. This can be used to obtain an estimate of prediction accuracy for a single model. Then we modeled an algorithm for estimating the optimism, or over-fitting, in predictive models based on using bootstrapped datasets to repeatedly quantify the degree of over-fitting in the model building process using sampling with replacement. This optimism corrected AUC value is a nearly unbiased estimate of the expected values of the optimism that would be obtained in external validation (we used 1000 randomly created data sets). Table 1 shows the optimism corrected AUCs for the 263 probesets that were used to predict the accuracies for distinguishing between AR, ADNR and TX in Liver PAXgene samples.

It is clear from the above table that the 263 probeset classifier was able to distinguish the three phenotypes with very high predictive accuracy. The NC classifier had a sensitivity of 83%, specificity of 93%, and positive predictive value of 95% and a negative predictive value of 78% for the AR vs. ADNR comparison. It is important to note that these values did not change after the optimism correction where we simulated 1000 data sets showing that these are really robust signatures. A heat map of the 263 classifier is prepared in order to show how well they distinguished the three phenotypes (data not shown), and a Principal Components Analysis Plot of the three phenotypes separated using the 263 probeset classifier is also prepared (data not shown).

The next comparison we performed was a 3-way ANOVA of AR vs. HCV vs. HCV+AR which yielded 147 differentially expressed probesets at a p value <0.001. We chose to use this set of predictors because at an FDR <10% we had only 18 predictors, which could possibly be due to the smaller sample size of the HCV+AR (n=13) or a smaller set of differentially expressed genes in one of the phenotypes. However, since this was a discovery set to test the proof of principle whether there were signatures that could distinguish samples that had an admixture of HCV and AR from the pure AR and the pure HCV populations, we ran the predictive algorithms on the 147 predictors. Table 2 shows the AUCs for the 147 probesets that were used to predict the accuracies for distinguishing between AR, HCV and HCV+ AR in Liver PAXgene samples.

The NC classifier had a sensitivity of 87%, specificity of 97%, and positive predictive value of 95% and a negative predictive value of 92% for the AR vs HCV comparison using the optimism correction where we simulated 1000 data sets giving us confidence that the simulations that were done to mimic a real clinical situation did not alter the robustness of this set of predictors. A heat map of the 147 classifier is prepared to show how well they distinguished the three phenotypes (data not shown). A Principal Components Analysis Plot of the three phenotypes separated using the 147 probeset classifier, AR (n=16), HCV(n=30) and HCV+ AR (n=11) is also prepared (data not shown).

For the biopsies, again, we performed a 3-way ANOVA of AR vs. HCV vs. HCV+AR that yielded 320 differentially expressed probesets at an FDR <10%. We specifically did this because at a p-value <0.001 there were over 950 probesets. We ran the predictive models on this set of classifiers in the same way mentioned for the PAXgene samples. Table 3 shows the AUCs for the one-level cross validation and the optimism correction for the classifier set comprised of 320 probesets that were used to predict the accuracies for distinguishing between AR, HCV and HCV+ AR in Liver biopsies.

In summary, for both the blood and the biopsy samples from liver transplant subjects we have classifier sets that can distinguish AR, HCV and HCV+AR with AUCs between 0.79-0.83 in blood and 0.69-0.83 in the biopsies. We also have a signature from whole blood that can distinguish AR, ADNR and TX samples with AUC's ranging from 0.87-0.92.

TABLE 1

AUCs for the 263 probesets to predict AR, ADNR and TX in Liver whole blood samples.

| Algorithm | Predictors | Comparison | AUC | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 263 | AR vs. ADNR | 0.882 | 88 | 83 | 93 | 95 | 78 |
| Nearest Centroid | 263 | AR vs. TX | 0.943 | 95 | 95 | 95 | 95 | 95 |
| Nearest Centroid | 263 | ADNR vs. TX | 0.883 | 88 | 93 | 83 | 78 | 95 |

TABLE 2

AUCs for the 147 probesets to predict AR, HCV and AR + HCV in Liver whole blood samples.

| Algorithm | Predictors | Comparison | AUC | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 147 | AR vs. HCV | 0.952 | 96 | 87 | 97 | 95 | 92 |
| Nearest Centroid | 147 | AR vs. HCV + AR | 0.821 | 82 | 91 | 92 | 95 | 85 |
| Nearest Centroid | 147 | HCV vs. HCV + AR | 0.944 | 94 | 92 | 97 | 92 | 97 |

TABLE 3

AUCs for the 320 probesets to predict AR, ADNR and TX in Liver biopsy samples.

| Algorithm | Predictors | Comparison | AUC | Predictive Accuracy (%) | Sensitivity (%) | Specificity (%) | Postive Predictive Value (%) | Negative Predictive Value (%) |
|---|---|---|---|---|---|---|---|---|
| Nearest Centroid | 320 | AR vs. HCV | 0.937 | 94 | 84 | 100 | 100 | 89 |
| Nearest Centroid | 320 | AR vs. HCV + AR | 1.000 | 100 | 100 | 100 | 100 | 100 |
| Nearest Centroid | 320 | HCV vs. HCV + AR | 0.829 | 82 | 82 | 89 | 75 | 92 |

TABLE 4

263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 1 | 215415_PM_s_at | LYST | lysosomal trafficking regulator | 3.79E-07 | 32.3 | 25.8 | 43.6 |
| 2 | 241038_PM_at | — | — | 4.79E-07 | 16.1 | 21.0 | 16.4 |
| 3 | 230776_PM_at | — | — | 2.10E-06 | 10.4 | 13.7 | 10.2 |
| 4 | 212805_PM_at | PRUNE2 | prune homolog 2 (*Drosophila*) | 4.09E-06 | 15.8 | 15.2 | 33.9 |
| 5 | 215090_PM_x_at | LOC440434 | aminopeptidase puromycin sensitive pseudogene | 7.28E-06 | 164.6 | 141.0 | 208.0 |
| 6 | 243625_PM_at | — | — | 7.64E-06 | 31.2 | 20.8 | 29.9 |
| 7 | 232222_PM_at | C18orf49 | chromosome 18 open reading frame 49 | 8.85E-06 | 33.7 | 35.7 | 42.4 |
| 8 | 235341_PM_at | DNAJC3 | DnaJ (Hsp40) homolog, subfamily C, member 3 | 1.06E-05 | 21.8 | 22.1 | 35.0 |
| 9 | 1557733_PM_a_at | — | — | 1.21E-05 | 83.8 | 116.0 | 81.2 |
| 10 | 212906_PM_at | GRAMD1B | GRAM domain containing 1B | 1.26E-05 | 52.7 | 51.0 | 45.7 |
| 11 | 1555874_PM_x_at | MGC21881 | hypothetical locus MGC21881 | 1.53E-05 | 20.5 | 20.0 | 19.3 |
| 12 | 227645_PM_at | PIK3R5 | phosphoinositide-3-kinase, regulatory subunit 5 | 1.66E-05 | 948.4 | 824.5 | 1013.0 |
| 13 | 235744_PM_at | PPTC7 | PTC7 protein phosphatase homolog (*S. cerevisiae*) | 1.73E-05 | 21.3 | 18.0 | 25.7 |
| 14 | 1553873_PM_at | KLHL34 | kelch-like 34 (*Drosophila*) | 1.89E-05 | 11.1 | 12.1 | 9.9 |
| 15 | 218408_PM_at | TIMM10 | translocase of inner mitochondrial membrane 10 homolog (yeast) | 2.16E-05 | 125.9 | 137.7 | 99.4 |
| 16 | 227486_PM_at | NT5E | 5'-nucleotidase, ecto (CD73) | 2.46E-05 | 14.7 | 18.6 | 15.6 |
| 17 | 231798_PM_at | NOG | noggin | 2.49E-05 | 17.0 | 25.9 | 15.1 |
| 18 | 205920_PM_at | SLC6A6 | solute carrier family 6 (neurotransmitter transporter, taurine), member 6 | 2.53E-05 | 25.9 | 25.0 | 39.3 |
| 19 | 222435_PM_s_at | UBE2J1 | ubiquitin-conjugating enzyme E2, J1 (UBC6 homolog, yeast) | 2.63E-05 | 212.6 | 292.4 | 324.0 |
| 20 | 207737_PM_at | — | — | 2.89E-05 | 8.2 | 8.5 | 8.6 |
| 21 | 209644_PM_x_at | CDKN2A | cyclin-dependent kinase inhibitor 2A (melanoma, p16, inhibits CDK4) | 2.91E-05 | 13.7 | 13.9 | 11.5 |
| 22 | 241661_PM_at | JMJD1C | jumonji domain containing 1C | 2.99E-05 | 18.4 | 21.9 | 34.8 |
| 23 | 202086_PM_at | MX1 | myxovirus (influenza virus) resistance 1, interferon-inducible protein p78 (mouse) | 3.04E-05 | 562.6 | 496.4 | 643.9 |
| 24 | 243819_PM_at | — | — | 3.11E-05 | 766.7 | 495.1 | 661.8 |
| 25 | 210524_PM_x_at | — | — | 3.12E-05 | 154.5 | 209.2 | 138.6 |
| 26 | 217714_PM_x_at | STMN1 | stathmin 1 | 3.39E-05 | 22.3 | 28.5 | 20.4 |
| 27 | 219659_PM_at | ATP8A2 | ATPase, aminophospholipid transporter, class I, type 8A, member 2 | 3.65E-05 | 10.4 | 10.8 | 9.8 |
| 28 | 219915_PM_s_at | SLC16A10 | solute carrier family 16, member 10 (aromatic amino acid transporter) | 3.70E-05 | 19.4 | 21.8 | 15.8 |
| 29 | 214039_PM_s_at | LAPTM4B | lysosomal protein transmembrane 4 beta | 3.81E-05 | 70.4 | 104.0 | 74.2 |
| 30 | 214107_PM_at | LOC440434 | aminopeptidase puromycin sensitive pseudogene | 4.27E-05 | 182.8 | 155.0 | 224.7 |
| 31 | 225408_PM_at | MBP | myelin basic protein | 4.54E-05 | 34.1 | 32.6 | 47.9 |
| 32 | 1552623_PM_at | HSH2D | hematopoietic SH2 domain containing | 4.93E-05 | 373.7 | 323.9 | 401.3 |
| 33 | 206974_PM_at | CXCR6 | chemokine (C-X-C motif) receptor 6 | 5.33E-05 | 24.6 | 31.0 | 22.9 |
| 34 | 203764_PM_at | DLGAP5 | discs, large (*Drosophila*) homolog-associated protein 5 | 5.41E-05 | 9.3 | 10.9 | 8.6 |
| 35 | 213915_PM_at | NKG7 | natural killer cell group 7 sequence | 5.73E-05 | 2603.1 | 1807.7 | 1663.1 |
| 36 | 1570597_PM_at | — | — | 5.86E-05 | 8.3 | 7.8 | 7.5 |
| 37 | 228290_PM_at | PLK1S1 | Polo-like kinase 1 substrate 1 | 6.00E-05 | 47.2 | 35.6 | 45.8 |
| 38 | 230753_PM_at | PATL2 | protein associated with topoisomerase II homolog 2 (yeast) | 6.11E-05 | 169.0 | 123.0 | 131.6 |
| 39 | 202016_PM_at | MEST | mesoderm specific transcript homolog (mouse) | 6.25E-05 | 18.3 | 27.5 | 17.3 |
| 40 | 212730_PM_at | SYNM | synemin, intermediate filament protein | 6.30E-05 | 16.7 | 19.5 | 14.4 |
| 41 | 209203_PM_s_at | BICD2 | bicaudal D homolog 2 (*Drosophila*) | 6.50E-05 | 197.8 | 177.0 | 256.6 |
| 42 | 1554397_PM_s_at | UEVLD | UEV and lactate/malate dehydrogenase domains | 6.59E-05 | 20.8 | 17.7 | 25.2 |
| 43 | 217963_PM_s_at | NGFRAP1 | nerve growth factor receptor (TNFRSF16) associated protein 1 | 7.61E-05 | 505.9 | 713.1 | 555.7 |
| 44 | 201656_PM_at | ITGA6 | integrin, alpha 6 | 7.75E-05 | 87.4 | 112.6 | 84.1 |
| 45 | 1553685_PM_s_at | SP1 | Sp1 transcription factor | 7.83E-05 | 27.4 | 27.3 | 41.3 |
| 46 | 236717_PM_at | FAM179A | family with sequence similarity 179, member A | 8.00E-05 | 55.1 | 39.8 | 42.1 |

TABLE 4-continued 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 47 | 240913_PM_at | FGFR2 | fibroblast growth factor receptor 2 | 8.33E-05 | 9.2 | 9.6 | 10.2 |
| 48 | 243756_PM_at | — | — | 8.47E-05 | 7.9 | 8.5 | 7.4 |
| 49 | 222036_PM_s_at | MCM4 | minichromosome maintenance complex component 4 | 8.52E-05 | 29.5 | 35.1 | 25.4 |
| 50 | 202644_PM_s_at | TNFAIP3 | tumor necrosis factor, alpha-induced protein 3 | 8.57E-05 | 516.0 | 564.5 | 475.8 |
| 51 | 229625_PM_at | GBP5 | guanylate binding protein 5 | 9.23E-05 | 801.9 | 1014.7 | 680.8 |
| 52 | 235545_PM_at | DEPDC1 | DEP domain containing 1 | 9.83E-05 | 8.0 | 8.7 | 8.3 |
| 53 | 204641_PM_at | NEK2 | NIMA (never in mitosis gene a)-related kinase 2 | 0.000100269 | 10.2 | 12.5 | 10.0 |
| 54 | 213931_PM_at | ID2 /// ID2B | inhibitor of DNA binding 2, dominant negative helix-loop-helix protein /// inhibitor of | 0.000101645 | 562.9 | 504.9 | 384.6 |
| 55 | 216125_PM_s_at | RANBP9 | RAN binding protein 9 | 0.000102366 | 35.4 | 37.0 | 50.3 |
| 56 | 205660_PM_at | OASL | 2'-5'-oligoadenylate synthetase-like | 0.000102776 | 470.5 | 394.6 | 493.4 |
| 57 | 222816_PM_s_at | ZCCHC2 | zinc finger, CCHC domain containing 2 | 0.000105861 | 301.3 | 308.7 | 320.8 |
| 58 | 1554696_PM_s_at | TYMS | thymidylate synthetase | 0.000110478 | 11.1 | 16.2 | 11.2 |
| 59 | 232229_PM_at | SETX | senataxin | 0.000113076 | 44.2 | 34.5 | 48.7 |
| 60 | 204929_PM_s_at | VAMP5 | vesicle-associated membrane protein 5 (myobrevin) | 0.000113182 | 152.8 | 197.8 | 153.6 |
| 61 | 203819_PM_s_at | IGF2BP3 | insulin-like growth factor 2 mRNA binding protein 3 | 0.000113349 | 45.4 | 75.4 | 51.1 |
| 62 | 210164_PM_at | GZMB | granzyme B (granzyme 2, cytotoxic T-lymphocyte-associated serine esterase 1) | 0.000113466 | 955.2 | 749.5 | 797.1 |
| 63 | 202589_PM_at | TYMS | thymidylate synthetase | 0.000113758 | 50.0 | 85.8 | 44.4 |
| 64 | 240507_PM_at | — | — | 0.000116854 | 8.8 | 8.4 | 8.2 |
| 65 | 204475_PM_at | MMP1 | matrix metallopeptidase 1 (interstitial collagenase) | 0.000116902 | 9.2 | 15.4 | 9.6 |
| 66 | 222625_PM_s_at | NDE1 | nudE nuclear distribution gene E homolog 1 (A. nidulans) | 0.000119388 | 60.6 | 55.3 | 72.2 |
| 67 | 1562697_PM_at | LOC339988 | hypothetical LOC339988 | 0.000125343 | 145.2 | 97.8 | 105.4 |
| 68 | 218662_PM_s_at | NCAPG | non-SMC condensin I complex, subunit G | 0.000129807 | 11.5 | 14.8 | 10.7 |
| 69 | 201212_PM_at | LGMN | legumain | 0.000129933 | 15.4 | 18.9 | 14.2 |
| 70 | 236191_PM_at | — | — | 0.000133129 | 83.4 | 71.0 | 76.6 |
| 71 | 33736_PM_at | STOML1 | stomatin (EPB72)-like 1 | 0.000137232 | 44.9 | 47.9 | 37.4 |
| 72 | 221695_PM_s_at | MAP3K2 | mitogen-activated protein kinase kinase kinase 2 | 0.000139287 | 76.4 | 76.8 | 130.8 |
| 73 | 241692_PM_at | — | — | 0.000142595 | 57.5 | 44.8 | 61.8 |
| 74 | 218741_PM_at | CENPM | centromere protein M | 0.000142617 | 13.5 | 15.9 | 12.3 |
| 75 | 220684_PM_at | TBX21 | T-box 21 | 0.00014693 | 272.6 | 169.0 | 182.2 |
| 76 | 233700_PM_at | — | — | 0.000148072 | 125.7 | 74.1 | 156.3 |
| 77 | 217336_PM_at | RPS10 /// RPS10P7 | ribosomal protein S10 /// ribosomal protein S10 pseudogene 7 | 0.000149318 | 76.4 | 93.5 | 63.0 |
| 78 | 224391_PM_s_at | SIAE | sialic acid acetylesterase | 0.000152602 | 28.8 | 42.0 | 33.8 |
| 79 | 201220_PM_x_at | CTBP2 | C-terminal binding protein 2 | 0.000155512 | 1316.8 | 1225.6 | 1516.2 |
| 80 | 204589_PM_at | NUAK1 | NUAK family, SNF1-like kinase, 1 | 0.000155593 | 13.1 | 10.1 | 9.6 |
| 81 | 1565254_PM_s_at | ELL | elongation factor RNA polymerase II | 0.000157726 | 29.2 | 24.5 | 40.4 |
| 82 | 243362_PM_s_at | LOC641518 | hypothetical LOC641518 | 0.000159096 | 14.3 | 21.1 | 13.5 |
| 83 | 219288_PM_at | C3orf14 | chromosome 3 open reading frame 14 | 0.000162164 | 31.1 | 43.4 | 28.0 |
| 84 | 210797_PM_s_at | OASL | 2'-5'-oligoadenylate synthetase-like | 0.000167239 | 268.3 | 219.6 | 304.2 |
| 85 | 243917_PM_at | CLIC5 | chloride intracellular channel 5 | 0.00017077 | 10.9 | 9.6 | 10.5 |
| 86 | 237538_PM_at | — | — | 0.000176359 | 18.4 | 21.3 | 18.0 |
| 87 | 207926_PM_at | GP5 | glycoprotein V (platelet) | 0.000178057 | 17.3 | 19.3 | 15.7 |
| 88 | 204103_PM_at | CCL4 | chemokine (C-C motif) ligand 4 | 0.000178791 | 338.5 | 265.9 | 235.5 |
| 89 | 212843_PM_at | NCAM1 | neural cell adhesion molecule 1 | 0.000180762 | 28.7 | 25.8 | 33.5 |
| 90 | 213629_PM_x_at | MT1F | metallothionein 1F | 0.000186273 | 268.3 | 348.4 | 234.3 |
| 91 | 212687_PM_at | LIMS1 | LIM and senescent cell antigen-like domains 1 | 0.000188224 | 859.6 | 1115.2 | 837.3 |
| 92 | 242898_PM_at | EIF2AK2 | eukaryotic translation initiation factor 2-alpha kinase 2 | 0.000189906 | 82.5 | 66.4 | 81.2 |
| 93 | 208228_PM_s_at | FGFR2 | fibroblast growth factor receptor 2 | 0.000194281 | 8.9 | 11.1 | 8.7 |

TABLE 4-continued 263 probesets for distinguishing between AR, ADNR and TX in Liver PAXgene samples

| # | Probeset ID | Gene Symbol | Gene Title | p-value (Phenotype) | ADNR-Mean | AR-Mean | TX-Mean |
|---|---|---|---|---|---|---|---|
| 94 | 219386_PM_s_at | SLAMF8 | SLAM family member 8 | 0.000195762 | 18.6 | 23.0 | 16.5 |
| 95 | 201470_PM_at | GSTO1 | glutathione S-transferase omega 1 | 0.000200503 | 1623.3 | 1902.3 | 1495.5 |
| 96 | 204326_PM_x_at | MT1X | metallothionein 1X | 0.000202494 | 370.5 | 471.8 | 313.0 |
| 97 | 213996_PM_at | YPEL1 | yippee-like 1 (*Drosophila*) | 0.000202959 | 48.9 | 37.9 | 40.4 |
| 98 | 203820_PM_s_at | IGF2BP3 | insulin-like growth factor 2 mRNA binding protein 3 | 0.000210022 | 21.8 | 35.5 | 23.2 |
| 99 | 218599_PM_at | REC8 | REC8 homolog (yeast) | 0.000216761 | 42.6 | 43.3 | 41.1 |
| 100 | 216836_PM_s_at | ERBB2 | v-erb-b2 erythroblastic leukemia viral oncogene homolog 2, neuro/glioblastoma derived o | 0.000217714 | 14.6 | 12.0 | 12.9 |
| 101 | 213258_PM_at | TFPI | tissue factor pathway inhibitor (lipoprotein-associated coagulation inhibitor) | 0.000218458 | 13.6 | 24.6 | 14.2 |
| 102 | 212859_PM_x_at | MT1E | metallothionein 1E | 0.000218994 | 166.9 | 238.1 | 134.5 |
| 103 | 214617_PM_at | PRF1 | perforin 1 (pore forming protein) | 0.000222846 | 1169.2 | 822.3 | 896.0 |
| 104 | 38918_PM_at | SOX13 | SRY (sex determining region Y)-box 13 | 0.000223958 | 14.1 | 10.9 | 11.8 |
| 105 | 209969_PM_s_at | STAT1 | signal transducer and activator of transcription 1, 91 kDa | 0.000225534 | 1707.4 | 1874.3 | 1574.4 |
| 106 | 205909_PM_at | POLE2 | polymerase (DNA directed), epsilon 2 (p59 subunit) | 0.000226803 | 14.0 | 16.0 | 12.7 |
| 107 | 205612_PM_at | MMRN1 | multimerin 1 | 0.000227425 | 10.3 | 15.5 | 11.1 |
| 108 | 218400_PM_at | OAS3 | 2'-5'-oligoadenylate synthetase 3, 100 kDa | 0.000231476 | 142.6 | 125.9 | 170.8 |
| 109 | 202503_PM_s_at | KIAA0101 | KIAA0101 | 0.000231183 | 34.4 | 65.8 | 25.5 |
| 110 | 225636_PM_at | STAT2 | signal transducer and activator of transcription 2, 113 kDa | 0.000234463 | 1425.0 | 1422.9 | 1335.1 |
| 111 | 226579_PM_at | — | — | 0.000234844 | 97.7 | 81.1 | 104.6 |
| 112 | 1555764_PM_s_at | TIMM10 | translocase of inner mitochondrial membrane 10 homolog (yeast) | 0.000235756 | 195.6 | 204.3 | 158.7 |
| 113 | 218429_PM_s_at | C19orf66 | chromosome 19 open reading frame 66 | 0.00024094 | 569.9 | 524.1 | 527.4 |
| 114 | 242155_PM_s_at | RFFL | ring finger and FYVE-like domain containing 1 | 0.000244391 | 62.8 | 46.7 | 72.0 |
| 115 | 1556643_PM_at | FAM125A | Family with sequence similarity 125, member A | 0.000244814 | 173.2 | 181.8 | 181.2 |
| 116 | 201957_PM_at | PPP1R12B | protein phosphatase 1, regulatory (inhibitor) subunit 12B | 0.000246874 | 93.3 | 63.9 | 107.9 |
| 117 | 219716_PM_at | APOL6 | apolipoprotein L, 6 | 0.000248621 | 86.0 | 95.2 | 79.1 |
| 118 | 1554206_PM_at | TMLHE | trimethyllysine hydroxylase, epsilon | 0.00026882 | 45.3 | 41.0 | 53.4 |
| 119 | 207795_PM_s_at | KLRD1 | killer cell lectin-like receptor subfamily D, member 1 | 0.000271145 | 294.6 | 201.8 | 192.5 |
| 120 | 210756_PM_s_at | NOTCH2 | notch 2 | 0.000271193 | 94.0 | 99.4 | 142.6 |
| 121 | 219815_PM_at | GAL3ST4 | galactose-3-O-sulfotransferase 4 | 0.00027183 | 17.3 | 19.9 | 16.4 |
| 122 | 230405_PM_at | C5orf56 | chromosome 5 open reading frame 56 | 0.000279441 | 569.5 | 563.2 | 521.9 |
| 123 | 228617_PM_at | XAF1 | XIAP associated factor 1 | 0.000279625 | 1098.8 | 1162.1 | 1043.0 |
| 124 | 240733_PM_at | — | — | 0.000281133 | 87.3 | 54.9 | 81.2 |
| 125 | 209773_PM_s_at | RRM2 | ribonucleotide reductase M2 | 0.000281144 | 48.7 | 88.2 | 40.4 |
| 126 | 219236_PM_at | PICALM | phosphatidylinositol binding clathrin assembly protein | 0.000284863 | 61.6 | 65.8 | 113.8 |
| 127 | 229534_PM_at | ACOT4 | acyl-CoA thioesterase 4 | 0.000286097 | 17.1 | 13.2 | 12.6 |
| 128 | 215177_PM_s_at | ITGA6 | integrin, alpha 6 | 0.000287492 | 35.2 | 44.2 | 34.0 |
| 129 | 210321_PM_at | GZMH | granzyme H (cathepsin G-like 2, protein h-CCPX) | 0.000293732 | 1168.2 | 616.6 | 532.0 |
| 130 | 206194_PM_at | HOXC4 | homeobox C4 | 0.000307767 | 20.0 | 17.1 | 15.1 |
| 131 | 214115_PM_at | VAMP5 | Vesicle-associated membrane protein 5 (myobrevin) | 0.000308837 | 11.8 | 13.2 | 12.2 |
| 132 | 211102_PM_s_at | LILRA2 | leukocyte immunoglobulin-like receptor, subfamily A (with TM domain), member 2 | 0.000310388 | 94.3 | 78.0 | 129.0 |
| 133 | 201818_PM_at | LPCAT1 | lysophosphatidylcholine acyltransferase 1 | 0.000311597 | 662.1 | 517.3 | 651.3 |
| 134 | 53720_PM_at | C19orf66 | chromosome 19 open reading frame 66 | 0.000311821 | 358.7 | 323.7 | 319.7 |
| 135 | 221648_PM_s_at | LOC100507192 | hypothetical LOC100507192 | 0.000312201 | 68.4 | 96.2 | 56.1 |
| 136 | 236899_PM_at | — | — | 0.000318309 | 9.8 | 10.5 | 8.8 |
| 137 | 220467_PM_at | — | — | 0.000319714 | 205.5 | 124.9 | 201.6 |
| 138 | 218638_PM_s_at | SPON2 | spondin 2, extracellular matrix protein | 0.000320682 | 168.2 | 109.2 | 137.0 |
| 139 | 211287_PM_x_at | CSF2RA | colony stimulating factor 2 receptor, alpha, low-affinity (granulocyte-macrophage) | 0.00032758 | 173.0 | 150.9 | 224.0 |
| 140 | 222058_PM_at | — | — | 0.000332098 | 82.7 | 61.0 | 101.6 |

TABLE 4-continued 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 141 | 224428_PM_s_at | CDCA7 | cell division cycle associated 7 | 0.000332781 | 22.9 | 31.5 | 19.6 |
| 142 | 228675_PM_at | LOC100131733 | hypothetical LOC100131733 | 0.000346627 | 15.2 | 17.6 | 14.5 |
| 143 | 221248_PM_s_at | WHSC1L1 | Wolf-Hirschhorn syndrome candidate 1-like 1 | 0.000354663 | 25.6 | 26.9 | 33.0 |
| 144 | 227697_PM_at | SOCS3 | suppressor of cytokine signaling 3 | 0.000354764 | 103.6 | 192.4 | 128.8 |
| 145 | 240661_PM_at | LOC284475 | hypothetical protein LOC284475 | 0.000355764 | 79.3 | 53.9 | 89.5 |
| 146 | 204886_PM_at | PLK4 | polo-like kinase 4 | 0.000357085 | 8.9 | 11.8 | 8.9 |
| 147 | 216834_PM_at | RGS1 | regulator of G-protein signaling 1 | 0.00035762 | 12.4 | 19.6 | 11.4 |
| 148 | 234089_PM_at | — | — | 0.000359586 | 10.5 | 10.1 | 11.2 |
| 149 | 236817_PM_at | ADAT2 | adenosine deaminase, tRNA-specific 2, TAD2 homolog (S. cerevisiae) | 0.000362076 | 15.6 | 14.3 | 12.0 |
| 150 | 225349_PM_at | ZNF496 | zinc finger protein 496 | 0.000363116 | 11.7 | 12.0 | 10.4 |
| 151 | 219863_PM_at | HERC5 | hect domain and RLD 5 | 0.000365254 | 621.1 | 630.8 | 687.7 |
| 152 | 221985_PM_at | KLHL24 | kelch-like 24 (Drosophila) | 0.000374117 | 183.6 | 184.7 | 216.9 |
| 153 | 1552977_PM_a_at | CNPY3 | canopy 3 homolog (zebrafish) | 0.000378983 | 351.3 | 319.3 | 381.7 |
| 154 | 1552667_PM_a_at | SH2D3C | SH2 domain containing 3C | 0.000380655 | 67.1 | 55.5 | 82.8 |
| 155 | 223502_PM_s_at | TNFSF13B | tumor necrosis factor (ligand) superfamily, member 13b | 0.000387301 | 2713.6 | 3366.3 | 2999.3 |
| 156 | 235139_PM_at | GNGT2 | guanine nucleotide binding protein (G protein), gamma transducing activity polypeptide | 0.000389019 | 41.8 | 35.8 | 38.6 |
| 157 | 239979_PM_at | — | — | 0.000389245 | 361.6 | 375.0 | 282.8 |
| 158 | 211882_PM_x_at | FUT6 | fucosyltransferase 6 (alpha (1,3) fucosyltransferase) | 0.000392613 | 11.1 | 11.6 | 10.6 |
| 159 | 1562698_PM_x_at | LOC339988 | hypothetical LOC339988 | 0.000394736 | 156.3 | 108.5 | 117.0 |
| 160 | 201890_PM_at | RRM2 | ribonucleotide reductase M2 | 0.000397796 | 23.6 | 42.5 | 21.7 |
| 161 | 243349_PM_at | KIAA1324 | KIAA1324 | 0.000399335 | 15.4 | 12.8 | 20.2 |
| 162 | 243947_PM_at | — | — | 0.000399873 | 8.4 | 9.6 | 8.9 |
| 163 | 205483_PM_s_at | ISG15 | ISG15 ubiquitin-like modifier | 0.000409282 | 1223.6 | 1139.6 | 1175.7 |
| 164 | 202705_PM_at | CCNB2 | cyclin B2 | 0.000409541 | 14.7 | 20.9 | 13.8 |
| 165 | 210835_PM_s_at | CTBP2 | C-terminal binding protein 2 | 0.000419387 | 992.3 | 926.1 | 1150.4 |
| 166 | 210554_PM_s_at | CTBP2 | C-terminal binding protein 2 | 0.000429433 | 1296.5 | 1198.0 | 1519.5 |
| 167 | 207085_PM_x_at | CSF2RA | colony stimulating factor 2 receptor, alpha, low-affinity (granulocyte-macrophage) | 0.000439275 | 204.5 | 190.0 | 290.3 |
| 168 | 204205_PM_at | APOBEC3G | apolipoprotein B mRNA editing enzyme, catalytic polypeptide-like 3G | 0.000443208 | 1115.8 | 988.8 | 941.4 |
| 169 | 227394_PM_at | NCAM1 | neural cell adhesion molecule 1 | 0.000443447 | 19.1 | 19.4 | 25.3 |
| 170 | 1568943_PM_at | INPP5D | inositol polyphosphate-5-phosphatase, 145 kDa | 0.000450045 | 127.3 | 87.7 | 114.0 |
| 171 | 213932_PM_x_at | HLA-A | major histocompatibility complex, class I, A | 0.00045661 | 9270.0 | 9080.1 | 9711.9 |
| 172 | 226202_PM_at | ZNF398 | zinc finger protein 398 | 0.000457538 | 84.5 | 78.4 | 98.3 |
| 173 | 233675_PM_s_at | LOC374491 | TPTE and PTEN homologous inositol lipid phosphatase pseudogene | 0.000457898 | 8.8 | 8.1 | 8.5 |
| 174 | 220711_PM_at | — | — | 0.000458552 | 197.6 | 162.7 | 209.0 |
| 175 | 1552646_PM_at | IL11RA | interleukin 11 receptor, alpha | 0.000463237 | 18.9 | 15.9 | 19.6 |
| 176 | 227055_PM_at | METTL7B | methyltransferase like 7B | 0.000464226 | 11.1 | 15.0 | 11.8 |
| 177 | 223980_PM_s_at | SP110 | SP110 nuclear body protein | 0.000471467 | 1330.9 | 1224.3 | 1367.3 |
| 178 | 242367_PM_at | — | — | 0.000471796 | 9.1 | 10.5 | 9.6 |
| 179 | 218543_PM_s_at | PARP12 | poly (ADP-ribose) polymerase family, member 12 | 0.000476879 | 513.8 | 485.7 | 475.7 |
| 180 | 204972_PM_at | OAS2 | 2'-5'-oligoadenylate synthetase 2, 69/71 kDa | 0.000480934 | 228.5 | 215.8 | 218.7 |
| 181 | 205746_PM_s_at | ADAM17 | ADAM metallopeptidase domain 17 | 0.000480965 | 39.0 | 47.0 | 60.4 |
| 182 | 1570645_PM_at | — | — | 0.000482948 | 9.3 | 9.1 | 8.4 |
| 183 | 211286_PM_x_at | CSF2RA | colony stimulating factor 2 receptor, alpha, low-affinity (granulocyte-macrophage) | 0.000484313 | 261.3 | 244.7 | 345.6 |
| 184 | 1557545_PM_s_at | RNF165 | ring finger protein 165 | 0.000489377 | 17.4 | 15.4 | 18.3 |
| 185 | 236545_PM_at | — | — | 0.000491065 | 479.3 | 367.8 | 526.2 |
| 186 | 228280_PM_at | ZC3HAV1L | zinc finger CCCH-type, antiviral 1-like | 0.000495768 | 25.3 | 36.4 | 23.7 |
| 187 | 239798_PM_at | — | — | 0.000505865 | 43.9 | 63.7 | 48.8 |
| 188 | 208055_PM_s_at | HERC4 | hect domain and RLD 4 | 0.000507283 | 37.6 | 34.8 | 45.8 |

TABLE 4-continued 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 189 | 225692_PM_at | CAMTA1 | calmodulin binding transcription activator 1 | 0.000515621 | 244.8 | 308.6 | 245.1 |
| 190 | 210986_PM_s_at | TPM1 | tropomyosin 1 (alpha) | 0.000532739 | 344.0 | 379.1 | 391.9 |
| 191 | 205929_PM_at | GPA33 | glycoprotein A33 (transmembrane) | 0.00053619 | 18.3 | 21.8 | 16.7 |
| 192 | 242234_PM_at | XAF1 | XIAP associated factor 1 | 0.000537429 | 123.1 | 133.1 | 114.9 |
| 193 | 206113_PM_s_at | RAB5A | RAB5A, member RAS oncogene family | 0.000543933 | 77.5 | 73.0 | 111.4 |
| 194 | 242520_PM_at | C1orf228 | chromosome 1 open reading frame 228 | 0.000547685 | 30.4 | 42.5 | 29.4 |
| 195 | 229203_PM_at | B4GALNT3 | beta-1,4-N-acetyl-galactosaminyl transferase 3 | 0.000549855 | 9.1 | 9.0 | 9.7 |
| 196 | 201601_PM_x_at | IFITM1 | interferon induced transmembrane protein 1 (9-27) | 0.000554665 | 6566.1 | 7035.7 | 7016.0 |
| 197 | 221024_PM_s_at | SLC2A10 | solute carrier family 2 (facilitated glucose transporter), member 10 | 0.000559418 | 8.3 | 9.7 | 8.6 |
| 198 | 204439_PM_at | IFI44L | interferon-induced protein 44-like | 0.000570113 | 343.5 | 312.4 | 337.1 |
| 199 | 215894_PM_at | PTGDR | prostaglandin D2 receptor (DP) | 0.000571076 | 343.8 | 191.2 | 233.7 |
| 200 | 230846_PM_at | AKAP5 | A kinase (PRKA) anchor protein 5 | 0.000572655 | 10.7 | 10.9 | 9.6 |
| 201 | 210340_PM_s_at | CSF2RA | colony stimulating factor 2 receptor, alpha, low-affinity (granulocyte-macrophage) | 0.000572912 | 154.2 | 146.3 | 200.8 |
| 202 | 237240_PM_at | — | — | 0.000573343 | 9.4 | 10.7 | 9.4 |
| 203 | 223836_PM_at | FGFBP2 | fibroblast growth factor binding protein 2 | 0.000574294 | 792.6 | 432.4 | 438.4 |
| 204 | 233743_PM_x_at | S1PR5 | sphingosine-1-phosphate receptor 5 | 0.000577598 | 9.3 | 8.6 | 9.6 |
| 205 | 229254_PM_at | MFSD4 | major facilitator superfamily domain containing 4 | 0.000581119 | 9.4 | 11.0 | 9.3 |
| 206 | 243674_PM_at | LOC100240735 /// LOC401522 | hypothetical LOC100240735 /// hypothetical LOC401522 | 0.00058123 | 14.5 | 12.9 | 12.1 |
| 207 | 208116_PM_s_at | MAN1A1 | mannosidase, alpha, class 1A, member 1 | 0.000581644 | 34.4 | 39.1 | 55.0 |
| 208 | 222246_PM_at | — | — | 0.000584363 | 15.9 | 13.9 | 17.9 |
| 209 | 212659_PM_s_at | IL1RN | interleukin 1 receptor antagonist | 0.000592065 | 87.2 | 94.5 | 116.3 |
| 210 | 204070_PM_at | RARRES3 | retinoic acid receptor responder (tazarotene induced) 3 | 0.000597748 | 771.6 | 780.7 | 613.7 |
| 211 | 219364_PM_at | DHX58 | DEXH (Asp-Glu-X-His) box polypeptide 58 | 0.000599299 | 92.7 | 85.2 | 85.3 |
| 212 | 204747_PM_at | IFIT3 | interferon-induced protein with tetratricopeptide repeats 3 | 0.000601375 | 603.1 | 576.7 | 586.2 |
| 213 | 204258_PM_at | ENO1 | enolase 1, (alpha) | 0.000601726 | 9.0 | 9.3 | 10.5 |
| 214 | 210724_PM_at | EMR3 | egf-like module containing, mucin-like, hormone receptor-like 3 | 0.000609884 | 622.3 | 437.3 | 795.3 |
| 215 | 204211_PM_x_at | EIF2AK2 | eukaryotic translation initiation factor 2-alpha kinase 2 | 0.000611116 | 168.3 | 139.2 | 179.6 |
| 216 | 234975_PM_at | GSPT1 | G1 to S phase transition 1 | 0.000615027 | 16.6 | 16.3 | 21.4 |
| 217 | 228145_PM_s_at | ZNF398 | zinc finger protein 398 | 0.000620533 | 373.0 | 329.5 | 374.3 |
| 218 | 201565_PM_s_at | ID2 | inhibitor of DNA binding 2, dominant negative helix-loop-helix protein | 0.000627734 | 1946.2 | 1798.1 | 1652.9 |
| 219 | 226906_PM_s_at | ARHGAP9 | Rho GTPase activating protein 9 | 0.000630617 | 636.2 | 516.2 | 741.5 |
| 220 | 228412_PM_at | LOC643072 | hypothetical LOC643072 | 0.00064178 | 213.5 | 186.6 | 282.7 |
| 221 | 233957_PM_at | — | — | 0.000644277 | 33.2 | 24.7 | 40.1 |
| 222 | 221277_PM_s_at | PUS3 | pseudouridylate synthase 3 | 0.000649375 | 86.6 | 99.3 | 77.8 |
| 223 | 203911_PM_at | RAP1GAP | RAP1 GTPase activating protein | 0.000658389 | 106.6 | 40.1 | 116.1 |
| 224 | 219352_PM_at | HERC6 | hect domain and RLD 6 | 0.000659313 | 94.6 | 87.2 | 81.8 |
| 225 | 204994_PM_at | MX2 | myxovirus (influenza virus) resistance 2 (mouse) | 0.000663904 | 1279.3 | 1147.0 | 1329.9 |
| 226 | 227499_PM_at | FZD3 | frizzled homolog 3 (Drosophila) | 0.00066528 | 11.7 | 11.0 | 9.8 |
| 227 | 222930_PM_s_at | AGMAT | agmatine ureohydrolase (agmatinase) | 0.000665618 | 12.9 | 14.9 | 11.4 |
| 228 | 204575_PM_s_at | MMP19 | matrix metallopeptidase 19 | 0.000668161 | 9.6 | 9.3 | 9.9 |
| 229 | 221038_PM_at | — | — | 0.000671518 | 8.7 | 8.2 | 9.3 |
| 230 | 233425_PM_at | — | — | 0.000676591 | 76.4 | 70.6 | 77.9 |
| 231 | 228972_PM_at | LOC100306951 | hypothetical LOC100306951 | 0.000679857 | 77.8 | 84.0 | 60.0 |
| 232 | 1560999_PM_a_at | — | — | 0.000680202 | 9.8 | 10.6 | 10.7 |
| 233 | 225931_PM_s_at | RNF213 | ring finger protein 213 | 0.000685818 | 339.7 | 313.2 | 333.3 |
| 234 | 1559110_PM_at | — | — | 0.000686358 | 11.7 | 11.5 | 13.4 |
| 235 | 207538_PM_at | IL4 | interleukin 4 | 0.000697306 | 8.3 | 9.5 | 8.7 |

TABLE 4-continued 263 probesets for distinguishing between AR, ADNR and TX in Liver PAXgene samples

| # | Probeset ID | Gene Symbol | Gene Title | p-value (Phenotype) | ADNR - Mean | AR - Mean | TX - Mean |
|---|---|---|---|---|---|---|---|
| 236 | 210358_PM_x_at | GATA2 | GATA binding protein 2 | 0.000702179 | 22.8 | 30.8 | 16.8 |
| 237 | 236341_PM_at | CTLA4 | cytotoxic T-lymphocyte-associated protein 4 | 0.000706875 | 16.5 | 22.3 | 16.8 |
| 238 | 227416_PM_s_at | ZCRB1 | zinc finger CCHC-type and RNA binding motif 1 | 0.000708438 | 388.0 | 422.6 | 338.2 |
| 239 | 210788_PM_s_at | DHRS7 | dehydrogenase/reductase (SDR family) member 7 | 0.000719333 | 1649.6 | 1559.9 | 1912.3 |
| 240 | 213287_PM_s_at | KRT10 | keratin 10 | 0.000721676 | 557.8 | 585.1 | 439.3 |
| 241 | 204026_PM_s_at | ZWINT | ZW10 interactor | 0.000724993 | 23.3 | 31.1 | 19.9 |
| 242 | 239223_PM_s_at | FBXL20 | F-box and leucine-rich repeat protein 20 | 0.000733241 | 106.8 | 75.0 | 115.9 |
| 243 | 234196_PM_at | — | — | 0.000742539 | 140.6 | 81.3 | 162.4 |
| 244 | 214931_PM_s_at | SRPK2 | SRSF protein kinase 2 | 0.000747767 | 30.0 | 30.9 | 45.3 |
| 245 | 216907_PM_x_at | KIR3DL1 /// KIR3DL2 /// LOC727787 | killer cell immunoglobulin-like receptor, three domains, long cytoplasmic tail, 1 /// k | 0.000748056 | 18.8 | 12.6 | 13.8 |
| 246 | 243802_PM_at | DNAH12 | dynein, axonemal, heavy chain 12 | 0.000751054 | 8.8 | 9.9 | 8.4 |
| 247 | 212070_PM_at | GPR56 | G protein-coupled receptor 56 | 0.000760168 | 338.8 | 177.5 | 198.1 |
| 248 | 239185_PM_at | ABCA9 | ATP-binding cassette, sub-family A (ABC1), member 9 | 0.000767347 | 8.3 | 9.0 | 9.8 |
| 249 | 229597_PM_s_at | WDFY4 | WDFY family member 4 | 0.000769378 | 128.9 | 96.6 | 148.4 |
| 250 | 216243_PM_s_at | IL1RN | interleukin 1 receptor antagonist | 0.000770819 | 131.4 | 134.1 | 180.7 |
| 251 | 206991_PM_s_at | CCR5 | chemokine (C-C motif) receptor 5 | 0.000771059 | 128.5 | 128.6 | 110.5 |
| 252 | 219385_PM_at | SLAMF8 | SLAM family member 8 | 0.000789607 | 13.8 | 13.2 | 11.3 |
| 253 | 240438_PM_at | — | — | 0.000801737 | 10.8 | 10.4 | 11.4 |
| 254 | 226303_PM_at | PGM5 | phosphoglucomutase 5 | 0.000802853 | 11.9 | 12.6 | 24.2 |
| 255 | 205875_PM_s_at | TREX1 | three prime repair exonuclease 1 | 0.000804871 | 254.9 | 251.6 | 237.6 |
| 256 | 1566201_PM_at | — | — | 0.000809569 | 10.4 | 9.0 | 10.2 |
| 257 | 211230_PM_s_at | PIK3CD | phosphoinositide-3-kinase, catalytic, delta polypeptide | 0.000812288 | 20.4 | 20.3 | 24.6 |
| 258 | 202566_PM_s_at | SVIL | supervillin | 0.000819718 | 43.9 | 41.0 | 67.5 |
| 259 | 244846_PM_at | — | — | 0.000821386 | 75.0 | 55.1 | 84.9 |
| 260 | 208436_PM_s_at | IRF7 | interferon regulatory factor 7 | 0.000826426 | 264.0 | 262.4 | 281.2 |
| 261 | 242020_PM_s_at | ZBP1 | Z-DNA binding protein 1 | 0.000828174 | 87.9 | 83.1 | 102.5 |
| 262 | 203779_PM_s_at | MPZL2 | myelin protein zero-like 2 | 0.000830222 | 10.4 | 10.0 | 12.9 |
| 263 | 212458_PM_at | SPRED2 | sprouty-related, EVH1 domain containing 2 | 0.000833211 | 11.5 | 11.4 | 13.4 |

TABLE 5

147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 1 | 241038_PM_at | — | — | 4.76E-08 | 21.0 | 13.2 | 13.9 |
| 2 | 207737_PM_at | — | — | 5.33E-06 | 8.5 | 8.4 | 10.2 |
| 3 | 1557733_PM_a_at | — | — | 6.19E-06 | 116.0 | 50.8 | 64.5 |
| 4 | 228290_PM_at | PLK1S1 | Polo-like kinase 1 substrate 1 | 7.97E-06 | 35.6 | 48.1 | 48.5 |
| 5 | 231798_PM_at | NOG | noggin | 8.34E-06 | 25.9 | 12.6 | 9.4 |
| 6 | 214039_PM_s_at | LAPTM4B | lysosomal protein transmembrane 4 beta | 9.49E-06 | 104.0 | 58.3 | 68.5 |
| 7 | 241692_PM_at | — | — | 9.61E-06 | 44.8 | 65.1 | 78.4 |
| 8 | 230776_PM_at | — | — | 1.21E-05 | 13.7 | 10.4 | 9.5 |
| 9 | 217963_PM_s_at | NGFRAP1 | nerve growth factor receptor (TNFRSF16) associated protein 1 | 1.56E-05 | 713.1 | 461.2 | 506.6 |
| 10 | 243917_PM_at | CLIC5 | chloride intracellular channel 5 | 1.67E-05 | 9.6 | 10.9 | 11.6 |
| 11 | 219915_PM_s_at | SLC16A10 | solute carrier family 16, member 10 (aromatic amino acid transporter) | 1.77E-05 | 21.8 | 13.2 | 12.5 |
| 12 | 1553873_PM_at | KLHL34 | kelch-like 34 (Drosophila) | 1.85E-05 | 12.1 | 9.6 | 9.1 |
| 13 | 227645_PM_at | PIK3R5 | phosphoinositide-3-kinase, regulatory subunit 5 | 2.12E-05 | 824.5 | 1003.6 | 1021.4 |
| 14 | 1552623_PM_at | HSH2D | hematopoietic SH2 domain containing | 2.54E-05 | 323.9 | 497.5 | 445.4 |
| 15 | 227486_PM_at | NT5E | 5'-nucleotidase, ecto (CD73) | 2.66E-05 | 18.6 | 13.4 | 12.2 |
| 16 | 219659_PM_at | ATP8A2 | ATPase, aminophospholipid transporter, class I, type 8A, member 2 | 4.00E-05 | 10.8 | 9.0 | 8.9 |
| 17 | 1555874_PM_x_at | MGC21881 | hypothetical locus MGC21881 | 4.16E-05 | 20.0 | 21.0 | 31.4 |
| 18 | 202086_PM_at | MX1 | myxovirus (influenza virus) resistance 1, interferon-inducible protein p78 (mouse) | 4.52E-05 | 496.4 | 1253.1 | 1074.1 |
| 19 | 233675_PM_s_at | LOC374491 | TPTE and PTEN homologous inositol lipid phosphatase pseudogene | 4.85E-05 | 8.1 | 8.2 | 9.9 |
| 20 | 219815_PM_at | GAL3ST4 | galactose-3-O-sulfotransferase 4 | 5.37E-05 | 19.9 | 17.0 | 14.3 |
| 21 | 242898_PM_at | EIF2AK2 | eukaryotic translation initiation factor 2-alpha kinase 2 | 6.06E-05 | 66.4 | 116.6 | 108.7 |
| 22 | 215177_PM_s_at | ITGA6 | integrin, alpha 6 | 6.39E-05 | 44.2 | 26.9 | 23.9 |
| 23 | 236717_PM_at | FAM179A | family with sequence similarity 179, member A | 6.43E-05 | 39.8 | 51.3 | 73.3 |
| 24 | 242520_PM_at | C1orf228 | chromosome 1 open reading frame 228 | 6.67E-05 | 42.5 | 29.1 | 26.4 |
| 25 | 207926_PM_at | GP5 | glycoprotein V (platelet) | 7.03E-05 | 19.3 | 14.7 | 16.0 |
| 26 | 211882_PM_x_at | FUT6 | fucosyltransferase 6 (alpha (1,3) fucosyltransferase) | 8.11E-05 | 11.6 | 9.8 | 10.7 |
| 27 | 201656_PM_at | ITGA6 | integrin, alpha 6 | 8.91E-05 | 112.6 | 69.0 | 70.7 |
| 28 | 233743_PM_x_at | S1PR5 | sphingosine-1-phosphate receptor 5 | 9.26E-05 | 8.6 | 10.1 | 9.2 |
| 29 | 210797_PM_s_at | OASL | 2'-5'-oligoadenylate synthetase-like | 9.28E-05 | 219.6 | 497.2 | 446.0 |
| 30 | 243819_PM_at | — | — | 9.55E-05 | 495.1 | 699.2 | 769.8 |
| 31 | 209728_PM_at | HLA-DRB4 /// LOC100509582 | major histocompatibility complex, class II, DR beta 4 /// HLA class II histocompatibili | 0.000102206 | 33.8 | 403.5 | 55.2 |
| 32 | 218638_PM_s_at | SPON2 | spondin 2, extracellular matrix protein | 0.000103572 | 109.2 | 215.7 | 187.9 |
| 33 | 224293_PM_at | TTTY10 | testis-specific transcript, Y-linked 10 (non-protein coding) | 0.000103782 | 8.7 | 11.1 | 10.2 |
| 34 | 205660_PM_at | OASL | 2'-5'-oligoadenylate synthetase-like | 0.000105267 | 394.6 | 852.0 | 878.1 |
| 35 | 230753_PM_at | PATL2 | protein associated with topoisomerase II homolog 2 (yeast) | 0.00010873 | 123.0 | 168.6 | 225.2 |
| 36 | 243362_PM_s_at | LOC641518 | hypothetical LOC641518 | 0.000114355 | 21.1 | 13.1 | 11.2 |
| 37 | 213996_PM_at | YPEL1 | yippee-like 1 (Drosophila) | 0.00012688 | 37.9 | 55.8 | 59.5 |
| 38 | 232222_PM_at | C18orf49 | chromosome 18 open reading frame 49 | 0.000129064 | 35.7 | 65.1 | 53.0 |
| 39 | 205612_PM_at | MMRN1 | multimerin 1 | 0.000142028 | 15.5 | 9.9 | 11.2 |
| 40 | 214791_PM_at | SP140L | SP140 nuclear body protein-like | 0.000150108 | 223.4 | 278.8 | 285.8 |
| 41 | 240507_PM_at | — | — | 0.000152167 | 8.4 | 9.5 | 8.1 |
| 42 | 203819_PM_s_at | IGF2BP3 | insulin-like growth factor 2 mRNA binding protein 3 | 0.000174054 | 75.4 | 45.9 | 62.4 |
| 43 | 219288_PM_at | C3orf14 | chromosome 3 open reading frame 14 | 0.000204911 | 43.4 | 29.2 | 51.0 |
| 44 | 214376_PM_at | — | — | 0.000213039 | 8.9 | 9.6 | 8.1 |

TABLE 5-continued 147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 45 | 1568609_PM_s_at | FAM91A2 /// FLJ39739 /// LOC100286793 /// LOC728855 /// LOC728875 | family with sequence similarity 91, member A2 /// hypothetical FLJ39739 /// hypothetica | 0.000218802 | 378.6 | 472.7 | 427.1 |
| 46 | 207538_PM_at | IL4 | interleukin 4 | 0.000226354 | 9.5 | 8.3 | 8.9 |
| 47 | 243947_PM_s_at | — | — | 0.000227289 | 9.6 | 8.4 | 8.6 |
| 48 | 204211_PM_x_at | EIF2AK2 | eukaryotic translation initiation factor 2-alpha kinase 2 | 0.000227971 | 139.2 | 222.0 | 225.5 |
| 49 | 221648_PM_s_at | LOC100507192 | hypothetical LOC100507192 | 0.000230544 | 96.2 | 62.4 | 62.1 |
| 50 | 202016_PM_at | MEST | mesoderm specific transcript homolog (mouse) | 0.000244181 | 27.5 | 17.0 | 19.3 |
| 51 | 220684_PM_at | TBX21 | T-box 21 | 0.000260563 | 169.0 | 279.9 | 309.1 |
| 52 | 219018_PM_s_at | CCDC85C | coiled-coil domain containing 85C | 0.000261452 | 14.9 | 17.1 | 17.1 |
| 53 | 204575_PM_s_at | MMP19 | matrix metallopeptidase 19 | 0.00026222 | 9.3 | 9.3 | 11.3 |
| 54 | 1568943_PM_s_at | INPP5D | inositol polyphosphate-5-phosphatase, 145 kDa | 0.000265939 | 87.7 | 143.4 | 133.5 |
| 55 | 220467_PM_at | — | — | 0.000269919 | 124.9 | 215.2 | 206.0 |
| 56 | 207324_PM_s_at | DSC1 | desmocollin 1 | 0.000280239 | 14.5 | 11.3 | 10.3 |
| 57 | 218400_PM_at | OAS3 | 2'-5'-oligoadenylate synthetase 3, 100 kDa | 0.000288454 | 125.9 | 316.7 | 299.6 |
| 58 | 214617_PM_at | PRF1 | perforin 1 (pore forming protein) | 0.000292417 | 822.3 | 1327.9 | 1415.4 |
| 59 | 239798_PM_at | — | — | 0.000294263 | 63.7 | 39.1 | 35.3 |
| 60 | 242020_PM_s_at | ZBP1 | Z-DNA binding protein 1 | 0.000303843 | 83.1 | 145.8 | 128.5 |
| 61 | 201786_PM_s_at | ADAR | adenosine deaminase, RNA-specific | 0.000305042 | 2680.0 | 3340.9 | 3194.2 |
| 62 | 234974_PM_at | GALM | galactose mutarotase (aldose 1-epimerase) | 0.000308107 | 63.1 | 88.8 | 93.7 |
| 63 | 233121_PM_at | — | — | 0.000308702 | 17.8 | 23.8 | 19.4 |
| 64 | 1557545_PM_s_at | RNF165 | ring finger protein 165 | 0.000308992 | 15.4 | 24.2 | 22.1 |
| 65 | 229203_PM_at | B4GALNT3 | beta-1,4-N-acetyl-galactosaminyl transferase 3 | 0.000309508 | 9.0 | 10.1 | 8.6 |
| 66 | 210164_PM_at | GZMB | granzyme B (granzyme 2, cytotoxic T-lymphocyte-associated serine esterase 1) | 0.000332925 | 749.5 | 1241.7 | 1374.7 |
| 67 | 222468_PM_at | KIAA0319L | KIAA0319-like | 0.000327428 | 286.7 | 396.3 | 401.1 |
| 68 | 223272_PM_s_at | C1orf57 | chromosome 1 open reading frame 57 | 0.000342477 | 69.0 | 54.6 | 77.4 |
| 69 | 240913_PM_at | FGFR2 | fibroblast growth factor receptor 2 | 0.00035107 | 9.6 | 10.6 | 11.7 |
| 70 | 230854_PM_at | BCAR4 | breast cancer anti-estrogen resistance 4 | 0.000352682 | 10.2 | 10.2 | 8.9 |
| 71 | 1562697_PM_at | LOC339988 | hypothetical LOC339988 | 0.000360155 | 97.8 | 151.3 | 142.0 |
| 72 | 222732_PM_at | TRIM39 | tripartite motif-containing 39 | 0.000372812 | 115.6 | 135.8 | 115.4 |
| 73 | 227917_PM_at | FAM85A /// FAM85B | family with sequence similarity 85, member A /// family with sequence similarity 85, me | 0.000373226 | 206.8 | 154.1 | 154.9 |
| 74 | 212687_PM_at | LIMS1 | LIM and senescent cell antigen-like domains 1 | 0.000383722 | 1115.2 | 824.0 | 913.2 |
| 75 | 216836_PM_s_at | ERBB2 | v-erb-b2 erythroblastic leukemia viral oncogene homolog 2, neuro/glioblastoma derived o | 0.000384613 | 12.0 | 16.3 | 14.3 |
| 76 | 236191_PM_at | — | — | 0.000389259 | 71.0 | 95.0 | 114.3 |
| 77 | 213932_PM_x_at | HLA-A | major histocompatibility complex, class I, A | 0.000391535 | 9080.1 | 10344.2 | 10116.9 |
| 78 | 229254_PM_at | MFSD4 | major facilitator superfamily domain containing 4 | 0.000393739 | 11.0 | 9.0 | 9.5 |
| 79 | 212843_PM_at | NCAM1 | neural cell adhesion molecule 1 | 0.000401596 | 25.8 | 50.2 | 37.7 |
| 80 | 235256_PM_s_at | GALM | galactose mutarotase (aldose 1-epimerase) | 0.000417617 | 58.0 | 79.8 | 90.2 |
| 81 | 1566201_PM_at | — | — | 0.000420058 | 9.0 | 10.3 | 8.8 |
| 82 | 204994_PM_at | MX2 | myxovirus (influenza virus) resistance 2 (mouse) | 0.000438751 | 1147.0 | 1669.1 | 1518.5 |
| 83 | 237240_PM_at | — | — | 0.000440008 | 10.7 | 9.2 | 9.1 |
| 84 | 232478_PM_at | — | — | 0.000447263 | 51.3 | 96.8 | 71.5 |

TABLE 5-continued 147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 85 | 211410_PM_x_at | KIR2DL5A | killer cell immunoglobulin-like receptor, two domains, long cytoplasmic tail, 5A | 0.00045859 | 24.8 | 31.7 | 39.0 |
| 86 | 1569551_PM_at | — | — | 0.00045899 | 12.7 | 17.5 | 17.9 |
| 87 | 222816_PM_s_at | ZCCHC2 | zinc finger, CCHC domain containing 2 | 0.00046029 | 308.7 | 502.0 | 404.6 |
| 88 | 1557071_PM_s_at | NUB1 | negative regulator of ubiquitin-like proteins 1 | 0.000481473 | 108.5 | 144.0 | 155.3 |
| 89 | 219170_PM_at | PCDH9 | protocadherin 9 | 0.000485253 | 37.9 | 76.4 | 66.9 |
| 90 | 230563_PM_at | RASGEF1A | RasGEF domain family, member 1A | 0.000488148 | 86.8 | 121.7 | 139.4 |
| 91 | 1560080_PM_at | — | — | 0.000488309 | 9.9 | 11.0 | 12.2 |
| 92 | 243756_PM_at | — | — | 0.000488867 | 8.5 | 7.5 | 8.2 |
| 93 | 212730_PM_at | SYNM | synemin, intermediate filament protein | 0.000521028 | 19.5 | 15.7 | 27.7 |
| 94 | 1552977_PM_a_at | CNPY3 | canopy 3 homolog (zebrafish) | 0.000521239 | 319.3 | 395.2 | 261.4 |
| 95 | 218657_PM_at | RAPGEFL1 | Rap guanine nucleotide exchange factor (GEF)-like 1 | 0.000529963 | 10.4 | 11.9 | 11.5 |
| 96 | 228139_PM_at | RIPK3 | receptor-interacting serine-threonine kinase 3 | 0.000530418 | 87.8 | 107.4 | 102.7 |
| 97 | 38918_PM_at | SOX13 | SRY (sex determining region Y)-box 13 | 0.000534735 | 10.9 | 13.1 | 13.1 |
| 98 | 207795_PM_s_at | KLRD1 | killer cell lectin-like receptor subfamily D, member 1 | 0.000538523 | 201.8 | 309.8 | 336.1 |
| 99 | 212906_PM_at | GRAMD1B | GRAM domain containing 1B | 0.000540879 | 51.0 | 58.3 | 78.1 |
| 100 | 1561098_PM_at | LOC641365 | hypothetical LOC641365 | 0.000541122 | 8.7 | 8.5 | 10.1 |
| 101 | 209593_PM_s_at | TOR1B | torsin family 1, member B (torsin B) | 0.000542383 | 271.7 | 392.9 | 408.3 |
| 102 | 223980_PM_s_at | SP110 | SP110 nuclear body protein | 0.000543351 | 1224.3 | 1606.9 | 1561.2 |
| 103 | 1554206_PM_at | TMLHE | trimethyllysine hydroxylase, epsilon | 0.000545869 | 41.0 | 50.6 | 46.5 |
| 104 | 240438_PM_at | — | — | 0.000555441 | 10.4 | 12.0 | 13.1 |
| 105 | 212190_PM_at | SERPINE2 | serpin peptidase inhibitor, clade E (nexin, plasminogen activator inhibitor type 1), me | 0.00055869 | 25.8 | 18.3 | 21.4 |
| 106 | 202081_PM_at | IER2 | immediate early response 2 | 0.000568285 | 1831.1 | 2155.1 | 1935.4 |
| 107 | 234089_PM_at | — | — | 0.000585869 | 10.1 | 12.4 | 11.9 |
| 108 | 235139_PM_at | GNGT2 | guanine nucleotide binding protein (G protein), gamma transducing activity polypeptide | 0.000604705 | 35.8 | 50.6 | 51.5 |
| 109 | 235545_PM_at | DEPDC1 | DEP domain containing 1 | 0.00060962 | 8.7 | 8.4 | 10.0 |
| 110 | 242096_PM_at | — | — | 0.000618307 | 8.6 | 8.7 | 10.3 |
| 111 | 1553042_PM_a_at | NFKBID | nuclear factor of kappa light polypeptide gene enhancer in B-cells inhibitor, delta | 0.000619863 | 14.9 | 17.7 | 16.0 |
| 112 | 209368_PM_at | EPHX2 | epoxide hydrolase 2, cytoplasmic | 0.000625958 | 33.6 | 25.2 | 22.3 |
| 113 | 1553681_PM_a_at | PRF1 | perforin 1 (pore forming protein) | 0.000629562 | 181.7 | 312.5 | 312.3 |
| 114 | 223836_PM_at | FGFBP2 | fibroblast growth factor binding protein 2 | 0.000647084 | 432.4 | 739.7 | 788.9 |
| 115 | 210812_PM_at | XRCC4 | X-ray repair complementing defective repair in Chinese hamster cells 4 | 0.000674811 | 13.2 | 15.5 | 16.5 |
| 116 | 230846_PM_at | AKAP5 | A kinase (PRKA) anchor protein 5 | 0.000678814 | 10.9 | 9.3 | 11.2 |
| 117 | 214567_PM_s_at | XCL1 /// XCL2 | chemokine (C motif) ligand 1 /// chemokine (C motif) ligand 2 | 0.000680647 | 211.0 | 338.8 | 347.2 |
| 118 | 237221_PM_at | — | — | 0.00069712 | 9.9 | 8.7 | 9.5 |
| 119 | 232793_PM_at | — | — | 0.000698404 | 10.2 | 12.5 | 13.0 |
| 120 | 239479_PM_x_at | — | — | 0.000700142 | 28.1 | 18.0 | 20.6 |
| 121 | 1558836_PM_at | — | — | 0.000706412 | 33.2 | 53.1 | 45.7 |
| 122 | 1562698_PM_x_at | LOC339988 | hypothetical LOC339988 | 0.000710123 | 108.5 | 165.5 | 158.7 |
| 123 | 1552646_PM_at | IL11RA | interleukin 11 receptor, alpha | 0.000716149 | 15.9 | 19.4 | 16.3 |
| 124 | 236220_PM_at | — | — | 0.000735209 | 9.9 | 8.3 | 7.7 |
| 125 | 211379_PM_x_at | B3GALNT1 | beta-1,3-N-acetylgalactosaminyltransferase 1 (globoside blood group) | 0.00074606 | 8.9 | 8.2 | 9.7 |

TABLE 5-continued 147 probesets for distinguishing between AR, HCV and HCV + AR in Liver PAXgene samples

| # | Probeset ID | Gene Symbol | Gene Title | p-value (Phenotype) | AR - Mean | HCV - Mean | HCV + AR - Mean |
|---|---|---|---|---|---|---|---|
| 126 | 222830_PM_at | GRHL1 | grainyhead-like 1 (Drosophila) | 0.000766774 | 14.7 | 10.5 | 10.4 |
| 127 | 210948_PM_s_at | LEF1 | lymphoid enhancer-binding factor 1 | 0.000768363 | 54.2 | 36.2 | 33.1 |
| 128 | 244798_PM_at | LOC100507492 | hypothetical LOC100507492 | 0.000800826 | 48.3 | 32.0 | 26.6 |
| 129 | 226666_PM_at | DAAM1 | dishevelled associated activator of morphogenesis 1 | 0.000828238 | 64.3 | 50.3 | 47.8 |
| 130 | 229378_PM_x_at | STOX1 | storkhead box 1 | 0.000836722 | 10.2 | 8.5 | 9.6 |
| 131 | 206366_PM_x_at | XCL1 | chemokine (C motif) ligand 1 | 0.000839844 | 194.1 | 306.8 | 324.9 |
| 132 | 214115_PM_at | VAMP5 | Vesicle-associated membrane protein 5 (myobrevin) | 0.000866755 | 13.2 | 12.1 | 16.6 |
| 133 | 201212_PM_at | LGMN | legumain | 0.00087505 | 18.9 | 15.9 | 13.1 |
| 134 | 204863_PM_s_at | IL6ST | interleukin 6 signal transducer (gp130, oncostatin M receptor) | 0.000897042 | 147.6 | 107.1 | 111.1 |
| 135 | 232229_PM_at | SETX | senataxin | 0.000906105 | 34.5 | 45.3 | 36.9 |
| 136 | 1555407_PM_s_at | FGD3 | FYVE, RhoGEF and PH domain containing 3 | 0.00091116 | 88.7 | 103.2 | 67.0 |
| 137 | 223127_PM_s_at | C1orf21 | chromosome 1 open reading frame 21 | 0.000923068 | 9.1 | 10.3 | 11.0 |
| 138 | 202458_PM_at | PRSS23 | protease, serine, 23 | 0.000924141 | 38.8 | 74.1 | 79.3 |
| 139 | 210606_PM_x_at | KLRD1 | killer cell lectin-like receptor subfamily D, member 1 | 0.000931313 | 289.8 | 421.9 | 473.0 |
| 140 | 212444_PM_at | — | — | 0.000935909 | 10.2 | 11.6 | 10.2 |
| 141 | 240893_PM_at | — | — | 0.000940973 | 8.6 | 9.7 | 10.3 |
| 142 | 219474_PM_at | C3orf52 | chromosome 3 open reading frame 52 | 0.000948853 | 8.9 | 10.0 | 10.2 |
| 143 | 235087_PM_at | UNKL | unkempt homolog (Drosophila)-like | 0.000967141 | 10.3 | 9.8 | 8.3 |
| 144 | 216907_PM_x_at | KIR3DL1 /// KIR3DL2 /// LOC727787 | killer cell immunoglobulin-like receptor, three domains, long cytoplasmic tail, 1 /// k | 0.000987803 | 12.6 | 16.1 | 19.1 |
| 145 | 238402_PM_at | FLJ35220 | hypothetical protein FLJ35220 | 0.000990348 | 17.2 | 19.9 | 15.3 |
| 146 | 239273_PM_s_at | MMP28 | matrix metallopeptidase 28 | 0.000993809 | 11.7 | 9.0 | 8.7 |
| 147 | 215894_PM_at | PTGDR | prostaglandin D2 receptor (DP) | 0.000994157 | 191.2 | 329.4 | 283.2 |

TABLE 6

320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 1 | 219863_PM_at | HERC5 | hect domain and RLD 5 | 1.53E-14 | 250.4 | 1254.7 | 1620.1 |
| 2 | 205660_PM_at | OASL | 2'-5'-oligoadenylate synthetase-like | 3.30E-14 | 128.1 | 1273.7 | 1760.9 |
| 3 | 210797_PM_s_at | OASL | 2'-5'-oligoadenylate synthetase-like | 4.03E-14 | 62.0 | 719.3 | 915.2 |
| 4 | 214453_PM_s_at | IFI44 | interferon-induced protein 44 | 3.98E-13 | 342.2 | 1646.7 | 1979.2 |
| 5 | 218986_PM_s_at | DDX60 | DEAD (Asp-Glu-Ala-Asp) box polypeptide 60 | 5.09E-12 | 352.2 | 1253.2 | 1403.0 |
| 6 | 202869_PM_at | OAS1 | 2',5'-oligoadenylate synthetase 1, 40/46 kDa | 4.47E-11 | 508.0 | 1648.7 | 1582.5 |
| 7 | 226702_PM_at | CMPK2 | cytidine monophosphate (UMP-CMP) kinase 2, mitochondrial | 5.23E-11 | 257.3 | 1119.1 | 1522.6 |
| 8 | 203153_PM_at | IFIT1 | interferon-induced protein with tetratricopeptide repeats 1 | 5.31E-11 | 704.0 | 2803.7 | 3292.9 |
| 9 | 202086_PM_at | MX1 | myxovirus (influenza virus) resistance 1, interferon-inducible protein p78 (mouse) | 5.53E-11 | 272.4 | 1420.9 | 1836.8 |
| 10 | 242625_PM_at | RSAD2 | radical S-adenosyl methionine domain containing 2 | 9.62E-11 | 56.2 | 389.2 | 478.2 |
| 11 | 213797_PM_at | RSAD2 | radical S-adenosyl methionine domain containing 2 | 1.43E-10 | 91.4 | 619.3 | 744.7 |
| 12 | 204972_PM_at | OAS2 | 2'-5'-oligoadenylate synthetase 2, 69/71 kDa | 2.07E-10 | 88.7 | 402.1 | 536.1 |
| 13 | 219352_PM_at | HERC6 | hect domain and RLD 6 | 2.52E-10 | 49.5 | 206.7 | 272.8 |
| 14 | 205483_PM_s_at | ISG15 | ISG15 ubiquitin-like modifier | 3.68E-10 | 629.9 | 3181.1 | 4608.0 |
| 15 | 205552_PM_s_at | OAS1 | 2',5'-oligoadenylate synthetase 1, 40/46 kDa | 4.08E-10 | 224.7 | 868.7 | 921.2 |
| 16 | 204415_PM_at | IFI6 | interferon, alpha-inducible protein 6 | 5.83E-10 | 787.8 | 4291.7 | 5465.6 |
| 17 | 205569_PM_at | LAMP3 | lysosomal-associated membrane protein 3 | 6.80E-10 | 21.8 | 91.3 | 126.2 |
| 18 | 219209_PM_at | IFIH1 | interferon induced with helicase C domain 1 | 8.15E-10 | 562.3 | 1246.9 | 1352.7 |
| 19 | 218400_PM_at | OAS3 | 2'-5'-oligoadenylate synthetase 3, 100 kDa | 2.85E-09 | 87.9 | 265.2 | 364.5 |
| 20 | 229450_PM_at | IFIT3 | interferon-induced protein with tetratricopeptide repeats 3 | 4.69E-09 | 1236.3 | 2855.3 | 3291.7 |
| 21 | 226757_PM_at | IFIT2 | interferon-induced protein with tetratricopeptide repeats 2 | 5.35E-09 | 442.3 | 1083.2 | 1461.9 |
| 22 | 204439_PM_at | IFI44L | interferon-induced protein 44-like | 5.77E-09 | 146.3 | 794.4 | 1053.5 |
| 23 | 227609_PM_at | EPSTI1 | epithelial stromal interaction 1 (breast) | 1.03E-08 | 396.9 | 1079.8 | 1370.3 |
| 24 | 204747_PM_at | IFIT3 | interferon-induced protein with tetratricopeptide repeats 3 | 1.59E-08 | 228.3 | 698.1 | 892.7 |
| 25 | 217502_PM_at | IFIT2 | interferon-induced protein with tetratricopeptide repeats 2 | 1.85E-08 | 222.9 | 575.1 | 745.9 |
| 26 | 228607_PM_at | OAS2 | 2'-5'-oligoadenylate synthetase 2, 69/71 kDa | 2.16E-08 | 60.9 | 182.0 | 225.6 |
| 27 | 224870_PM_at | KIAA0114 | KIAA0114 | 2.48E-08 | 156.5 | 81.8 | 66.0 |
| 28 | 202411_PM_at | IFI27 | interferon, alpha-inducible protein 27 | 4.25E-08 | 1259.4 | 5620.8 | 5634.1 |
| 29 | 223220_PM_s_at | PARP9 | poly (ADP-ribose) polymerase family, member 9 | 4.48E-08 | 561.7 | 1084.4 | 1143.1 |
| 30 | 208436_PM_s_at | IRF7 | interferon regulatory factor 7 | 4.57E-08 | 58.9 | 102.9 | 126.9 |
| 31 | 219211_PM_at | USP18 | ubiquitin specific peptidase 18 | 6.39E-08 | 51.0 | 183.6 | 196.1 |
| 32 | 206133_PM_at | XAF1 | XIAP associated factor 1 | 7.00E-08 | 463.9 | 1129.2 | 1327.1 |
| 33 | 202446_PM_s_at | PLSCR1 | phospholipid scramblase 1 | 1.12E-07 | 737.8 | 1317.7 | 1419.8 |
| 34 | 235276_PM_at | EPSTI1 | epithelial stromal interaction 1 (breast) | 1.58E-07 | 93.5 | 244.2 | 279.9 |
| 35 | 219684_PM_at | RTP4 | receptor (chemosensory) transporter protein 4 | 1.64E-07 | 189.5 | 416.3 | 541.7 |
| 36 | 222986_PM_s_at | SHISA5 | shisa homolog 5 (Xenopus laevis) | 1.68E-07 | 415.0 | 586.9 | 681.4 |
| 37 | 223298_PM_s_at | NT5C3 | 5'-nucleotidase, cytosolic III | 2.06E-07 | 247.6 | 443.4 | 474.7 |
| 38 | 228275_PM_at | — | — | 2.24E-07 | 71.6 | 159.3 | 138.9 |
| 39 | 228617_PM_at | XAF1 | XIAP associated factor 1 | 2.28E-07 | 678.3 | 1412.3 | 1728.5 |
| 40 | 214022_PM_s_at | IFITM1 | interferon induced transmembrane protein 1 (9-27) | 2.37E-07 | 1455.1 | 2809.3 | 3537.2 |

TABLE 6-continued 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 41 | 214059_PM_at | IFI44 | Interferon-induced protein 44 | 2.61E-07 | 37.1 | 158.8 | 182.5 |
| 42 | 206553_PM_at | OAS2 | 2'-5'-oligoadenylate synthetase 2, 69/71 kDa | 2.92E-07 | 18.9 | 45.6 | 53.1 |
| 43 | 214290_PM_s_at | HIST2H2AA3 /// HIST2H2AA4 | histone cluster 2, H2aa3 /// histone cluster 2, H2aa4 | 3.50E-07 | 563.4 | 1151.2 | 1224.7 |
| 44 | 1554079_PM_at | GALNTL4 | UDP-N-acetyl-alpha-D-galactosamine: polypeptide N-acetylgalactosaminyltransferase-like 4 | 3.58E-07 | 69.9 | 142.6 | 109.0 |
| 45 | 202430_PM_s_at | PLSCR1 | phospholipid scramblase 1 | 3.85E-07 | 665.7 | 1162.8 | 1214.5 |
| 46 | 218280_PM_x_at | HIST2H2AA3 /// HIST2H2AA4 | histone cluster 2, H2aa3 /// histone cluster 2, H2aa4 | 5.32E-07 | 299.7 | 635.3 | 721.7 |
| 47 | 202708_PM_s_at | HIST2H2BE | histone cluster 2, H2be | 7.04E-07 | 62.4 | 112.2 | 115.4 |
| 48 | 222134_PM_at | DDO | D-aspartate oxidase | 7.37E-07 | 76.0 | 134.9 | 118.4 |
| 49 | 215071_PM_s_at | HIST1H2AC | histone cluster 1, H2ac | 9.11E-07 | 502.4 | 1009.1 | 1019.0 |
| 50 | 209417_PM_s_at | IFI35 | interferon-induced protein 35 | 9.12E-07 | 145.5 | 258.9 | 323.5 |
| 51 | 218543_PM_s_at | PARP12 | poly (ADP-ribose) polymerase family, member 12 | 9.29E-07 | 172.3 | 280.3 | 366.3 |
| 52 | 202864_PM_s_at | SP100 | SP100 nuclear antigen | 1.09E-06 | 372.5 | 604.2 | 651.9 |
| 53 | 217719_PM_at | EIF3L | eukaryotic translation initiation factor 3, subunit L | 1.15E-06 | 4864.0 | 3779.0 | 3600.0 |
| 54 | 230314_PM_at | — | — | 1.29E-06 | 36.0 | 62.5 | 59.5 |
| 55 | 202863_PM_at | SP100 | SP100 nuclear antigen | 1.37E-06 | 500.0 | 751.3 | 815.8 |
| 56 | 236798_PM_at | — | — | 1.38E-06 | 143.1 | 307.0 | 276.8 |
| 57 | 233555_PM_s_at | SULF2 | sulfatase 2 | 1.38E-06 | 47.0 | 133.4 | 119.0 |
| 58 | 236717_PM_at | FAM179A | family with sequence similarity 179, member A | 1.44E-06 | 16.5 | 16.1 | 24.2 |
| 59 | 228531_PM_at | SAMD9 | sterile alpha motif domain containing 9 | 1.54E-06 | 143.0 | 280.3 | 351.7 |
| 60 | 209911_PM_x_at | HIST1H2BD | histone cluster 1, H2bd | 1.69E-06 | 543.7 | 999.9 | 1020.7 |
| 61 | 238039_PM_at | LOC728769 | hypothetical LOC728769 | 1.77E-06 | 62.8 | 95.5 | 97.2 |
| 62 | 222067_PM_x_at | HIST1H2BD | histone cluster 1, H2bd | 1.78E-06 | 378.1 | 651.6 | 661.4 |
| 63 | 201601_PM_x_at | IFITM1 | interferon induced transmembrane protein 1 (9-27) | 2.00E-06 | 1852.8 | 2956.0 | 3664.5 |
| 64 | 213361_PM_at | TDRD7 | tudor domain containing 7 | 2.09E-06 | 158.5 | 314.1 | 328.6 |
| 65 | 224998_PM_at | CMTM4 | CKLF-like MARVEL transmembrane domain containing 4 | 2.15E-06 | 42.6 | 30.0 | 22.3 |
| 66 | 222793_PM_at | DDX58 | DEAD (Asp-Glu-Ala-Asp) box polypeptide 58 | 2.41E-06 | 93.9 | 231.9 | 223.1 |
| 67 | 225076_PM_s_at | ZNFX1 | zinc finger, NFX1-type containing 1 | 2.55E-06 | 185.0 | 286.0 | 359.1 |
| 68 | 236381_PM_s_at | WDR8 | WD repeat domain 8 | 2.68E-06 | 41.6 | 61.5 | 64.8 |
| 69 | 203265_PM_at | UNC119B | unc-119 homolog B (C. elegans) | 2.72E-06 | 383.4 | 272.7 | 241.0 |
| 70 | 215690_PM_x_at | GPAA1 | glycosylphosphatidylinositol anchor attachment protein 1 homolog (yeast) | 2.75E-06 | 141.0 | 103.7 | 107.5 |
| 71 | 211799_PM_x_at | HLA-C | major histocompatibility complex, class I, C | 2.77E-06 | 912.3 | 1446.0 | 1649.4 |
| 72 | 218543_PM_x_at | DDX58 | DEAD (Asp-Glu-Ala-Asp) box polypeptide 58 | 2.87E-06 | 153.9 | 310.7 | 350.7 |
| 73 | 235686_PM_at | C2orf60 | chromosome 2 open reading frame 60 | 3.32E-06 | 17.2 | 23.2 | 20.1 |
| 74 | 236193_PM_at | LOC100506979 | hypothetical LOC100506979 | 3.96E-06 | 24.5 | 48.1 | 51.2 |
| 75 | 221767_PM_x_at | HDLBP | high density lipoprotein binding protein | 4.00E-06 | 1690.9 | 1301.2 | 1248.4 |
| 76 | 225796_PM_at | PXK | PX domain containing serine/threonine kinase | 4.08E-06 | 99.2 | 168.1 | 154.9 |
| 77 | 209762_PM_x_at | SP110 | SP110 nuclear body protein | 4.68E-06 | 150.5 | 242.3 | 282.0 |
| 78 | 211060_PM_x_at | GPAA1 | glycosylphosphatidylinositol anchor attachment protein 1 homolog (yeast) | 4.74E-06 | 153.1 | 113.3 | 116.8 |
| 79 | 218019_PM_s_at | PDXK | pyridoxal (pyridoxine, vitamin B6) kinase | 4.95E-06 | 304.5 | 210.8 | 198.6 |
| 80 | 219364_PM_at | DHX58 | DEXH (Asp-Glu-X-His) box polypeptide 58 | 5.46E-06 | 71.5 | 111.2 | 113.0 |

TABLE 6-continued 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 81 | 203281_PM_s_at | UBA7 | ubiquitin-like modifier activating enzyme 7 | 6.79E-06 | 80.2 | 108.2 | 131.0 |
| 82 | 200923_PM_at | LGALS3BP | lectin, galactoside-binding, soluble, 3 binding protein | 6.99E-06 | 193.1 | 401.5 | 427.4 |
| 83 | 208527_PM_x_at | HIST1H2BE | histone cluster 1, H2be | 7.54E-06 | 307.7 | 529.7 | 495.4 |
| 84 | 219479_PM_at | KDELC1 | KDEL (Lys-Asp-Glu-Leu) containing 1 | 7.81E-06 | 74.1 | 131.5 | 110.6 |
| 85 | 200950_PM_at | ARPC1A | actin related protein 2/3 complex, subunit 1A, 41 kDa | 1.00E-05 | 1015.8 | 862.8 | 782.0 |
| 86 | 213294_PM_at | EIF2AK2 | eukaryotic translation initiation factor 2-alpha kinase 2 | 1.02E-05 | 390.4 | 690.7 | 651.6 |
| 87 | 205943_PM_at | TDO2 | tryptophan 2,3-dioxygenase | 1.06E-05 | 7808.6 | 10534.7 | 10492.0 |
| 88 | 217969_PM_at | C11orf2 | chromosome 11 open reading frame 2 | 1.21E-05 | 302.6 | 235.0 | 214.8 |
| 89 | 1552370_PM_at | C4orf33 | chromosome 4 open reading frame 33 | 1.24E-05 | 58.4 | 124.5 | 97.2 |
| 90 | 211911_PM_x_at | HLA-B | major histocompatibility complex, class I, B | 1.34E-05 | 4602.1 | 6756.7 | 7737.3 |
| 91 | 232563_PM_at | ZNF684 | zinc finger protein 684 | 1.36E-05 | 131.9 | 236.2 | 231.8 |
| 92 | 203882_PM_at | IRF9 | interferon regulatory factor 9 | 1.43E-05 | 564.0 | 780.1 | 892.0 |
| 93 | 225991_PM_at | TMEM41A | transmembrane protein 41A | 1.45E-05 | 122.5 | 202.1 | 179.6 |
| 94 | 239988_PM_at | — | — | 1.53E-05 | 11.5 | 15.4 | 16.1 |
| 95 | 244434_PM_at | GPR82 | G protein-coupled receptor 82 | 1.55E-05 | 18.5 | 32.5 | 37.0 |
| 96 | 201489_PM_at | PPIF | peptidylprolyl isomerase F | 1.58E-05 | 541.7 | 899.5 | 672.9 |
| 97 | 221476_PM_s_at | RPL15 | ribosomal protein L15 | 1.58E-05 | 3438.3 | 2988.5 | 2742.8 |
| 98 | 244398_PM_x_at | ZNF684 | zinc finger protein 684 | 1.65E-05 | 57.2 | 96.9 | 108.5 |
| 99 | 208628_PM_s_at | YBX1 | Y box binding protein 1 | 1.66E-05 | 4555.5 | 3911.6 | 4365.0 |
| 100 | 211710_PM_x_at | RPL4 | ribosomal protein L4 | 1.73E-05 | 5893.1 | 4853.3 | 4955.4 |
| 101 | 229741_PM_at | MAVS | mitochondrial antiviral signaling protein | 1.78E-05 | 65.2 | 44.6 | 34.4 |
| 102 | 206386_PM_at | SERPINA7 | serpin peptidase inhibitor, clade A (alpha-1 antiproteinase, antitrypsin), member 7 | 1.90E-05 | 3080.8 | 4251.6 | 4377.2 |
| 103 | 213293_PM_s_at | TRIM22 | tripartite motif-containing 22 | 1.92E-05 | 1122.0 | 1829.2 | 2293.2 |
| 104 | 200089_PM_s_at | RPL4 | ribosomal protein L4 | 1.93E-05 | 3387.5 | 2736.6 | 2823.9 |
| 105 | 235037_PM_at | TMEM41A | transmembrane protein 41A | 1.96E-05 | 134.7 | 218.5 | 192.9 |
| 106 | 226459_PM_at | PIK3AP1 | phosphoinositide-3-kinase adaptor protein 1 | 2.10E-05 | 2152.4 | 2747.6 | 2929.7 |
| 107 | 200023_PM_s_at | EIF3F | eukaryotic translation initiation factor 3, subunit F | 2.16E-05 | 1764.9 | 1467.6 | 1365.3 |
| 108 | 205161_PM_s_at | PEX11A | peroxisomal biogenesis factor 11 alpha | 2.17E-05 | 51.9 | 87.3 | 76.9 |
| 109 | 225291_PM_at | PNPT1 | polyribonucleotide nucleotidyltransferase 1 | 2.18E-05 | 287.0 | 469.1 | 455.0 |
| 110 | 220445_PM_s_at | CSAG2 /// CSAG3 | CSAG family, member 2 /// CSAG family, member 3 | 2.24E-05 | 16.3 | 91.2 | 120.9 |
| 111 | 226229_PM_s_at | SSU72 | SSU72 RNA polymerase II CTD phosphatase homolog (S. cerevisiae) | 2.24E-05 | 50.4 | 36.7 | 32.3 |
| 112 | 207418_PM_s_at | DDO | D-aspartate oxidase | 2.48E-05 | 35.2 | 57.0 | 50.7 |
| 113 | 201786_PM_s_at | ADAR | adenosine deaminase, RNA-specific | 2.59E-05 | 1401.5 | 1867.9 | 1907.8 |
| 114 | 224724_PM_at | SULF2 | sulfatase 2 | 2.61E-05 | 303.6 | 540.1 | 553.9 |
| 115 | 201618_PM_x_at | GPAA1 | glycosylphosphatidylinositol anchor attachment protein 1 homolog (yeast) | 2.63E-05 | 131.2 | 98.1 | 97.5 |
| 116 | 201154_PM_x_at | RPL4 | ribosomal protein L4 | 2.78E-05 | 3580.5 | 2915.6 | 2996.2 |
| 117 | 200094_PM_s_at | EEF2 | eukaryotic translation elongation factor 2 | 3.08E-05 | 3991.6 | 3248.5 | 3061.1 |
| 118 | 208424_PM_s_at | CIAPIN1 | cytokine induced apoptosis inhibitor 1 | 3.17E-05 | 66.7 | 94.8 | 94.8 |
| 119 | 204102_PM_s_at | EEF2 | eukaryotic translation elongation factor 2 | 3.23E-05 | 3680.8 | 3102.7 | 2853.6 |
| 120 | 203595_PM_s_at | IFIT5 | interferon-induced protein with tetratricopeptide repeats 5 | 3.44E-05 | 266.9 | 445.8 | 450.9 |

TABLE 6-continued 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 121 | 228152_PM_s_at | DDX60L | DEAD (Asp-Glu-Ala-Asp) box polypeptide 60-like | 3.52E-05 | 136.1 | 280.8 | 304.5 |
| 122 | 201490_PM_s_at | PPIF | peptidylprolyl isomerase F | 3.64E-05 | 209.2 | 443.5 | 251.4 |
| 123 | 217933_PM_s_at | LAP3 | leucine aminopeptidase 3 | 3.81E-05 | 3145.6 | 3985.6 | 4629.9 |
| 124 | 203596_PM_s_at | IFIT5 | interferon-induced protein with tetratricopeptide repeats 5 | 3.93E-05 | 195.9 | 315.8 | 339.0 |
| 125 | 220104_PM_at | ZC3HAV1 | zinc finger CCCH-type, antiviral 1 | 4.25E-05 | 23.3 | 53.1 | 57.7 |
| 126 | 213080_PM_at | RPL5 | ribosomal protein L5 | 4.28E-05 | 6986.7 | 6018.3 | 5938.6 |
| 127 | 208729_PM_x_at | HLA-B | major histocompatibility complex, class I, B | 4.58E-05 | 4720.9 | 6572.7 | 7534.4 |
| 128 | 32541_PM_at | PPP3CC | protein phosphatase 3, catalytic subunit, gamma isozyme | 4.71E-05 | 63.3 | 79.7 | 81.3 |
| 129 | 216231_PM_x_at | B2M | beta-2-microglobulin | 4.79E-05 | 13087.7 | 14063.7 | 14511.1 |
| 130 | 206082_PM_at | HCP5 | HLA complex P5 | 4.91E-05 | 129.7 | 205.7 | 300.9 |
| 131 | 213275_PM_x_at | CTSB | cathepsin B | 4.93E-05 | 2626.4 | 2001.3 | 2331.0 |
| 132 | 200643_PM_at | HDLBP | high density lipoprotein binding protein | 5.04E-05 | 404.4 | 317.8 | 304.4 |
| 133 | 235309_PM_at | RPS15A | ribosomal protein S15a | 5.08E-05 | 98.5 | 77.4 | 55.3 |
| 134 | 209761_PM_s_at | SP110 | SP110 nuclear body protein | 5.33E-05 | 84.2 | 145.6 | 156.0 |
| 135 | 230753_PM_at | PATL2 | protein associated with topoisomerase II homolog 2 (yeast) | 5.55E-05 | 42.8 | 52.1 | 68.4 |
| 136 | 225369_PM_at | ESAM | endothelial cell adhesion molecule | 5.72E-05 | 14.9 | 13.1 | 11.9 |
| 137 | 219255_PM_x_at | IL17RB | interleukin 17 receptor B | 5.88E-05 | 334.9 | 607.9 | 568.7 |
| 138 | 208392_PM_x_at | SP110 | SP110 nuclear body protein | 6.05E-05 | 60.2 | 96.1 | 115.5 |
| 139 | 221044_PM_s_at | TRIM34 /// TRIM6-TRIM34 | tripartite motif-containing 34 /// TRIM6-TRIM34 readthrough | 6.07E-05 | 47.0 | 65.1 | 70.9 |
| 140 | 1554375_PM_a_at | NR1H4 | nuclear receptor subfamily 1, group H, member 4 | 6.23E-05 | 585.8 | 913.1 | 791.8 |
| 141 | 210218_PM_at | SP100 | SP100 nuclear antigen | 6.41E-05 | 129.0 | 207.4 | 222.0 |
| 142 | 206340_PM_at | NR1H4 | nuclear receptor subfamily 1, group H, member 4 | 6.67E-05 | 983.3 | 1344.6 | 1278.4 |
| 143 | 222868_PM_s_at | IL18BP | interleukin 18 binding protein | 7.04E-05 | 72.0 | 45.4 | 90.9 |
| 144 | 204211_PM_x_at | EIF2AK2 | eukaryotic translation initiation factor 2-alpha kinase 2 | 7.04E-05 | 144.8 | 215.9 | 229.8 |
| 145 | 231702_PM_at | TDO2 | Tryptophan 2,3-dioxygenase | 7.09E-05 | 57.9 | 101.7 | 83.6 |
| 146 | 204906_PM_at | RPS6KA2 | ribosomal protein S6 kinase, 90 kDa, polypeptide 2 | 7.10E-05 | 40.1 | 28.3 | 28.7 |
| 147 | 218192_PM_at | IP6K2 | inositol hexakisphosphate kinase 2 | 7.15E-05 | 84.0 | 112.5 | 112.7 |
| 148 | 211528_PM_x_at | HLA-G | major histocompatibility complex, class I, G | 7.45E-05 | 1608.7 | 2230.0 | 2613.2 |
| 149 | 208546_PM_x_at | HIST1H2BB /// HIST1H2BC /// HIST1H2BD /// HIST1H2BE /// HIST1H2BG /// HIST1H2BH /// HIST1H2BI | histone cluster 1, H2bb /// histone cluster 1, H2bc /// histone cluster 1, H2bd /// his | 7.82E-05 | 65.3 | 131.7 | 112.0 |
| 150 | 204483_PM_at | ENO3 | enolase 3 (beta, muscle) | 7.85E-05 | 547.8 | 1183.9 | 891.4 |
| 151 | 203148_PM_s_at | TRIM14 | tripartite motif-containing 14 | 7.97E-05 | 590.8 | 803.6 | 862.4 |
| 152 | 1557120_PM_at | EEF1A1 | Eukaryotic translation elongation factor 1 alpha 1 | 8.14E-05 | 20.5 | 17.4 | 17.4 |
| 153 | 203067_PM_at | PDHX | pyruvate dehydrogenase complex, component X | 8.21E-05 | 322.0 | 457.6 | 413.2 |
| 154 | 224156_PM_x_at | IL17RB | interleukin 17 receptor B | 8.48E-05 | 426.4 | 755.4 | 699.9 |
| 155 | 203073_PM_at | COG2 | component of oligomeric golgi complex 2 | 9.64E-05 | 73.6 | 100.2 | 96.2 |

TABLE 6-continued 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 156 | 211937_PM_at | EIF4B | eukaryotic translation initiation factor 4B | 9.68E-05 | 823.8 | 617.5 | 549.7 |
| 157 | 229804_PM_x_at | CBWD2 | COBW domain containing 2 | 9.69E-05 | 170.0 | 225.0 | 229.1 |
| 158 | 225009_PM_at | CMTM4 | CKLF-like MARVEL transmembrane domain containing 4 | 0.00010207 | 54.0 | 40.5 | 32.3 |
| 159 | 221305_PM_s_at | UGT1A8 /// UGT1A9 | UDP glucuronosyltransferase 1 family, polypeptide A8 /// UDP glucuronosyltransferase 1 | 0.000109701 | 214.8 | 526.8 | 346.9 |
| 160 | 1557820_PM_at | AFG3L2 | AFG3 ATPase family gene 3-like 2 (S. cerevisiae) | 0.000112458 | 1037.9 | 1315.0 | 1232.5 |
| 161 | 237627_PM_at | LOC100506318 | hypothetical LOC100506318 | 0.000115046 | 29.2 | 22.6 | 19.1 |
| 162 | 205819_PM_at | MARCO | macrophage receptor with collagenous structure | 0.000115755 | 625.3 | 467.4 | 904.8 |
| 163 | 215313_PM_x_at | HLA-A /// LOC100507703 | major histocompatibility complex, class I, A /// HLA class I histocompatibility antigen | 0.000116881 | 6193.5 | 8266.5 | 9636.7 |
| 164 | 226950_PM_at | ACVR1L1 | activin A receptor type II-like 1 | 0.000118584 | 28.2 | 25.1 | 35.5 |
| 165 | 213716_PM_s_at | SECTM1 | secreted and transmembrane 1 | 0.000118874 | 44.7 | 32.0 | 50.6 |
| 166 | 207468_PM_s_at | SFRP5 | secreted frizzled-related protein 5 | 0.000121583 | 19.6 | 25.5 | 20.2 |
| 167 | 218674_PM_at | C5orf44 | chromosome 5 open reading frame 44 | 0.000124195 | 60.4 | 97.9 | 77.7 |
| 168 | 219691_PM_at | SAMD9 | sterile alpha motif domain containing 9 | 0.000126093 | 29.6 | 49.5 | 53.9 |
| 169 | 230795_PM_at | | | 0.00012691 | 115.4 | 188.1 | 164.2 |
| 170 | 200941_PM_at | HSBP1 | heat shock factor binding protein 1 | 0.000127149 | 559.2 | 643.2 | 623.6 |
| 171 | 230174_PM_at | LYPLAL1 | lysophospholipase-like 1 | 0.000127616 | 476.3 | 597.5 | 471.3 |
| 172 | 214459_PM_x_at | HLA-C | major histocompatibility complex, class I, C | 0.000131095 | 4931.4 | 6208.3 | 6855.4 |
| 173 | 228971_PM_at | LOC100505759 | hypothetical LOC100505759 | 0.000131603 | 210.7 | 139.7 | 91.6 |
| 174 | 217073_PM_x_at | APOA1 | apolipoprotein A-I | 0.000135801 | 12423.2 | 13707.0 | 13369.3 |
| 175 | 203964_PM_at | NMI | N-myc (and STAT) interactor | 0.000138824 | 641.8 | 820.4 | 930.9 |
| 176 | 1556988_PM_s_at | CHD1L | chromodomain helicase DNA binding protein 1-like | 0.000142541 | 164.4 | 241.1 | 226.9 |
| 177 | 214890_PM_s_at | FAM149A | family with sequence similarity 149, member A | 0.000144828 | 534.0 | 444.9 | 342.4 |
| 178 | 209115_PM_at | UBA3 | ubiquitin-like modifier activating enzyme 1 | 0.000144924 | 456.2 | 532.0 | 555.8 |
| 179 | 212284_PM_x_at | TPT1 | tumor protein, translationally-controlled 1 | 0.000146465 | 15764.0 | 14965.0 | 14750.6 |
| 180 | 1552274_PM_at | PXK | PX domain containing serine/threonine kinase | 0.000150376 | 24.9 | 37.1 | 43.1 |
| 181 | 214889_PM_at | FAM149A | family with sequence similarity 149, member A | 0.00015075 | 295.1 | 236.6 | 152.6 |
| 182 | 213287_PM_s_at | KRT10 | keratin 10 | 0.000151197 | 644.2 | 551.6 | 509.4 |
| 183 | 213051_PM_at | ZC3HAV1 | zinc finger CCCH-type, antiviral 1 | 0.000152213 | 635.3 | 963.0 | 917.5 |
| 184 | 219731_PM_at | CC2D2B | Coiled-coil and C2 domain containing 2B | 0.000152224 | 37.5 | 50.5 | 50.5 |
| 185 | 206211_PM_at | SELE | selectin E | 0.000156449 | 76.0 | 35.1 | 22.8 |
| 186 | 217436_PM_x_at | HLA-A /// HLA-F /// HLA-J | major histocompatibility complex, class I, A /// major histocompatibility complex, clas | 0.000159936 | 972.4 | 1408.3 | 1820.7 |
| 187 | 203970_PM_s_at | PEX3 | peroxisomal biogenesis factor 3 | 0.000164079 | 387.4 | 540.4 | 434.7 |
| 188 | 1556643_PM_at | FAM125A | Family with sequence similarity 125, member A | 0.000170998 | 68.0 | 107.1 | 95.8 |
| 189 | 211529_PM_x_at | HLA-G | major histocompatibility complex, class I, G | 0.000174559 | 2166.9 | 3107.2 | 3708.7 |
| 190 | 223187_PM_s_at | ORMDL1 | ORM1-like 1 (S. cerevisiae) | 0.000182187 | 784.3 | 918.4 | 945.5 |
| 191 | 1566249_PM_at | | | 0.000182326 | 15.1 | 12.7 | 12.3 |
| 192 | 218111_PM_s_at | CMAS | cytidine monophosphate N-acetylneuraminic acid synthetase | 0.000182338 | 242.6 | 418.6 | 310.9 |
| 193 | 224361_PM_s_at | IL17RB | interleukin 17 receptor B | 0.000183121 | 231.0 | 460.8 | 431.4 |
| 194 | 217807_PM_s_at | GLTSCR2 | glioma tumor suppressor candidate region gene 2 | 0.000185926 | 3262.6 | 2650.0 | 2523.4 |
| 195 | 222571_PM_at | ST6GALNAC6 | ST6 (alpha-N-acetyl-neuraminyl-2,3-beta-galactosyl-1,3)-N-acetylgalactosaminide alpha-2 | 0.00018814 | 31.7 | 24.2 | 25.0 |

TABLE 6-continued 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 196 | 208012_PM_x_at | SP110 | SP110 nuclear body protein | 0.000189717 | 245.7 | 344.1 | 397.9 |
| 197 | 208579_PM_x_at | H2BFS | H2B histone family, member S | 0.000192843 | 352.8 | 581.2 | 525.7 |
| 198 | 204309_PM_at | CYP11A1 | cytochrome P450, family 11, subfamily A, polypeptide 1 | 0.000193276 | 17.5 | 27.3 | 29.2 |
| 199 | 211956_PM_s_at | EIF1 | eukaryotic translation initiation factor 1 | 0.000193297 | 6954.0 | 6412.9 | 6189.5 |
| 200 | 214455_PM_at | HIST1H2BC | histone cluster 1, H2bc | 0.000196036 | 49.9 | 104.4 | 101.5 |
| 201 | 232140_PM_at | — | — | 0.00019705 | 25.3 | 32.7 | 30.9 |
| 202 | 214054_PM_at | DOK2 | docking protein 2, 56 kDa | 0.000197843 | 28.6 | 25.1 | 39.9 |
| 203 | 210606_PM_x_at | KLRD1 | killer cell lectin-like receptor subfamily D, member 1 | 0.000201652 | 59.7 | 46.6 | 94.1 |
| 204 | 211943_PM_x_at | TPT1 | tumor protein, translationally-controlled 1 | 0.000202842 | 12849.6 | 11913.9 | 11804.6 |
| 205 | 205506_PM_at | VIL1 | villin 1 | 0.000209043 | 67.1 | 28.6 | 21.7 |
| 206 | 210514_PM_x_at | HLA-G | major histocompatibility complex, class I, G | 0.000214822 | 715.2 | 976.4 | 1100.2 |
| 207 | 235885_PM_at | P2RY12 | purinergic receptor P2Y, G-protein coupled, 12 | 0.000216727 | 21.1 | 30.2 | 49.1 |
| 208 | 212997_PM_s_at | TLK2 | tousled-like kinase 2 | 0.000217726 | 86.1 | 108.5 | 119.7 |
| 209 | 211976_PM_at | — | — | 0.000218277 | 145.9 | 115.9 | 104.8 |
| 210 | 231718_PM_at | SLU7 | SLU7 splicing factor homolog (S. cerevisiae) | 0.000221207 | 185.0 | 205.3 | 234.8 |
| 211 | 225634_PM_at | ZC3HAV1 | zinc finger CCCH-type, antiviral 1 | 0.000224661 | 388.3 | 511.6 | 490.5 |
| 212 | 205936_PM_s_at | HK3 | hexokinase 3 (white cell) | 0.000231343 | 22.5 | 19.2 | 30.2 |
| 213 | 203912_PM_s_at | DNASE1L1 | deoxyribonuclease I-like 1 | 0.000231815 | 171.2 | 151.3 | 183.8 |
| 214 | 224603_PM_at | — | — | 0.000232518 | 562.4 | 449.5 | 405.8 |
| 215 | 218085_PM_at | CHMP5 | chromatin modifying protein 5 | 0.000232702 | 484.6 | 584.5 | 634.2 |
| 216 | 204821_PM_at | BTN3A3 | butyrophilin, subfamily 3, member A3 | 0.000235674 | 245.0 | 335.6 | 401.3 |
| 217 | 217819_PM_at | GOLGA7 | golgin A7 | 0.000242192 | 845.3 | 1004.2 | 967.8 |
| 218 | 200629_PM_at | WARS | tryptophanyl-tRNA synthetase | 0.000244656 | 423.1 | 279.6 | 508.5 |
| 219 | 206342_PM_x_at | IDS | iduronate 2-sulfatase | 0.000246177 | 122.3 | 88.8 | 95.0 |
| 220 | 1556023_PM_x_at | — | — | 0.000247892 | 14.4 | 12.5 | 12.6 |
| 221 | 213706_PM_at | GPD1 | glycerol-3-phosphate dehydrogenase 1 (soluble) | 0.000254153 | 124.3 | 227.8 | 162.9 |
| 222 | 204312_PM_x_at | CREB1 | cAMP responsive element binding protein 1 | 0.000257352 | 28.9 | 41.8 | 34.8 |
| 223 | 230036_PM_at | SAMD9L | sterile alpha motif domain containing 9-like | 0.000265574 | 54.8 | 75.0 | 115.7 |
| 224 | 222730_PM_s_at | ZDHHC2 | zinc finger, DHHC-type containing 2 | 0.000270517 | 96.7 | 66.7 | 58.1 |
| 225 | 224225_PM_s_at | ETV7 | ets variant 7 | 0.000274744 | 32.8 | 55.4 | 71.0 |
| 226 | 1294_PM_at | UBA7 | ubiquitin-like modifier activating enzyme 7 | 0.000290256 | 94.7 | 122.9 | 138.8 |
| 227 | 211075_PM_s_at | CD47 | CD47 molecule | 0.000296663 | 767.0 | 998.4 | 1061.6 |
| 228 | 228091_PM_at | STX17 | syntaxin 17 | 0.000298819 | 94.3 | 134.9 | 110.7 |
| 229 | 205821_PM_at | KLRK1 | killer cell lectin-like receptor subfamily K, member 1 | 0.000299152 | 95.2 | 73.8 | 156.4 |
| 230 | 1563075_PM_s_at | — | — | 0.000300425 | 41.4 | 63.6 | 82.2 |
| 231 | 224701_PM_at | PARP14 | poly (ADP-ribose) polymerase family, member 14 | 0.000301162 | 367.5 | 538.6 | 589.3 |
| 232 | 209300_PM_s_at | NECAP1 | NECAP endocytosis associated 1 | 0.000304084 | 184.5 | 246.0 | 246.0 |
| 233 | 200937_PM_s_at | RPL5 | ribosomal protein L5 | 0.00030872 | 3893.3 | 3346.0 | 3136.1 |
| 234 | 208523_PM_x_at | HIST1H2BI | histone cluster 1, H2bi | 0.000310294 | 79.8 | 114.5 | 115.8 |
| 235 | 210657_PM_s_at | 4-Sep | septin 4 | 0.000314978 | 122.1 | 78.4 | 61.6 |

TABLE 6-continued 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 236 | 239979_PM_at | — | selenophosphate synthetase 1 | 0.000315949 | 40.3 | 78.8 | 114.4 |
| 237 | 208941_PM_s_at | SEPHS1 | ubiquitin-conjugating enzyme E2L 6 | 0.000316337 | 291.7 | 228.3 | 213.0 |
| 238 | 201649_PM_at | UBE2L6 | eukaryotic translation elongation factor 1 gamma | 0.000320318 | 928.3 | 1228.3 | 1623.0 |
| 239 | 211927_PM_x_at | EEF1G | hypothetical LOC25845 | 0.000325197 | 5122.7 | 4241.7 | 4215.5 |
| 240 | 225458_PM_at | LOC25845 | histone cluster 1, H2bf | 0.000337719 | 93.6 | 131.5 | 110.8 |
| 241 | 208490_PM_x_at | HIST1H2BF | ATP synthase, H+ transporting, mitochondrial F1 complex, beta polypeptide | 0.000339692 | 61.0 | 96.3 | 97.7 |
| 242 | 201322_PM_at | ATP5B | major histocompatibility complex, class I, F | 0.000342076 | 2068.5 | 2566.2 | 2543.7 |
| 243 | 221978_PM_at | HLA-F | poly(rC) binding protein 2 | 0.00034635 | 49.8 | 69.5 | 100.6 |
| 244 | 204031_PM_s_at | PCBP2 | Protein inhibitor of activated STAT, 2 | 0.000351625 | 2377.6 | 2049.5 | 1911.5 |
| 245 | 243624_PM_at | PIAS2 | major histocompatibility complex, class II, DQ beta 1 /// HLA class II histocompatibili | 0.000352892 | 17.7 | 15.4 | 14.1 |
| 246 | 212998_PM_x_at | HLA-DQB1 /// LOC100133583 | | 0.000359233 | 570.2 | 339.6 | 742.5 |
| 247 | 204875_PM_s_at | GMDS | GDP-mannose 4,6-dehydratase | 0.00035965 | 73.9 | 41.2 | 45.5 |
| 248 | 225721_PM_at | SYNPO2 | synaptopodin 2 | 0.000362084 | 69.1 | 43.3 | 32.1 |
| 249 | 229696_PM_at | FECH | ferrochelatase | 0.000362327 | 42.6 | 34.1 | 28.8 |
| 250 | 208812_PM_x_at | HLA-C | major histocompatibility complex, class I, C | 0.000365707 | 7906.3 | 9602.6 | 10311.7 |
| 251 | 211666_PM_x_at | RPL3 | ribosomal protein L3 | 0.000376419 | 4594.1 | 4006.1 | 3490.3 |
| 252 | 219948_PM_x_at | UGT2A3 | UDP glucuronosyltransferase 2 family, polypeptide A3 | 0.000376972 | 219.5 | 454.5 | 350.3 |
| 253 | 204158_PM_s_at | TCIRG1 | T-cell, immune regulator 1, ATPase, H+ transporting, lysosomal V0 subunit A3 | 0.000384367 | 217.8 | 197.5 | 311.3 |
| 254 | 209846_PM_s_at | BTN3A2 | butyrophilin, subfamily 3, member A2 | 0.000388605 | 424.5 | 612.5 | 703.0 |
| 255 | 243225_PM_at | LOC283481 | hypothetical LOC283481 | 0.000388527 | 62.6 | 42.2 | 39.2 |
| 256 | 1554676_PM_at | SRGN | serglycin | 0.000399135 | 11.6 | 12.7 | 15.0 |
| 257 | 202748_PM_at | GBP2 | guanylate binding protein 2, interferon-inducible | 0.000406447 | 393.4 | 258.6 | 446.1 |
| 258 | 238654_PM_at | VSIG10L | V-set and immunoglobulin domain containing 10 like | 0.000411449 | 15.7 | 19.5 | 19.7 |
| 259 | 218949_PM_s_at | QRSL1 | glutaminyl-tRNA synthase (glutamine-hydrolyzing)-like 1 | 0.000413577 | 154.7 | 217.8 | 188.1 |
| 260 | 230306_PM_at | VPS26B | vacuolar protein sorting 26 homolog B (S. pombe) | 0.000420436 | 80.8 | 66.4 | 59.0 |
| 261 | 204450_PM_x_at | APOA1 | apolipoprotein A-I | 0.000427479 | 11811.2 | 13302.5 | 13014.4 |
| 262 | 213932_PM_x_at | HLA-A | major histocompatibility complex, class I, A | 0.000435087 | 7218.3 | 9083.8 | 10346.9 |
| 263 | 201641_PM_at | BST2 | bone marrow stromal cell antigen 2 | 0.000438494 | 217.2 | 396.5 | 401.8 |
| 264 | 1552275_PM_s_at | PXK | PX domain containing serine/threonine kinase | 0.000438718 | 24.7 | 38.6 | 34.4 |
| 265 | 210633_PM_x_at | KRT10 | keratin 10 | 0.000438865 | 535.9 | 466.6 | 443.1 |
| 266 | 217874_PM_at | SUCLG1 | succinate-CoA ligase, alpha subunit | 0.000441648 | 2582.3 | 3199.8 | 3034.6 |
| 267 | 223192_PM_at | SLC25A28 | solute carrier family 25, member 28 | 0.000456748 | 157.1 | 178.0 | 220.5 |
| 268 | 204820_PM_s_at | BTN3A2 /// BTN3A3 | butyrophilin, subfamily 3, member A2 /// butyrophilin, subfamily 3, member A3 | 0.000457313 | 1264.5 | 1537.9 | 1932.9 |
| 269 | 32069_PM_at | N4BP1 | NEDD4 binding protein 1 | 0.00045791 | 320.7 | 400.4 | 402.0 |
| 270 | 208870_PM_x_at | ATP5C1 | ATP synthase, H+ transporting, mitochondrial F1 complex, gamma polypeptide 1 | 0.000464012 | 3210.8 | 3791.7 | 3616.3 |
| 271 | 207104_PM_x_at | LILRB1 | leukocyte immunoglobulin-like receptor, subfamily B (with TM and ITIM domains), member | 0.000468733 | 52.9 | 52.0 | 80.6 |
| 272 | 209035_PM_at | MDK | midkine (neurite growth-promoting factor 2) | 0.000469597 | 18.5 | 25.2 | 30.3 |
| 273 | 230307_PM_at | LOC100129794 | similar to hCG1804255 | 0.000471715 | 17.3 | 14.8 | 13.5 |
| 274 | 225255_PM_at | MRPL35 | mitochondrial ribosomal protein L35 | 0.000478299 | 44.4 | 59.0 | 49.3 |
| 275 | 229625_PM_at | GBP5 | guanylate binding protein 5 | 0.000478593 | 243.9 | 147.4 | 393.5 |
| 276 | 209140_PM_x_at | HLA-B | major histocompatibility complex, class I, B | 0.000478945 | 8305.0 | 10032.9 | 11493.8 |
| 277 | 210905_PM_x_at | POU5F1P4 | POU class 5 homeobox 1 pseudogene 4 | 0.000492713 | 11.9 | 13.7 | 13.9 |
| 278 | 218480_PM_at | AGBL5 | ATP/GTP binding protein-like 5 | 0.000494707 | 23.8 | 20.7 | 18.1 |
| 279 | 209253_PM_at | SORBS3 | sorbin and SH3 domain containing 3 | 0.000495796 | 97.5 | 86.2 | 78.2 |

TABLE 6-continued 320 probesets that distinguish AR vs. HCV vs. HCV + AR in Liver Biopsies

| # | Probeset ID | Gene Symbol | Gene Title | p-value (Phenotype) | AR - Mean | HCV - Mean | HCV + AR - Mean |
|---|---|---|---|---|---|---|---|
| 280 | 207801_PM_s_at | RNF10 | ring finger protein 10 | 0.000508149 | 374.0 | 297.5 | 327.3 |
| 281 | 212539_PM_at | CHD1L | chromodomain helicase DNA binding protein 1-like | 0.000509089 | 482.2 | 677.2 | 613.0 |
| 282 | 224492_PM_s_at | ZNF627 | zinc finger protein 627 | 0.000513422 | 127.6 | 168.3 | 125.0 |
| 283 | 1557186_PM_s_at | TPCN1 | two pore segment channel 1 | 0.000513966 | 26.5 | 21.5 | 22.4 |
| 284 | 203610_PM_s_at | TRIM38 | tripartite motif-containing 38 | 0.000514783 | 100.5 | 139.2 | 156.0 |
| 285 | 211530_PM_x_at | HLA-G | major histocompatibility complex, class I, G | 0.000525417 | 1034.7 | 1429.2 | 1621.6 |
| 286 | 201421_PM_s_at | WDR77 | WD repeat domain 77 | 0.000527341 | 114.5 | 143.9 | 133.4 |
| 287 | 200617_PM_at | MLEC | malectin | 0.000529672 | 244.8 | 174.2 | 147.7 |
| 288 | 1555982_PM_at | ZFYVE16 | zinc finger, FYVE domain containing 16 | 0.000550743 | 27.5 | 35.4 | 27.8 |
| 289 | 211345_PM_x_at | EEF1G | eukaryotic translation elongation factor 1 gamma | 0.000555581 | 4011.7 | 3333.0 | 3247.8 |
| 290 | 1555202_PM_a_at | RPRD1A | regulation of nuclear pre-mRNA domain containing 1A | 0.000561763 | 14.0 | 17.2 | 14.3 |
| 291 | 218304_PM_at | OSBPL11 | oxysterol binding protein-like 11 | 0.000565559 | 230.5 | 347.9 | 328.7 |
| 292 | 219464_PM_at | CA14 | carbonic anhydrase XIV | 0.000570778 | 64.9 | 43.5 | 32.6 |
| 293 | 204278_PM_s_at | EBAG9 | estrogen receptor binding site associated, antigen, 9 | 0.000570888 | 482.5 | 591.0 | 510.6 |
| 294 | 218298_PM_s_at | C14orf159 | chromosome 14 open reading frame 159 | 0.000571869 | 411.1 | 515.6 | 573.0 |
| 295 | 213675_PM_at | — | — | 0.000576321 | 39.1 | 27.4 | 25.2 |
| 296 | 1555097_PM_a_at | PTGFR | prostaglandin F receptor (FP) | 0.000581257 | 11.0 | 12.8 | 14.0 |
| 297 | 209056_PM_s_at | CDC5L | CDC5 cell division cycle 5-like (S. pombe) | 0.000582594 | 552.0 | 682.3 | 659.9 |
| 298 | 208912_PM_s_at | CNP | 2',3'-cyclic nucleotide 3' phosphodiesterase | 0.00058579 | 308.8 | 415.8 | 392.9 |
| 299 | 227018_PM_at | DPP8 | dipeptidyl-peptidase 8 | 0.000587266 | 29.6 | 38.2 | 41.9 |
| 300 | 224650_PM_at | MAL2 | mal, T-cell differentiation protein 2 | 0.000592979 | 600.4 | 812.5 | 665.3 |
| 301 | 217492_PM_s_at | PTEN /// PTENP1 | phosphatase and tensin homolog /// phosphatase and tensin homolog pseudogene 1 | 0.000601775 | 545.5 | 511.2 | 426.0 |
| 302 | 211654_PM_x_at | HLA-DQB1 | major histocompatibility complex, class II, DQ beta 1 | 0.000608592 | 538.8 | 350.2 | 744.4 |
| 303 | 220312_PM_at | FAM83E | family with sequence similarity 83, member E | 0.000609835 | 16.0 | 13.9 | 13.7 |
| 304 | 228230_PM_at | PRIC285 | peroxisomal proliferator-activated receptor A interacting complex 285 | 0.00061118 | 42.0 | 55.4 | 57.6 |
| 305 | 215171_PM_s_at | TIMM17A | translocase of inner mitochondrial membrane 17 homolog A (yeast) | 0.000624663 | 1432.1 | 1905.5 | 1715.4 |
| 306 | 228912_PM_at | VIL1 | villin 1 | 0.000630544 | 53.0 | 29.5 | 27.6 |
| 307 | 203047_PM_at | STK10 | serine/threonine kinase 10 | 0.000638877 | 41.0 | 39.1 | 54.7 |
| 308 | 232617_PM_at | CTSS | cathepsin S | 0.000640978 | 1192.9 | 1083.0 | 1561.2 |
| 309 | 236219_PM_at | TMEM20 | transmembrane protein 20 | 0.000648505 | 20.5 | 38.9 | 36.1 |
| 310 | 240681_PM_at | — | — | 0.000649144 | 140.6 | 202.3 | 192.8 |
| 311 | 1553317_PM_s_at | GPR82 | G protein-coupled receptor 82 | 0.000667359 | 13.3 | 20.1 | 21.2 |
| 312 | 212869_PM_x_at | TPT1 | tumor protein, translationally-controlled 1 | 0.000669242 | 14240.7 | 13447.2 | 13475.2 |
| 313 | 219356_PM_s_at | CHMP5 | chromatin modifying protein 5 | 0.000670413 | 1104.5 | 1310.4 | 1322.9 |
| 314 | 1552555_PM_at | PRSS36 | protease, serine, 36 | 0.000676354 | 14.2 | 12.9 | 11.8 |
| 315 | 203147_PM_s_at | TRIM14 | tripartite motif-containing 14 | 0.000676359 | 334.8 | 419.3 | 475.4 |
| 316 | 43511_PM_s_at | — | — | 0.000678774 | 70.7 | 60.9 | 80.0 |
| 317 | 221821_PM_s_at | C12orf41 | chromosome 12 open reading frame 41 | 0.000683679 | 180.0 | 213.8 | 206.9 |
| 318 | 218909_PM_at | RPS6KC1 | ribosomal protein S6 kinase, 52 kDa, polypeptide 1 | 0.000686673 | 105.8 | 155.8 | 151.5 |
| 319 | 232724_PM_at | MS4A6A | membrane-spanning 4-domains, subfamily A, member 6A | 0.000686877 | 106.7 | 108.3 | 160.4 |
| 320 | 218164_PM_at | SPATA20 | spermatogenesis associated 20 | 0.000693114 | 181.5 | 130.4 | 156.0 |

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, ATCC deposits, patents and patent applications cited herein are hereby expressly incorporated by reference in their entirety and for all purposes as if each is individually so denoted.

We claim:

1. A method of detecting gene expression, comprising:
 (a) providing (i) a sample of nucleic acids from a subject who has undergone a liver transplant who is receiving an immunosuppressive drug, and (ii) a set of probes that detect at least five genes selected from the group consisting of LYST, 241038 PM at, 230776 PM at, PRUNE2, LOC44Q434, 243625 PM at, C18orf49, DNAJC3, 1557733 PM a at, GRAMD1B, MGC21881, PIK3R5, PPTC7, KLHL34, TIMM10, NTSE, NOG, SLC6A6, UBE2J1, 207737 PM at, CDKN2A, JMJD1C, MX1, 243819 PM at, 210524 PM x at, STMN1, ATP8A2, SLC16A10, LAPTM4B, LOC44Q434, MBP, HSH2D, CXCR6, DLGAPS, NKG7, 1570597 PM at, PLK1S1, PATL2, MEST, SYNM, BICD2, UEVLD, NGFRAP1, ITGA6, SP1, FAM179A, FGFR2, 243756 PM at, MCM4, TNEAIP3, GBPS, DEPDCI, NEK2, ID2///ID2B, RANBP9, OASL, ZCCHC2, TYMS, SETX, VAMPS, IGF2BP3, GZMB, TYMS, 240507 PM at, MMP1, NDE1, LOC339988, NCAPG, LGMN, 236191 PM at, STOML1, MAP3K2, 241692 PM at, CENPM, TBX21, 233700 PM at, RPS10///RPS10P7, SIAE, CTBP2, NUAK1, ELL, LOC641518, C3orfl4, OASL, CLICS, 237538 PM at, GPS, CCL4, NCAM1, MT1F, LIMS1, EIF2AK2, FGFR2, SLAMF8, GSTOI, MT1X, YPELI, IGF2BP3, REC8, ERBB2, TFPI, MT1E, PRF1, SOX13, STATE POLE2, MMRN1, OAS3, KIAA0101, STAT2, 226579 PM at, TIMM10, C19orf66, RFFL, FAM125A, PPP1R12B, APOL6, TMLHE, KLRD1, NOTCH2, GAL3ST4, C5orf56, XAF1, 240733 PM at, RRM2, PICALM, ACOT4, ITGA6, GZMH, HOXC4, VAMP5, LILRA2, LPCAT1, C19orf66, LQC100507192, 236899 PM at, 220467 PM at, SPON2, CSF2RA, 222058 PM at, CDCA7, LQC100131733, WHSC1L1, SOCS3, LOC284475, PLK4, RGS1, 234089 PM at, ADAT2, ZNF496, HERC5, KLHL24, CNPY3, SH2D3C, TNFSF13B, GNGT2, 239979 PM at, FUT6, LOC339988, RRM2, KIAA1324, 243947 PM s at, ISG15, CCNB2, CTBP2, CSF2RA, APOBEC3G, NCAM1, INPP5D, HLA-A, ZNF398, LOC374491, 220711 PM at, IL11RA, METTL7B, SP110, 242367 PM at, PARP12, OAS2, ADAM 17, 1570645 PM at, CSF2RA, RNF165, 236545 PM at, ZC3HAV1L, 239798 PM at, HERC4, CAMTA1, TPM1, GPA33, XAFI, RABSA, Clorf228, B4GALNT3, IFITM1, SLC2A10, IFI44L, PTGDR, AKAPS, CSF2RA, 237240 PM at, FGFBP2, S1PR5, MFSD4, LQC100240735///LOC4Q1522, MAN1A1, 222246 PM at, IL1RN, RARRES3, DHX58, IFIT3, ENOI, EMR3, EIF2AK2, GSPTE ZNF398, ID2, ARHGAP9, LOC643Q72, 233957 PM at, PUS3, RAP 1 GAP, HERC6, MX2, FZD3, AGMAT, MMP19, 221038 PM at, 233425 PM at, LQC100306951, 1560999 PM a at, RNF213, 1559110 PM at, IL4, GATA2, CTLA4, ZCRB1, DHRS7, KRT10, ZWINT, FBXL20, 234196 PM at, SRPK2, KIR3DL1///KIR3DL2///LOC727787, DNAH12, GPR56, ABCA9, WDFY4, IL1RN, CCR5, SLAMF8, 240438 PM at, PGM5, TREX1, 1566201 PM at, PDC3CD, SVIL, 244846 PM at, IRF7, ZBP 1, MPZL2, SPRED2, 241038 PM at, 207737 PM at, 1557733 PM a at, PLK1SE NOG, LAPTM4B, 241692 PM at, 230776 PM at, NGFRAP1, CLIC5, SLC16A10, KLHL34, PDC3R5, HSH2D, NTSE, ATP8A2, MGC21881, MX1, LOC374491, GAL3ST4, EIF2AK2, ITGA6, FAM179A, Clorf228, GP5, FUT6, ITGA6, S1PR5, OASL, 243819 PM at, HLA-DRB4///LOCI00509582, SPON2, TTTY10, OASL, PATL2, LOC641518, YPELI, C18orf49, MMRN1, SP 140L, 240507 PM at, IGF2BP3, C3orfl4, 214376 PM at, FAM91A2///FLI39739///LOC 100286793///LOC728855///LOC728875, IL4, 243947 PM s at, EIF2AK2, LOCI00507192, MEST, TBX21, CCDC85C, MMP19, INPP5D, 220467 PM at, DSCI, OAS3, PRF1, 239798 PM at, ZBP 1, ADAR, GALM, 233121 PM at, RNF165, B4GALNT3, GZMB, KIAA0319L, Clorf57, FGFR2, BCAR4, LOC339988, TRIM39, FAM85A///FAM85B, LIMSI, ERBB2, 236191 PM at, HLA-A, MFSD4, NCAM1, GALM, 1566201 PM at, MX2, 237240 PM at, 232478 PM at, KIR2DL5A, 1569551 PM at, ZCCHC2, NUBI, PCDH9, RASGEF1A, 1560080 PM at, 243756 PM at, SYNM, CNPY3, RAPGEFL1, RIPK3, SOX13, KLRD1, GRAMD1B, LOC641365, TOR1B, SP110, TMLHE, 240438 PM at, SERPINE2, IER2, 234089 PM at, GNGT2, DEPDC1, 242096 PM at, NFKBID, EPHX2, PRF1, FGFBP2, XRCC4, AKAP5, XCL1 ///XCL2, 237221 PM at, 232793 PM at, 239479 PM x at, 1558836 PM at, LOC339988, IL11RA, 236220 PM at, B3GALNT1, GRHL1, LEF1, LQC100507492, DAAM1, STOX1, XCLI, VAMP5, LGMN, IL6ST, SETX, FGD3, Clorf21, PRSS23, KLRD1, 212444 PM at, 240893 PM at, C3orf52, UNKL, KIR3DL1///KIR3DL2///LOC727787, FLI35220, MMP28, PTGDR, HERC5, OASL, IFI44, DDX60, OAS1, CMPK2, IFIT1, MX1, RSAD2, OAS2, HERC6, ISG15, OAS1, IFI6, LAMP5, IFIH1, OAS3, IFIT3, IFIT2, IFI44L, EPSTI1, IFIT3, IFIT2, OAS2, KIAA0114, IFI27, PARP9, IRF7, USP18, XAF1, PLSCR1, EPSTI1, RTP4, SHISA5, NT5C3, 228275 PM at, XAF1, IFITM1, IFI44, OAS2, HIST2H2AA3///HIST2H2AA4, GALNTL4, PLSCR1, HIST2H2AA3///HIST2H2AA4, HIST2H2BE, DDO, HIST1H2AC, IFI35, PARP12, SP100, EIF3L, 230314 PM at, SP100, 236798 PM at, SULF2, FAM179A, SAMD9, HIST1H2BD, LOC728769, HIST1H2BD, IFITM1, TDRD7, CMTM4, DDX58, ZNFX1, WDR8, UNC119B, GPAA1, HLA-C, DDX58, C2orf60, LQC10050697, HDLBP, PXK, SP110, GPAA1, PDXK, DHX58, UBA7, LGALS3BP, HIST1H2BE, KDELCI, ARPC1A, EIF2AK2, TDQ2, Cllorf2, C4orf33, HLA-B, ZNF684, IRF9, TMEM41A, 239988 PM at, GPR82, PPIF, RPL15, ZNF684, YBX1, RPL4, MAYS, SERPINA7, TRIM22, RPL4, TMEM41A, PIK3AP1, EIF3F, PEX11A, PNPT1, CSAG2///CSAG3, SSU72, DDO, ADAR, SULF2, GPAA1, RPL4, EEF2, CIAPIN1, EEF2, IFIT5, DDX60L, PPIF, LAP3, IFIT5, ZC3HAV1, RPL5, HLA-B, PPP3CC, B2M, HCP5, CTSB, HDLBP, RPS15A, SP110, PATL2, ESAM, IL17RB, SP110, TR1M34///TRIM6-TRIM34, NR1H4, SP100, NR1H4, IL18BP, EIF2AK2, TDQ2, RPS6KA2, IP6K2, HLA-G, HIST1H2BB///HIST1H2BC///HIST1H2BD///HIST1H2BE///HIST1H2BG///HIST1H2BH///HIST1H2BI, ENO3, TRIM14, EEF1A1, PDHX, IL17RB, COG2, EIF4B, CBWD2, CMTM4, UGT1A8///UGT1A9, AFG3L2, LQC100506318, MARCO, HLA-A///LOC1005077Q3, ACVRL1, SECTM1, SFRP5, C5orf44, SAMD9, 230795 PM at, HSBP1, LYPLAL1, HLA-C, LQC100505759, APOAI, NMI, CHD1L, FAM149A, UBA3, TPT1, PXK, FAM149A, KRT10, ZC3HAV1, CC2D2B, SELE, HLA-A///HLA-F///HLA-J, PEX3, FAM125A, HLA-G, ORMDL1, 1566249 PM at, CMAS, IL17RB, GLTSCR2, ST6GALNAC6, SP110, H2BFS, CYP11A1, EIF1, HIST1H2BC, 232140 PM at, DOK2, KLRD1, TPT1, VIL1, HLA-G, P2RY12, TLK2, 211976 PM at, SLU7, ZC3HAV1, HK3, DNASE1L1, 224603 PM at, CHMP5, BTN3A3, GOLGA7, WARS, IDS, 1560023 PM x at, GPD1, CREB1, SAMD9L, ZDHHC2, ETV7, UBA7, CD47, STX17, KLRK1, 1563075 PM s at, PARP14, NECAPI, RPL5, HIST1H2BI, SEPTIN 4, 239979 PM at, SEPHSI, UBE2L6, EEF1G, LOC25845, HIST1H2BF, ATP SB, HLA-F, PCBP2, PIAS2, HLA-DOB1///LQC100133583, GMDS, SYNPQ2, FECH, HLA-C, RPL3, UGT2A3, TCIRG1, BTN3A2, LOC283481, SRGN, GBP2, VSIGIOL, ORSLI, VPS26B, APOA1, HLA-A, BST2, PXK, KRT10, SUCLG1, SLC25A28, BTN3A2///BTN3A3, N4BP1, ATP5C1, LILRB1, MDK, LQC100129794, MRPL35, GBP5, HLA-B, POU5F1P4, AGBL5, SORBS3, RNF10, CHD1L, ZNF627, TPCN1, TRIM38, HLA-G, WDR77, MLEC, ZFYVE16, EEF1G, RPRD1A, OSBPLII, CA14, EBAG9, C14orfl59, 213675 PM at, PTGFR, CDC5L, CNP, DPP8, MAL2, PTEN///PTENP1, HLA-DOB1, FAM83E, PRIC285, TIMM 17A, VIL1, STRIP, CTSS, TMEM20, 240681 PM at, GPR82, TPT1, CHMP5, PRSS36, TRIM14, 43511 PM s at, C12orf41, RPS6KCE MS4A6A, and SPATA20;

(b) detecting mRNA levels of genes in the sample from the subject who has undergone a livertransplant using a microarray or sequencing assay, wherein the genes include at least five genes selected from the group consisting of LYST, 241038 PM at, 230776 PM at, PRUNE2, LOC44Q434, 243625 PM at, C18orf49, DNAJC3, 1557733 PM a at, GRAMD1B, MGC21881, PIK3R5, PPTC7, KLHL34, TIMM10, NTSE, NOG, SLC6A6, UBE2J1, 207737 PM at, CDKN2A, JMJD1C, MX1, 243819 PM at, 210524 PM x at, STMN1, ATP8A2, SLC16A10, LAPTM4B, LOC44Q434, MBP, HSH2D, CXCR6, DLGAPS, NKG7, 1570597 PM at, PLK1S1, PATL2, MEST, SYNM, BICD2, UEVLD, NGFRAP1, ITGA6, SP1, FAM179A, FGFR2, 243756 PM at, MCM4, TNFAIP3, GBPS, DEPDCI, NEK2, ID2///ID2B, RANBP9, OASL, ZCCHC2, TYMS, SETX, VAMPS, IGF2BP3, GZMB, TYMS, 240507 PM at, MMP1, NDE1, LOC339988, NCAPG, LGMN, 236191 PM at, STOML1, MAP3K2, 241692 PM at, CENPM, TBX21, 233700 PM at, RPS10///RPS10P7, SIAE, CTBP2, NUAK1, ELL, LOC641518, C3orfl4, OASL, CLICS, 237538 PM at, GP5, CCL4, NCAM1, MT1F, LIMS1, EIF2AK2, FGFR2, SLAMF8, GSTOI, MT1X, YPELI, IGF2BP3, REC8, ERBB2, TFPI, MT1E, PRF1, SOX13, STATE POLE2, MMRN1, OAS3, KIAA0101, STAT2, 226579 PM at, TIMM10, C19orf66, RFFL, FAM125A, PPP1R12B, APOL6, TMLHE, KLRD1, NOTCH2, GAL3ST4, C5orf56, XAF1, 240733 PM at, RRM2, PICALM, ACOT4, ITGA6, GZMH, HOXC4, VAMP5, LILRA2, LPCAT1, C19orf66, LQC100507192, 236899 PM at, 220467 PM at, SPON2, CSF2RA, 222058 PM at, CDCA7, LQC100131733, WHSC1L1, SOCS3, LOC284475, PLK4, RGS1, 234089 PM at, ADAT2, ZNF496, HERC5, KLHL24, CNPY3, SH2D3C, TNFSF13B, GNGT2, 239979 PM at, FUT6, LOC339988, RRM2, KIAA1324, 243947 PM s at, ISG15, CCNB2, CTBP2, CSF2RA, APOBEC3G, NCAM1, INPP5D, HLA-A, ZNF398, LOC374491, 220711 PM at, IL11RA, METTL7B, SP110, 242367 PM at, PARP12, OAS2, ADAM 17, 1570645 PM at, CSF2RA, RNF165, 236545 PM at, ZC3HAV1L, 239798 PM at, HERC4, CAMTA1, TPM1, GPA33, XAFI, RABSA, Clorf228, B4GALNT3, IFITM1, SLC2A10, IFI44L, PTGDR, AKAPS, CSF2RA, 237240 PM at, FGFBP2, S1PR5, MFSD4, LQC100240735///LOC4Q1522, MAN1A1, 222246 PM at, IL1RN, RARRES3, DHX58, IFIT3, ENOI, EMR3, EIF2AK2, GSPTE ZNF398, ID2, ARHGAP9, LOC643Q72, 233957 PM at, PUS3, RAP 1 GAP, HERC6, MX2, FZD3, AGMAT, MMP19, 221038 PM at, 233425 PM at, LQC100306951, 1560999 PM a at, RNF213, 1559110 PM at, IL4, GATA2, CTLA4, ZCRB1, DHRS7, KRT10, ZWINT, FBXL20, 234196 PM at, SRPK2, KIR3DL1///KIR3DL2///LOC727787, DNAH12, GPR56, ABCA9, WDFY4, IL1RN, CCR5, SLAMF8, 240438 PM at, PGM5, TREX1, 1566201 PM at, PIK3CD, SVIL, 244846 PM at, IRF7, ZBP 1, MPZL2, SPRED2, 241038 PM at, 207737 PM at, 1557733 PM a at, PLK1SE NOG, LAPTM4B, 241692 PM at, 230776 PM at, NGFRAP1, CLIC5, SLC16A10, KLHL34, PIK3R5, HSH2D, NTSE, ATP8A2, MGC21881, MX1, LOC374491, GAL3ST4, EIF2AK2, ITGA6, FAM179A, Clorf228, GP5, FUT6, ITGA6, S1PR5, OASL, 243819 PM at, HLA-DRB4///LOCI00509582, SPON2, TTTY10, OASL, PATL2, LOC641518, YPELI, C18orf49, MMRN1, SP 140L, 240507 PM at, IGF2BP3, C3orfl4, 214376 PM at, FAM91A2///FLI39739///LOC 100286793///LOC728855///LOC728875, IL4, 243947 PM s at, EIF2AK2, LOCI00507192, MEST, TBX21, CCDC85C, MMP19, INPP5D, 220467 PM at, DSCI, OAS3, PRF1, 239798 PM at, ZBP 1, ADAR, GALM, 233121 PM at, RNF165, B4GALNT3, GZMB, KIAA0319L, Clorf57, FGFR2, BCAR4, LOC339988, TRIM39, FAM85A///FAM85B, LIMSI, ERBB2, 236191 PM at, HLA-A, MFSD4, NCAM1, GALM, 1566201 PM at, MX2, 237240 PM at, 232478 PM at, KIR2DL5A, 1569551 PM at, ZCCHC2, NUBI, PCDH9, RASGEF1A, 1560080 PM at, 243756 PM at, SYNM, CNPY3, RAPGEFL1, RIPK3, SOX13, KLRD1, GRAMD1B, LOC641365, TOR1B, SP110, TMLHE, 240438 PM at, SERPINE2, IER2, 234089 PM at, GNGT2, DEPDC1, 242096 PM at, NFKBID, EPHX2, PRF1, FGFBP2, XRCC4, AKAP5, XCL1///XCL2, 237221 PM at, 232793 PM at, 239479 PM x at, 1558836 PM at, LOC339988, IL11RA, 236220 PM at, B3GALNT1, GRHL1, LEF1, LQC100507492, DAAME STOXI, XCLI, VAMP5, LGMN, IL6ST, SETX, FGD3, Clorf21, PRSS23, KLRDI, 212444 PM at, 240893 PM at, C3orf52, UNKL, KIR3DL1///KIR3DL2///LOC727787, FLI35220, MMP28, PTGDR, HERC5, OASL, IFI44, DDX60, OASE CMPK2, IFIT1, MX1, RSAD2, OAS2, HERC6, ISG15, OAS1, IF16, LAMP5, IFIH1, OAS3, IFIT3, IFIT2, IFI44L, EPSTI1, IFIT3, IFIT2, OAS2, KIAA0114, IFI27, PARP9, IRF7, USP18, XAF1, PLSCR1, EPSTI1, RTP4, SHISA5, NT5C3, 228275 PM at, XAF1, IFITM1, IFI44, OAS2, HIST2H2AA3///HIST2H2AA4, GALNTL4, PLSCR1, HIST2H2AA3///HIST2H2AA4, HIST2H2BE, DDO, HIST1H2AC, IFI35, PARP12, SP100, EIF3L, 230314 PM at, SP100, 236798 PM at, SULF2, FAM179A, SAMD9, HIST1H2BD, LOC728769, HIST1H2BD, IFITM1, TDRD7, CMTM4, DDX58, ZNFX1, WDR8, UNC119B, GPAA1, HLA-C, DDX58, C2orf60, LQC10050697, HDLBP, PXK, SP110, GPAA1, PDXK, DHX58, UBA7, LGALS3BP, HIST1H2BE, KDELCE ARPC1A, EIF2AK2, TDQ2, C1orf2, C4orf33, HLA-B, ZNF684, IRF9, TMEM41A, 239988 PM at, GPR82, PPIF, RPL15, ZNF684, YBX1, RPL4, MAYS, SERPINA7, TRIM22, RPL4, TMEM41A, PIK3AP1, EIF3F, PEX11A, PNPTE CSAG2///CSAG3, SSU72, DDO, ADAR, SULF2, GPAA1, RPL4, EEF2, CIAPIN1, EEF2, IFIT5, DDX60L, PPIF, LAP3, IFIT5, ZC3HAV1, RPL5, HLA-B, PPP3CC, B2M, HCP5, CTSB, HDLBP, RPS15A, SP110, PATL2, ESAM, IL17RB, SP110, TR1M34///TRIM6-TRIM34, NR1H4, SP100, NR1H4, IL18BP, EIF2AK2, TDQ2, RPS6KA2, IP6K2, HLA-G, HIST1H2BB///HIST1H2BC///HIST1H2BD///HIST1H2BE///HIST1H2BG///HIST1H2BH///HIST1H2BI, ENO3, TRIM14, EEF1A1, PDHX, IL17RB, COG2, EIF4B, CBWD2, CMTM4, UGT1A8///UGT1A9, AFG3L2, LQC100506318, MARCO, HLA-A///LOC1005077Q3, ACVRL1, SECTM1, SFRP5, C5orf44, SAMD9, 230795 PM at, HSBP1, LYPLAL1, HLA-C, LQC100505759, APOAI, NMF CHD1L, FAM149A, UBA3, TPT1, PXK, FAM149A, KRT10, ZC3HAV1, CC2D2B, SELE, HLA-A///HLA-F///HLA-J, PEX3, FAM125A, HLA-G, ORMDL1, 1566249 PM at, CMAS, IL17RB, GLTSCR2, ST6GALNAC6, SP110, H2BFS, CYP11A1, EIF1, HIST1H2BC, 232140 PM at, DOK2, KLRD1, TPT1, VILI, HLA-G, P2RY12, TLK2, 211976 PM at, SLU7, ZC3HAV1, HK3, DNASE1L1, 224603 PM at, CHMP5, BTN3A3, GOLGA7, WARS, IDS, 1560023 PM x at, GPD1, CREB1, SAMD9L, ZDHHC2, ETV7, UBA7, CD47, STX17, KLRK1, 1563075 PM s at, PARP14, NECAPI, RPL5, HIST1H2BI, SEPTIN 4, 239979 PM at, SEPHSE UBE2L6, EEF1G, LOC25845, HIST1H2BF, ATP SB, HLA-F, PCBP2, PIAS2, HLA-DOB1///LQC100133583, GMDS, SYNPQ2, FECH, HLA-C, RPL3, UGT2A3, TCIRGE BTN3A2, LOC283481, SRGN, GBP2, VSIGIOL, ORSLI, VPS26B, APOAI, HLA-A, BST2, PXK, KRT10, SUCLGL SLC25A28, BTN3A2///BTN3A3, N4BP1, ATP5CL LILRB1, MDK, LQC100129794, MRPL35, GBP5, HLA-B, POU5F1P4, AGBL5, SORBS3, RNF10, CHD1L, ZNF627, TPCNI, TRIM38, HLA-G, WDR77, MLEC, ZFYVE16, EEF1G, RPRD1 A, OSBPL1E CA14, EBAG9, C14orfl59, 213675 PM at, PTGFR, CDC5L, CNP, DPP8, MAL2, PTEN///PTENP1, HLA-DOB1, FAM83E, PRIC285, TIMM 17A, VIL1, STRIP, CTSS, TMEM20, 240681 PM at, GPR82, TPT1, CHMP5, PRSS36, TRIM14, 43511 PM sat, C12orf41, RPS6KCE MS4A6A, and SPATA20, wherein the genes are detected by contacting the sample with probes specific for the at least five genes selected from the group consisting of LYST, 241038 PM at 230776 PM at PRUNE2, LOC44Q434, 243625 PM at, C18orf49, DNAJC3, 1557733 PM a at, GRAMD1B, MGC21881, PDC3R5, PPTC7, KLHL34, TIMM10, NT5E, NOG, SLC6A6, UBE2J1, 207737 PM at, CDKN2A, JMJD1C, MX1, 243819 PM at, 210524 PMx at, STMN1, ATP8A2, SLC16A10, LAPTM4B, LOC44Q434, MBP, HSH2D, CXCR6, DLGAPS, NKG7, 1570597 PM at, PLK1S1, PATL2, MEST, SYNM, BICD2, UEVLD, NGFRAP1, ITGA6, SP1, FAM179A, FGFR2, 243756 PM at, MCM4, TNFAIP3, GBPS, DEPDC1, NEK2, ID2///ID2B, RANBP9, OASL, ZCCHC2, TYMS, SETX, VAMP5, IGF2BP3, GZMB, TYMS, 240507 PM at, MMP1, NDE1, LOC339988, NCAPG, LGMN, 236191 PM at, STOML1, MAP3K2, 241692 PM at, CENPM, TBX21, 233700 PM at, RPS10///RPS10P7, SIAE, CTBP2, NUAK1, ELL, LOC641518, C3orfl4, OASL, CLICS, 237538 PM at, GPS, CCL4, NCAM1, MT1F, LIMS1, EIF2AK2, FGFR2, SLAMF8, GSTOI, MT1X, YPEL1, IGF2BP3, REC8, ERBB2, TFPI, MT1E, PRF1, SOX13, STATE POLE2, MMRN1, OAS3, KIAA0101, STAT2, 226579 PM at, TIMM10, C19orf66, RFFL, FAM125A, PPP1R12B, APOL6, TMLHE, KLRD1, NOTCH2, GAL3ST4, C5orf56, XAF1, 240733 PM at, RRM2, PICALM, ACOT4, ITGA6, GZMH, HOXC4, VAMP5, LILRA2, LPCAT1, C19orf66, LQC100507192, 236899 PM at, 220467 PM at, SPON2, CSF2RA, 222058 PM at, CDCA7, LQC100131733, WHSC1L1, SOCS3, LOC284475, PLK4, RGSI, 234089 PM at, ADAT2, ZNF496, HERC5, KLHL24, CNPY3, SH2D3C, TNFSF13B, GNGT2, 239979 PM at, FUT6, LOC339988, RRM2, KIAA1324, 243947 PM s at, ISG15, CCNB2, CTBP2, CSF2RA, APOBEC3G, NCAM1, INPP5D, HLA-A, ZNF398, LOC374491, 220711 PM at, IL1 IRA, METTL7B, SP110, 242367 PM at, PARP12, OAS2, ADAM 17, 1570645 PM at, CSF2RA, RNF165, 236545 PM at, ZC3HAV1L, 239798 PM at, HERC4, CAMTAI, TPM1, GPA33, XAF1, RABSA, C1orf228, B4GALNT3, IFITM1, SLC2A10, IFI44L, PTGDR, AKAPS, CSF2RA, 237240 PM at, FGFBP2, S1PR5, MFSD4, LQC100240735///LOC4Q1522, MAN1A1, 222246 PM at, IL1RN, RARRES3, DHX58, IFIT3, ENOI, EMR3, EIF2AK2, GSPT1, ZNF398, ID2, ARHGAP9, LOC643Q72, 233957 PM at, PUS3, RAP 1 GAP, HERC6, MX2, FZD3, AGMAT, MMP19, 221098 PM at, 233425 PM at, LQC100306951, 1560999 PM a at, RNF213, 1559110 PM at, IL4, GATA2, CTLA4, ZCRB1, DHRS7, KRT10, ZWINT, FBXL20, 234196 PM at, SRPK2, KIR3DL1///KIR3DL2///LOC727787, DNAH12, GPR56, ABCA9, WDFY4, IL1RN, CCR5, SLAMF8, 240438 PM at, PGM5, TREX1, 1566201 PM at, PDC3CD, SVIL, 244846 PM at, IRF7, ZBP 1, MPZL2, SPRED2, 241038 PM at, 207737 PM at, 1557733 PM a at, PLK1SE NOG, LAPTM4B, 241692 PM at, 230776 PM at, NGFRAP1, CLIC5, SLC16A10, KLHL34, PIK3R5, HSH2D, NT5E, ATP8A2, MGC21881, MX1, LOC374491, GAL3ST4, EIF2AK2, ITGA6, FAM179A, C1orf228, GP5, FUT6, ITGA6, S1PR5, OASL, 243819 PM at, HLA-DRB4///LOCI00509582, SPON2, TTTY10, OASL, PATL2, LOC641518, YPELI, C18orf49, MMRNI, SP 140L, 240507 PM at, IGF2BP3, C3orfl4, 214376 PM at, FAM91A2///FLI39739///LOC100286793///LOC728855///LOC728875, IL4, 243947 PM s at, EIF2AK2, LOCI00507192, MEST, TBX21, CCDC85C, MMP19, INPP5D, 220467 PM at, DSCI, OAS3, PRF1, 239798 PM at, ZBP 1, ADAR, GALM, 233121 PM at, RNE165, B4GALNT3, GZMB, KIAA0319L, C1orf57, FGFR2, BCAR4, LOC339988, TRIM39, FAM85A///
FAM85B, LIMSI, ERBB2, 236191 PM at, HLA-A,
MFSD4, NCAM1, GALM, 1566201 PM at, MX2,
237240 PM at, 232478 PM at, KIR2DL5A, 1569551
PM at, ZCCHC2, NUBI, PCDH9, RASGEF1A,
1560080 PM at, 243756 PM at, SYNM, CNPY3,
RAPGEFL1, RIPK3, SOX13, KLRD1, GRAMD1B,
LOC641365, TOR1B, SP110, TMLHE, 240438 PM at,
SERPINE2, IER2, 234089 PM at, GNGT2, DEPDC1,
242096 PM at, NFKBID, EPHX2, PRF1, FGFBP2,
XRCC4, AKAP5, XCL1///XCL2, 237221 PM at,
232793 PM at, 239479 PM x at, 1558836 PM at,
LOC339988, IL11RA, 236220 PM at, B3GALNT1,
GRHL1, LEFI, LQC100507492, DAAME STOXI,
XCLI, VAMP5, LGMN, IL6ST, SETX, FGD3,
Clorf21, PRSS23, KLRDI, 212444 PM at, 240893 PM
at, C3orf52, UNKL, KIR3DL1///KIR3DL2///
LOC727787, FLI35220, MMP28, PTGDR, HERC5,
OASL, IFI44, DDX60, OASE CMPK2, IFITI, MX1,
RSAD2, OAS2, HERC6, ISG15, OASE IFI6, LAMP5,
IFIH1, OAS3, IFIT3, IFIT2, IFI44L, EPSTII, IFIT3,
IFIT2, OAS2, KIAA0114, IFI27, PARP9, IRF7,
USP18, XAFI, PLSCRI, EPSTII, RTP4, SHISA5,
NT5C3, 228275 PM at, XAFI, IFITME IFI44, OAS2,
HIST2H2AA3///HIST2H2AA4, GALNTL4, PLSCR1,
HIST2H2AA3///HIST2H2AA4, HIST2H2BE, DDO,
HIST1H2AC, IFI35, PARP12, SP100, EIF3L, 230314
PM at, SP100, 236798 PM at, SULF2, FAM179A,
SAMD9, HIST1H2BD, LOC728769, HIST1H2BD,
IFITM1, TDRD7, CMTM4, DDX58, ZNFXI, WDR8,
UNC119B, GPAA1, HLA-C, DDX58, C2orf60,
LQC10050697, HDLBP, PXK, SP110, GPAA1,
PDXK, DHX58, UBA7, LGALS3BP, HIST1H2BE,
KDELC1, ARPC1A, EIF2AK2, TDQ2, Cllorf2,
C4orf33, HLA-B, ZNF684, IRF9, TMEM41A, 239988
PM at, GPR82, PPIF, RPL15, ZNF684, YBX1, RPL4,
MAYS, SERPINA7, TRIM22, RPL4, TMEM41A,
PIK3AP1, EIF3F, PEX11A, PNPTE CSAG2///CSAG3,
SSU72, DDO, ADAR, SULF2, GPAA1, RPL4, EEF2,
CIAPIN1, EEF2, IFIT5, DDX60L, PPIF, LAP3, IFIT5,
ZC3HAV1, RPL5, HLA-B, PPP3CC, B2M, HCP5,
CTSB, HDLBP, RPS15A, SP110, PATL2, ESAM,
IL17RB, SP110, TR1M34///TRIM6-TRIM34, NR1H4,
SP100, NR1H4, IL18BP, EIF2AK2, TDQ2, RPS6KA2,
IP6K2, HLA-G, HIST1H2BB///HIST1H2BC///
HIST1H2BD///HIST1H2BE///HIST1H2BG///
HIST1H2BH///HIST1H2BI, ENO3, TRIM14,
EEF1A1, PDHX, IL17RB, COG2, EIF4B, CBWD2,
CMTM4, UGT1A8///UGT1A9, AFG3L2,
LQC100506318, MARCO, HLA-A///LOC1005077Q3,
ACVRL1, SECTM1, SFRP5, C5orf44, SAMD9,
230795 PM at, HSBP1, LYPLAL1, HLA-C,
LQC100505759, APPAL NMF CHD1L, FAM149A,
UBA3, TPT1, PXK, FAM149A, KRT10, ZC3HAV1,
CC2D2B, SELE, HLA-A///HLA-F///HLA-J, PEX3,
FAM125A, HLA-G, ORMDL1, 1566249 PM at,
CMAS, IL17RB, GLTSCR2, ST6GALNAC6, SP110,
H2BFS, CYPIIAI, EIF1, HIST1H2BC, 232140 PM at,
DOK2, KLRD1, TPT1, VIL1, HLA-G, P2RY12,
TLK2, 211976 PM at, SLU7, ZC3HAV1, HK3,
DNASE1L1, 224603 PM at, CHMP5, BTN3A3,
GOLGA7, WARS, IDS, 1560023 PM x at, GPDL
CREB1, SAMD9L, ZDHHC2, ETV7, UBA7, CD47,
STX17, KLRK1, 1563075 PM s at, PARP14, NECAPI,
RPL5, HIST1H2BL SEPTIN 4, 239979 PM at, SEP-
HSE UBE2L6, EEF1G, LOC25845, HIST1H2BF, ATP
SB, HLA-F, PCBP2, PIAS2, HLA-DOB1///
LQC100133583, GMDS, SYNPQ2, FECH, HLA-C,
RPL3, UGT2A3, TCIRGE BTN3A2, LOC283481,
SRGN, GBP2, VSIG10L, ORSLI, VPS26B, APPAL
HLA-A, BST2, PXK, KRT10, SUCLGL SLC25A28,
BTN3A2///BTN3A3, N4BP1, ATP5CL LILRB1,
MDK, LQC100129794, MRPL35, GBP5, HLA-B,
POU5F1P4, AGBL5, SORBS3, RNF10, CHD1L,
ZNF627, TPCN1, TRIM38, HLA-G, WDR77, MLEC,
ZFYVE16, EEF1G, RPRD1A, OSBPL11, CA14,
EBAG9, C14orfl59, 213675 PM at, PTGFR, CDC5L,
CNP, DPP8, MAL2, PTEN///PTENP1, HLA-DOB1,
FAM83E, PRIC285, TIMM 17A, VILI, STRIP, CTSS,
TMEM20, 240681 PM at, GPR82, TPT1, CHMP5,
PRSS36, TRIM14, 43511 PM s at, C12orf41,
RPS6KCE MS4A6A, and SPATA20;

(c) applying a trained algorithm to the mRNA expression
levels detected in (b), wherein the algorithm classifies
mRNA expression as undergoing acute rejection or not
undergoing acute rejection and is trained on the at least
five genes selected from LYST, 241038 PM at, 230776
PM at, PRUNE2, LOC44Q434, 243625 PM at,
C18orf49, DNAJC3, 1557733 PM a at, GRAMD1B,
MGC21881, PIK3R5, PPTC7, KLHL34, TIMM10,
NTSE, NOG, SLC6A6, UBE2J1, 207737 PM at,
CDKN2A, JMJD1C, MX1, 243819 PM at, 210524 PM
x at, STMN1, ATP8A2, SLC16A10, LAPTM4B,
LQC440434, MBP, HSH2D, CXCR6, DLGAPS,
NKG7, 1570597 PM at, PLK1S1, PATL2, MEST,
SYNM, BICD2, UEVLD, NGFRAP1, ITGA6, SP1,
FAM179A, FGFR2, 243756 PM at, MCM4, TNFAIP3,
GBPS, DEPDC1, NEK2, ID2///ID2B, RANBP9,
OASL, ZCCHC2, TYMS, SETX, VAMPS, IGF2BP3,
GZMB, TYMS, 240507 PM at, MMP1, NDE1,
LOC339988, NCAPG, LGMN, 236191 PM at,
STOML1, MAP3K2, 241692 PM at, CENPM, TBX21,
233700 PM at, RPS10///RPS10P7, SIAE, CTBP2,
NUAK1, ELL, LOC641518, C3orfl4, OASL, CLICS,
237538 PM at, GP5, CCL4, NCAM1, MT1F, LIMS1,
EIF2AK2, FGFR2, SLAMF8, GSTOI, MT1X, YPEL1,
IGF2BP3, REC8, ERBB2, TFPI, MT1E, PRF1,
SOX13, STATE POLE2, MMRN1, OAS3, KIAA0101,
STAT2, 226579 PM at, TIMM10, C19orf66, RFFL,
FAM125A, PPP1R12B, APOL6, TMLHE, KLRD1,
NOTCH2, GAL3ST4, C5orf56, XAFI, 240733 PM at,
RRM2, PICALM, ACOT4, ITGA6, GZMH, HOXC4,
VAMP5, LILRA2, LPCAT1, C19orf66,
LQC100507192, 236899 PM at, 220467 PM at,
SPON2, CSF2RA, 222058 PM at, CDCA7,
LQC100131733, WHSC1L1, SOCS3, LOC284475,
PLK4, RGS1, 234089 PM at, ADAT2, ZNF496,
HERC5, KLHL24, CNPY3, SH2D3C, TNFSF13B,
GNGT2, 239979 PM at, FUT6, LOC339988, RRM2,
KIAA1324, 243947 PM s at, ISG15, CCNB2, CTBP2,
CSF2RA, APOBEC3G, NCAM1, INPP5D, HLA-A,
ZNF398, LOC374491, 220711 PM at, IL11RA,
METTL7B, SP110, 242367 PM at, PARP12, OAS2,
ADAM 17, 1570645 PM at, CSF2RA, RNF165,
236545 PM at, ZC3HAV1L, 239798 PM at, HERC4,
CAMTA1, TPM1, GPA33, XAFI, RABSA, Clorf228,
B4GALNT3, IFITMI, SLC2A10, IFI44L, PTGDR,
AKAPS, CSF2RA, 237240 PM at, FGFBP2, S1PR5,
MFSD4, LQC100240735///LOC4Q1522, MAN1A1,
222246 PM at, IL1RN, RARRES3, DHX58, IFIT3,
ENOI, EMR3, EIF2AK2, GSPT1, ZNF398, ID2,
ARHGAP9, LOC643Q72, 233957 PM at, PUS3, RAP
1 GAP, HERC6, MX2, FZD3, AGMAT, MMP19,
221038 PM at, 233425 PM at, LQC100306951, 1560999 PM a at, RNF213, 1559110 PM at, IL4, GATA2, CTLA4, ZCRB1, DHRS7, KRT10, ZWINT, FBXL20, 234196 PM at, SRPK2, KIR3DL1///KIR3DL2///LOC727787, DNAH12, GPR56, ABCA9, WDFY4, IL1RN, CCR5, SLAMF8, 240438 PM at, PGM5, TREX1, 1566201 PM at, PIK3CD, SVIL, 244846 PM at, IRF7, ZBP 1, MPZL2, SPRED2, 241038 PM at, 207737 PM at, 1557733 PM a at, PLK1S1, NOG, LAPTM4B, 241692 PM at, 230776 PM at, NGFRAP1, CLIC5, SLC16A10, KLHL34, PIK3R5, HSH2D, NT5E, ATP8A2, MGC21881, MX1, LOC374491, GAL3ST4, EIF2AK2, ITGA6, FAM179A, C1orf228, GP5, FUT6, ITGA6, S1PR5, OASL, 243819 PM at, HLA-DRB4///LOC100509582, SPON2, TTTY10, OASL, PATL2, LOC641518, YPEL1, C18orf49, MMRN1, SP 140L, 240507 PM at, IGF2BP3, C3orf14, 214376 PM at, FAM91A2///FLI39739///LOC 100286793///LOC728855///LOC728875, IL4, 243947 PM s at, EIF2AK2, LOC100507192, MEST, TBX21, CCDC85C, MMP19, INPP5D, 220467 PM at, DSC1, OAS3, PRF1, 239798 PM at, ZBP 1, ADAR, GALM, 233121 PM at, RNF165, B4GALNT3, GZMB, KIAA0319L, C1orf57, FGFR2, BCAR4, LOC339988, TRIM39, FAM85A///FAM85B, LIMS1, ERBB2, 236191 PM at, HLA-A, MFSD4, NCAM1, GALM, 1566201 PM at, MX2, 237240 PM at, 232478 PM at, KIR2DL5A, 1569551 PM at, ZCCHC2, NUB1, PCDH9, RASGEF1A, 1560080 PM at, 243756 PM at, SYNM, CNPY3, RAPGEFL1, RIPK3, SOX13, KLRD1, GRAMD1B, LOC641365, TOR1B, SP110, TMLHE, 240438 PM at, SERPINE2, IER2, 234089 PM at, GNGT2, DEPDC1, 242096 PM at, NFKBID, EPHX2, PRF1, FGFBP2, XRCC4, AKAP5, XCL1///XCL2, 237221 PM at, 232793 PM at, 239479 PM x at, 1558836 PM at, LOC339988, IL11RA, 236220 PM at, B3GALNT1, GRHL1, LEF1, LQC100507492, DAAM1, STOX1, XCL1, VAMP5, LGMN, IL6ST, SETX, FGD3, C1orf21, PRSS23, KLRD1, 212444 PM at, 240893 PM at, C3orf52, UNKL, KIR3DL1///KIR3DL2///LOC727787, FLI35220, MMP28, PTGDR, HERC5, OASL, IFI44, DDX60, OAS1, CMPK2, IFIT1, MX1, RSAD2, OAS2, HERC6, ISG15, OASI, IF16, LAMP3, IFIH1, OAS3, IFIT3, IFIT2, IFI44L, EPSTI1, IFIT3, IFIT2, OAS2, KIAA0114, IFI27, PARP9, IRF7, USP18, XAF1, PLSCRI, EPSTI1, RTP4, SHISA5, NT5C3, 228275 PM at, XAF1, IFITM1, IFI44, OAS2, HIST2H2AA3///HIST2H2AA4, GALNTL4, PLSCR1, HIST2H2AA3///HIST2H2AA4, HIST2H2BE, DDO, HIST1H2AC, IFI35, PARP12, SP100, EIF3L, 230314 PM at, SP100, 236798 PM at, SULF2, FAM179A, SAMD9, HIST1H2BD, LOC728769, HIST1H2BD, IFITM1, TDRD7, CMTM4, DDX58, ZNFX1, WDR8, UNC119B, GPAA1, HLA-C, DDX58, C2orf60, LQC10050697, HDLBP, PXK, SP110, GPAA1, PDXK, DHX58, UBA7, LGALS3BP, HIST1H2BE, KDELC1, ARPC1A, EIF2AK2, TDQ2, C11orf2, C4orf33, HLA-B, ZNF684, IRF9, TMEM41A, 239988 PM at, GPR82, PPIF, RPL15, ZNF684, YBX1, RPL4, MAY5, SERPINA7, TRIM22, RPL4, TMEM41A, PIK3AP1, EIF3F, PEX11A, PNPT1, CSAG2///CSAG3, SSU72, DDO, ADAR, SULF2, GPAA1, RPL4, EEF2, CIAPIN1, EEF2, IFIT5, DDX60L, PPIF, LAP3, IFIT5, ZC3HAV1, RPL5, HLA-B, PPP3CC, B2M, HCP5, CTSB, HDLBP, RPS15A, SP110, PATL2, ESAM, IL17RB, SP110, TR1M34///TRIM6-TRIM34, NR1H4, SP100, NR1H4, IL18BP, EIF2AK2, TDQ2, RPS6KA2, IP6K2, HLA-G, HIST1H2BB///HIST1H2BC///HIST1H2BD///HIST1H2BE///HIST1H2BG///HIST1H2BH///HIST1H2BI, ENO3, TRIM14, EEF1A1, PDHX, IL17RB, COG2, EIF4B, CBWD2, CMTM4, UGT1A8///UGT1A9, AFG3L2, LQC100506318, MARCO, HLA-A///LOC1005077Q3, ACVRL1, SECTM1, SFRP5, C5orf44, SAMD9, 230795 PM at, HSBP1, LYPLAL1, HLA-C, LQC100505759, APOA1, NMI, CHD1L, FAM149A, UBA3, TPT1, PXK, FAM149A, KRT10, ZC3HAV1, CC2D2B, SELE, HLA-A///HLA-F///HLA-J, PEX3, FAM125A, HLA-G, ORMDL1, 1566249 PM at, CMAS, IL17RB, GLTSCR2, ST6GALNAC6, SP110, H2BFS, CYP11A1, EIF1, HIST1H2BC, 232140 PM at, DOK2, KLRD1, TPT1, VIL1, HLA-G, P2RY12, TLK2, 211976 PM at, SLU7, ZC3HAV1, HK3, DNASE1L1, 224603 PM at, CHMP5, BTN3A3, GOLGA7, WARS, IDS, 1560023 PM x at, GPDE CREB1, SAMD9L, ZDHHC2, ETV7, UBA7, CD47, STX17, KLRK1, 1563075 PM s at, PARP14, NECAPI, RPL5, HIST1H2BL SEPTIN 4, 239979 PM at, SEP-HSE UBE2L6, EEF1G, LOC25845, HIST1H2BF, ATP SB, HLA-F, PCBP2, PIAS2, HLA-DOB1///LQC100133583, GMDS, SYNPQ2, FECH, HLA-C, RPL3, UGT2A3, TCIRGE BTN3A2, LOC283481, SRGN, GBP2, VSIG10L, ORSLI, VPS26B, APOA1, HLA-A, BST2, PXK, KRT10, SUCLGE SLC25A28, BTN3A2///BTN3A3, N4BP1, ATP5CE LILRB1, MDK, LQC100129794, MRPL35, GBP5, HLA-B, POU5F1P4, AGBL5, SORBS3, RNE10, CHD1L, ZNE627, TPCNETRIM38, HLA-G, WDR77, MLEC, ZFYVE16, EEF1G, RPRD1A, OSBPL11, CA14, EBAG9, C14orf59, 213675 PM at, PTGFR, CDC5L, CNP, DPP8, MAL2, PTEN///PTENP1, HLA-DOBI, FAM83E, PRIC285, TIMM 17A, VILE STRIP, CTSS, TMEM20, 240681 PM at, GPR82, TPT1, CHMP5, PRSS36, TRIM14, 43511 PM s at, C12orf41, RPS6KCE MS4A6A, and SPATA20, thereby classifying the sample as undergoing acute rejection or not undergoing acute rejection; and (d) administering the immunosuppressive drug at an altered dose or frequency in response to the classification of the sample as undergoing acute rejection or not undergoing acute rejection in (c).

2. The method of claim 1, wherein the mRNA levels of up to 100 genes selected from the group consisting of LYST, 241038 PM at, 230776 PM at, PRUNE2, LOC440434, 243625 PM at, C18orf49, DNAJC3, 1557733 PM a at, GRAMD1B, MGC21881, PIK3R5, PPTC7, KLHL34, TIMM10, NT5E, NOG, SLC6A6, UBE2J1, 207737 PM at, CDKN2A, JMJD1C, MX1, 243819 PM at, 210524 PM x at, STMN1, ATP8A2, SLC16A10, LAPTM4B, LOC440434, MBP, HSH2D, CXCR6, DLGAPS, NKG7, 1570597 PM at, PLK1S1, PATL2, MEST, SYNM, BICD2, UEVLD, NGFRAP1, ITGA6, SP1, FAM179A, FGFR2, 243756 PM at, MCM4, TNFAIP3, GBPS, DEPDC1, NEK2, ID2///ID2B, RANBP9, OASL, ZCCHC2, TYMS, SETX, VAMPS, IGF2BP3, GZMB, TYMS, 240507 PM at, MMP1, NDE1, LOC339988, NCAPG, LGMN, 236191 PM at, STOML1, MAP3K2, 241692 PM at, CENPM, TBX21, 233700 PM at, RPS10///RPS10P7, SIAE, CTBP2, NUAK1, ELL, LOC641518, C3orf14, OASL, CLICS, 237538 PM at, GP5, CCL4, NCAM1, MT1F, EIF2AK2, FGFR2, SLAMF8, GSTO1, MT1X, YPEL1, IGF2BP3, REC8, ERBB2, TFPI, MT1E, PRF1, SOX13, STAT1, POLE2, MMRN1, OAS3, KIAA0101, STAT2, 226579 PM at, TIMM10, C19orf66, RFFL, FAM125A, PPP1R12B, APOL6, TMLHE, KLRD1, NOTCH2, GAL3ST4, C5orf56, XAF1, 240733 PM at, RRM2, PICALM, ACOT4, ITGA6, GZMH, HOXC4, VAMP5, LILRA2, LPCAT1, C19orf66, LOC100507192, 236899 PM at, 220467 PM at, SPON2, CSF2RA, 222058 PM at, CDCA7, LOC100131733, WHSC1L1, SOCS3, LOC284475, PLK4, RGS1, 234089 PM at, ADAT2, ZNF496, HERC5, KLHL24, CNPY3, SH2D3C, TNFSF13B, GNGT2, 239979 PM at, FUT6, LOC339988, RRM2, KIAA1324, 243947 PM s at, ISG15, CCNB2, CTBP2, CSF2RA, APOBEC3G, NCAM1, INPP5D, HLA-A, ZNF398, LOC374491, 220711 PM at, IL11RA, METTL7B, SP110, 242367 PM at, PARP12, OAS2, ADAM17, 1570645 PM at, CSF2RA, RNF165, 236545 PM at, ZC3HAV1L, 239798 PM at, HERC4, CAMTA1, TPM1, GPA33, XAF1, RABSA, C1orf228, B4GALNT3, IFITM1, SLC2A10, IFI44L, PTGDR, AKAPS, CSF2RA, 237240 PM at, FGFBP2, S1PR5, MFSD4, LOC100240735///LOC401522, MAN1A1, 222246 PM at, IL1RN, RARRES3, DHX58, IFIT3, ENO1, EMR3, EIF2AK2, GSPT1, ZNF398, ID2, ARHGAP9, LOC643072, 233957 PM at, PUS3, RAP1GAP, HERC6, MX2, FZD3, AGMAT, MMP19, 221038 PM at, 233425 PM at, LOC100306951, 1560999 PM a at, RNF213, 1559110 PM at, IL4, GATA2, CTLA4, ZCRB1, DHRS7, KRT10, ZWINT, FBXL20, 234196 PM at, SRPK2, KIR3DL1///KIR3DL2///LOC727787, DNAH12, GPR56, ABCA9, WDFY4, IL1RN, CCR5, SLAMF8, 240438 PM at, PGM5, TREX1, 1566201 PM at, PIK3CD, SVIL, 244846 PM at, IRF7, ZBP 1, MPZL2, SPRED2, 241038 PM at, 207737 PM at, 1557733 PM a at, PLK1S1, NOG, LAPTM4B, 241692 PM at, 230776 PM at, NGFRAP1, CLIC5, SLC16A10, KLHL34, PIK3R5, HSH2D, NT5E, ATP8A2, MGC21881, MX1, LOC374491, GAL3ST4, EIF2AK2, ITGA6, FAM179A, C1orf228, GP5, FUT6, ITGA6, S1PR5, OASL, 243819 PM at, HLA-DRB4///LOC100509582, SPON2, TTTY10, OASL, PATL2, LOC641518, YPEL1, C18orf49, MMRN1, SP 140L, 240507 PM at, IGF2BP3, C3orf14, 214376 PM at, FAM91A2///FLJ39739///LOC 100286793///LOC728855///LOC728875, IL4, 243947 PM s at, EIF2AK2, LOC100507192, MEST, TBX21, CCDC85C, MMP19, INPP5D, 220467 PM at, DSC1, OAS3, PRF1, 239798 PM at, ZBP 1, ADAR, GALM, 233121 PM at, RNF165, B4GALNT3, GZMB, KIAA0319L, C1orf57, FGFR2, BCAR4, LOC339988, TRIM39, FAM85A///FAM85B, LIMS1, ERBB2, 236191 PM at, HLA-A, MFSD4, NCAM1, GALM, 1566201 PM at, MX2, 237240 PM at, 232478 PM at, KIR2DL5A, 1569551 PM at, ZCCHC2, NUB1, PCDH9, RASGEF1A, 1560080 PM at, 243756 PM at, SYNM, CNPY3, RAPGEFL1, RIPK3, SOX13, KLRD1, GRAMD1B, LOC641365, TOR1B, SP110, TMLHE, 240438 PM at, SERPINE2, IER2, 234089 PM at, GNGT2, DEPDC1, 242096 PM at, NFKBID, EPHX2, PRF1, FGFBP2, XRCC4, AKAP5, XCL1///XCL2, 237221 PM at, 232793 PM at, 239479 PM x at, 1558836 PM at, LOC339988, IL11RA, 236220 PM at, B3GALNT1, GRHL1, LEF1, LOC100507492, DAAM1, STOX1, XCL1, VAMP5, LGMN, IL6ST, SETX, FGD3, C1orf21, PRSS23, KLRD1, 212444 PM at, 240893 PM at, C3orf52, UNKL, KIR3DL1///KIR3DL2///LOC727787, FLJ35220, MMP28, PTGDR, HERC5, OASL, IFI44, DDX60, OAS1, CMPK2, IFIT1, MX1, RSAD2, OAS2, HERC6, ISG15, OAS1, IFI6, LAMP5, IFIH1, OAS3, IFIT3, IFIT2, IFI44L, EPSTI1, IFIT3, IFIT2, OAS2, KIAA0114, IFI27, PARP9, IRF7, USP18, XAF1, PLSCR1, EPSTI1, RTP4, SHISA5, NT5C3, 228275 PM at, XAF1, IFITM1, IFI44, OAS2, HIST2H2AA3///HIST2H2AA4, GALNTL4, PLSCR1, HIST2H2AA3///HIST2H2AA4, HIST2H2BE, DDO, HIST1H2AC, IFI35, PARP12, SP100, EIF3L, 230314 PM at, SP100, 236798 PM at, SULF2, FAM179A, SAMD9, HIST1H2BD, LOC728769, HIST1H2BD, IFITM1, TDRD7, CMTM4, DDX58, ZNFX1, WDR8, UNC119B, GPAA1, HLA-C, DDX58, C2orf60, LOC10050697, HDLBP, PXK, SP110, GPAA1, PDXK, DHX58, UBA7, LGALS3BP, HIST1H2BE, KDELC1, ARPC1A, EIF2AK2, TDO2, C11orf2, C4orf33, HLA-B, ZNF684, IRF9, TMEM41A, 239988 PM at, GPR82, PPIF, RPL15, ZNF684, YBX1, RPL4, MAVS, SERPINA7, TRIM22, RPL4, TMEM41A, PIK3AP1, EIF3F, PEX11A, PNPT1, CSAG2///CSAG3, SSU72, DDO, ADAR, SULF2, GPAA1, RPL4, EEF2, CIAPIN1, EEF2, IFIT5, DDX60L, PPIF, LAP3, IFIT5, ZC3HAV1, RPL5, HLA-B, PPP3CC, B2M, HCP5, CTSB, HDLBP, RPS15A, SP110, PATL2, ESAM, IL17RB, SP110, TR1M34///TRIM6-TRIM34, NR1H4, SP100, NR1H4, IL18BP, EIF2AK2, TDO2, RPS6KA2, IP6K2, HLA-G, HIST1H2BB///HIST1H2BC///HIST1H2BD///HIST1H2BE///HIST1H2BG///HIST1H2BH///HIST1H2BI, ENO3, TRIM14, EEF1A1, PDHX, IL17RB, COG2, EIF4B, CBWD2, CMTM4, UGT1A8///UGT1A9, AFG3L2, LOC100506318, MARCO, HLA-A///LOC100507703, ACVRL1, SECTM1, SFRP5, C5orf44, SAMD9, 230795 PM at, HSBP1, LYPLAL1, HLA-C, LOC100505759, APOA1, NMI, CHD1L, FAM149A, UBA3, TPT1, PXK, FAM149A, KRT10, ZC3HAV1, CC2D2B, SELE, HLA-A///HLA-F///HLA-J, PEX3, FAM125A, HLA-G, ORMDL1, 1566249 PM at, CMAS, IL17RB, GLTSCR2, ST6GALNAC6, SP110, H2BFS, CYP11A1, EIF1, HIST1H2BC, 232140 PM at, DOK2, KLRD1, TPT1, VIL1, HLA-G, P2RY12, TLK2, 211976 PM at, SLU7, ZC3HAV1, HK3, DNASE1L1, 224603 PM at, CHMP5, BTN3A3, GOLGA7, WARS, IDS, 1560023 PM x at, GPD1, CREB1, SAMD9L, ZDHHC2, ETV7, UBA7, CD47, STX17, KLRK1, 1563075 PM s at, PARP14, NECAP1, RPL5, HIST1H2BI, SEPTIN 4, 239979 PM at, SEPHS1, UBE2L6, EEF1G, LOC25845, HIST1H2BF, ATPSB, HLA-F, PCBP2, PIAS2, HLA-DQB1///LOC100133583, GMDS, SYNPO2, FECH, HLA-C, RPL3, UGT2A3, TCIRG1, BTN3A2, LOC283481, SRGN, GBP2, VSIG10L, QRSL1, VPS26B, APOA1, HLA-A, BST2, PXK, KRT10, SUCLG1, SLC25A28, BTN3A2///BTN3A3, N4BP1, ATP5C1, LILRB1, MDK, LOC100129794, MRPL35, GBP5, HLA-B, POU5F1P4, AGBL5, SORBS3, RNF10, CHD1L, ZNF627, TPCN1, TRIM38, HLA-G, WDR77, MLEC, ZFYVE16, EEF1G, RPRD1A, OSBPL11, CA14, EBAG9, C14orf159, 213675 PM at, PTGFR, CDC5L, CNP, DPP8, MAL2, PTEN///PTENP1, HLA-DQB1, FAM83E, PRIC285, TIMM17A, VIL1, STK10, CTSS, TMEM20, 240681 PM at, GPR82, TPT1, CHMP5, PRSS36, TRIM14, 43511 PM s at, C12orf41, RPS6KC1, MS4A6A, and SPATA20 are detected.

3. The method of claim 1, further comprising for each of the at least five genes comparing the detected mRNA level of the gene relative to one or more reference levels indicating presence or absence of liver transplant rejection.

4. The method of claim 1, wherein the subject is human.

5. The method of claim 1, wherein the subject is suspected of having acute rejection of the liver transplant.

6. The method of claim 1, wherein the sample of nucleic acids is derived from a blood sample.

7. The method of claim 6, wherein the blood sample is a peripheral blood sample.

8. The method of claim 1, wherein the detecting of the acute rejection in the liver transplant has a negative predictive value (NPV) of greater than 75%.

9. The method of claim 1, wherein the immunosuppressive drug or new immunosuppressive drug is a calcineurin inhibitor, an mTOR inhibitor, an anti-proliferative, a corticosteroid, or an anti-T-cell antibody.

10. The method of claim 1, wherein the genes are selected from the group consisting of: lysosomal trafficking regulator (LYST), prune homolog 2 (PRUNE2), aminopeptidase puromycin sensitive pseudogene (LOC440434), chromosome 18 open reading frame 49 (C18orf49), and DnaJ (Hsp40) homolog, subfamily C, member 3 (DNAJC3).

11. The method of claim 1, wherein the administering the immunosuppressant at an altered dose or frequency comprises decreasing the dose or frequency of the immunosuppressant when the sample is classified as not undergoing acute rejection.

12. The method of claim 1, wherein the administering the immunosuppressant at an altered dose or frequency comprises increasing the dose or frequency of the immunosuppressant when the sample is classified as undergoing acute rejection.

13. The method of claim 1, wherein the trained algorithm comprises a linear discriminant analysis, fisher's linear discriminant, naïve bayes classifier, perceptron, support vector machine, diagonal linear discriminant analysis, nearest centroid, or prediction analysis of microarrays algorithm.

\* \* \* \* \*